US009125884B2

(12) United States Patent
MacBeth et al.

(10) Patent No.: US 9,125,884 B2
(45) Date of Patent: Sep. 8, 2015

(54) METHODS FOR TREATING CANCERS USING ORAL FORMULATIONS OF CYTIDINE ANALOGS

(71) Applicant: Celgene Corporation, Summit, NJ (US)

(72) Inventors: Kyle J. MacBeth, San Francisco, CA (US); Aaron N. Nguyen, San Jose, CA (US); Jorge DiMartino, Belmont, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 13/665,778

(22) Filed: Oct. 31, 2012

(65) Prior Publication Data
US 2013/0109644 A1    May 2, 2013

Related U.S. Application Data

(60) Provisional application No. 61/554,344, filed on Nov. 1, 2011.

(51) Int. Cl.
A01N 43/04 (2006.01)
A61K 31/70 (2006.01)
A61K 31/282 (2006.01)
A61K 31/706 (2006.01)
A61K 31/7052 (2006.01)
A61K 31/7042 (2006.01)
A61K 31/337 (2006.01)
A61K 31/7068 (2006.01)
A61K 45/06 (2006.01)

(52) U.S. Cl.
CPC ............. A61K 31/282 (2013.01); A61K 31/337 (2013.01); A61K 31/706 (2013.01); A61K 31/7042 (2013.01); A61K 31/7052 (2013.01); A61K 31/7068 (2013.01); A61K 45/06 (2013.01)

(58) Field of Classification Search
None
See application file for complete search history.

(56) References Cited

U.S. PATENT DOCUMENTS

| 5,916,596 | A | 6/1999 | Desai et al. |
| 6,506,405 | B1 | 1/2003 | Desai et al. |
| 6,537,579 | B1 | 3/2003 | Desai et al. |
| 6,749,868 | B1 | 6/2004 | Desai et al. |
| 7,820,788 | B2 | 10/2010 | Desai et al. |
| 8,034,765 | B2 | 10/2011 | De et al. |
| 2004/0162263 | A1 | 8/2004 | Sands et al. |
| 2006/0074046 | A1* | 4/2006 | Redkar et al. ................ 514/49 |
| 2006/0128654 | A1 | 6/2006 | Tang et al. |
| 2008/0057086 | A1 | 3/2008 | Etter et al. |
| 2009/0286752 | A1 | 11/2009 | Etter et al. |
| 2010/0048499 | A1 | 2/2010 | Desai et al. |
| 2010/0311683 | A1 | 12/2010 | Beach et al. |
| 2011/0319355 | A1 | 12/2011 | Nguyen et al. |

FOREIGN PATENT DOCUMENTS

| WO | WO 2006/034154 | 3/2006 |
| WO | WO 2006/089290 | 8/2006 |
| WO | 2008057562 A1 | 5/2008 |
| WO | 2009126175 A1 | 10/2009 |
| WO | 2009126401 A1 | 10/2009 |
| WO | 2009126938 A1 | 10/2009 |
| WO | WO 2009/139888 | 11/2009 |
| WO | WO 2010/059969 | 5/2010 |
| WO | 2011/156119 A1 | 12/2011 |
| WO | 2011156119 A1 | 12/2011 |
| WO | WO 2013/022872 | 2/2013 |

OTHER PUBLICATIONS

Manero et al. Leukemia (2008), vol. 22, pp. 1680-1684.*
Kritz et al. American Journal of Hematology (1996), vol. 51, pp. 117-121.*
Li et al. American Journal of Obstetrics & Gynecology (2009) pp. 177.e1-177.e9.*
Jabbour et al. Cancer (2008), vol. 112, pp. 2341-2351.*
Shang et al. Cancer Letters (2009), vol. 278, pp. 82-87.*
Stinchcombe et al. Cancer Chemother Pharmacol (2007), vol. 60, pp. 759-766.*
Anonymous, "A Phase I/II Clinical Trial of Vidaza with Abraxane in the Treatment of Patients with Advanced or Metastatic Solid Tumors and Breast Cancer," ClinicalTrials.gov archive, pp. 1-3, retrieved from the Internet: http://clinicaltrials.gov/archive/NCT00748553/2011_08_05, on Jan. 31, 2013.
Anonymous, "Oral Azacitidine as a Single Agent and in Combination with Carboplatin or Abraxane in Subjects with Relapsed or Refractory Solid Tumors," ClinicalTrials.gov archive, pp. 1-4, retrieved from the Internet: http://clinicaltrials.gov/archive/NCT01478685/2011_11_22, on Jan. 31, 2013.
Aparicio et al., "Review of the Clinical Experience with 5-Azacytidine and 5-Aza-2'-Deoxycytidine in Solid Tumors," Current Opinion in Investigational Drugs, 3(4):627-33 (2002).
Bast et al., "A Phase IIa Study of a Sequential Regimen Using Azacitidine to Reverse Platinum Resistance to Carboplatin in Patients with Platinum Resistant or Refractory Epithelial Ovarian Cancer," Journal of Clinical Oncology, 26, Abstract 3500, (2008).
Bellet et al., "Clinical Trial with Subcutaneously Administered 5-Azacytidine (NSC-102816)," Cancer Chemotherapy Reports, Part I, 58(2):217-22 (1974).
Bellet et al., "Phase II Study of Subcutaneously Administered 5-Azacytidine (NSC-102816) in Patients with Metastatic Maligant Melanoma," Medical and Pediatric Oncology, 41:11-15 (1978).
Bhuyan et al., "Cell Cycle Phase Specificity of Antitumor Agent," Cancer Research, 32:398-407 (1972).

(Continued)

Primary Examiner — Patrick Lewis
(74) Attorney, Agent, or Firm — Jones Day

(57) ABSTRACT

Provided herein are methods for treating subjects having a cancer, such as a relapsed or refractory solid tumor, wherein the method comprises administering to the subject a cytidine analog. In certain of the methods, the cytidine analog is administered alone or in combination with one or more anti-cancer agents. Also provided are methods for using a cytidine analog, to treat diseases and disorders including disorders related to abnormal cell proliferation, hematologic disorders, and immune disorders, among others. In certain of the methods, the cytidine analog is formulated in an oral dosage form and administered orally.

22 Claims, 6 Drawing Sheets

(56) References Cited

OTHER PUBLICATIONS

Bhuyan et al., "Cell-Kill Kinetics of Several S-Phase-Specific Drugs," Cancer Research, 33:888-94 (1973).
Brock et al., "DNA Methylation Markers and Early Recurrence in Stage I Lung Cancer," New England Journal of Medicine, 358(11):1118-28 (2008).
Christman et al., "5-Azacytidine and 5-Aza-2'-Deoxycytidine as Inhibitors of DNA Methylation: Mechanistic Studies and Their Implications for Cancer Therapy," Oncogene, 21:5483-95 (2002).
Cowan et al., "Will DNA Methylation Inhibitors Work in Solid Tumors? A Review of the Clinical Experience with Azacitidine and Decitabine in Solid Tumors," Epigenomics, Future Medicine Ltd, United Kingdom, 2(1):71-86 (2010).
Cunningham et al., "Comparison of 5-Azacytidine (NSC-102816) with CCNU (NSC-79037) in the Treatment of Patients with Breast Cancer and Evaluation of the Subsequent Use of Cyclophosphamide (NSC-26271)," Cancer Chemotherapy Reports, Part I, 58(5):677-81 (1974).
Curt et al., "A Phase I and Pharmacokinetic Study of Dihydro-5-Azacytidine (NSC 264880)," Cancer Research, 45:3359-63 (1985).
Das et al., "Methylation Mediated Silencing of TMSI/ASC Gene in Prostate Cancer," Molecular Cancer, 5(28), doi: 10.1186/1476-4598-5-28, available at http://www.molecular-cancer.com/content/5/1/28 (2006).
Dover et al., "5-Azacytidine Increases HbF Production and Reduces Anemia in Sickle Cell Disease: Dose-Response Analysis of Subcutaneous and Oral Dosage Regimens," Blood, 66(3):527-32 (1985).
Fenaux et al., "Efficacy of Azacitidine Compared with that of Conventional Care Regimens in the treatment of Higher-Risk Myelodysplastic Syndromes: A Randomised, Open-Label, Phase III Study," The Lancet Oncology, 10(3):223-32 (2009).
Garcia-Manero, "Demethylating Agents in Myeloid Malignancies," Current Opinion in Oncology, 20:705-10 (2008).
Garcia-Manero et al., "A Pilot Pharmacokinetic Study of Oral Azacitidine," Leukemia, 22:1680-84 (2008).
Gifford et al., "The Acquisition of hMLH1 Methylation in Plasma DNA After Chemotherapy Predicts Poor Survival for Ovarian Cancer Patients," Clinical Cancer Research, 10:4420-26 (2004).
Glaser, "HDAC Inhibitors: Clinical Update and Mechanism-Based Potential," Biochem. Pharm., 74:659-71 (2007).
Howell et al., "Demethylating Agents in the Treatment of Cancer," Pharmaceuticals, 3(7):2022-44 (2010).
Israili et al., "The Disposition and Pharmacokinetics in Humans of 5-Azacytidine Administered Intravenously as a Bolus or by Continuous Infusion," Cancer Research, 36:1453-61 (1976).
Jubb, et al., "Methylation and Colorectal Cancer," Journal of Pathology, 195:111-34 (2001).
Juergens et al., "Interim Analysis of a Phase II Trial of 5-Azacitidine (5AC) and Entinostat (SNDX-275) in Relapsed Advanced Lung Cancer (NSCLC)," Journal of Clinical Oncology, 27(15S):8055 (2009).
Kornblith et al., "Impact of Azacytidine on the Quality of Life of Patients with Myelodysplastic Syndrome Treated in a Randomized Phase III Trial: A Cancer and Leukemia Group B Study," Journal of Clinical Oncology, 20(10):2441-52 (2002).
Kritz et al., "Pilot Study of 5-Azacytidine (5-AZA) and Carboplatin (CBDCA) in Patients with Relapsed/Refractory Leukemia," American Journal of Hematology, 51(2):117-21 (1996).
Li et al., "Phase Specificity of 5-Azacytidine Against Mammalian Cells in Tissue Culture," Cancer Research, 30:2770-75 (1970).
Lomen et al., "Phase I Study of 5-Azacytidine (NSC-102816) Using 24-Hour Continuous Infusion for 5 Days," Cancer Chemotherapy Reports, Part I, 59(6):1123-26 (1975).
Moertel et al., "Phase II Study of 5-Azacytidine (NSC-102816) in the Treatment of Advanced Gastrointestinal Cancer," Cancer Chemotherapy Reports, Part I, 56(5):649-52 (1972).
Momparler, "Epigenetic Therapy of Cancer with 5-Aza-2'-Deoxycitidine (Decitabine)," Seminars in Oncology, 32(5):443-51 (2005).
Neil et al., "Enhancement by Tetrahydrouridine (NSC-112907) of the Oral Activity of 5-Azacytidine (NSC-102816) in L1210 Leukemic Mice," Cancer Chemotherapy Reports, Part I, 59(3):459-65 (1975).
Quagliana et al., "Phase II Study of 5-Azacytidine in Solid Tumor," Cancer Treatment Reports, 61(1):51-54 (1977).
Shnider et al., "A Phase I Study of 5-Azacytidine (NSC-102816)," Journal of Clinical Pharmacology, 205-12 (1976).
Silverman et al., "Randomized Controlled Trials of Azacitidine in Patients with the Myelodysplastic Syndrome: A Study of the Cancer and Leukemia Group B," Journal of Clinical Oncology, 20(10):2429-40 (2002).
Silverman et al., "Further Analysis of Trials with Azacitidine in Patients with Myelodysplastic Syndrome: Studies 8421, 8921, and 9221 by the Cancer and Leukemia Group B," Journal of Clinical Oncology, 24(24):3895-3903 (2006).
Skikne et al., "A Phase I, Open-Label, Dose-Escalation Study to Evaluate the Safety, Pharmacokinetics, and Pharmacodynamics of Oral Azacitidine in Subjects with Myelodysplastic Syndromes (MDS) or Acute Myelogenous Leukemia (AML)," Journal of Clinical Oncology (May 20, 2008 Supplement), 2008 ASCO Annual Meeting Proceedings, Part I, 26(15S), poster # 7091 (2008).
Srinivasan et al., "Phase II Study of 5-Azacytidine in Sarcomas of Bone," American Journal of Clinical Oncology, 5:411-15 (1982).
Stathis et al., "Phase I Study of Decitabine in Combination with Vorinostat in Patients with Advanced Solid Tumors and Non-Hodgkin's Lymphomas," Clinical Cancer Research, 17(6):1582-90 (2011).
Stoltz et al., "Development of an Oral Dosage Form of Azacitidine: Overcoming Challenges in Chemistry, Formulation, and Bioavailability," Blood, 48$^{th}$ ASH Annual Meeting, 108, poster # 4850 (2006).
Tan et al., "Clinical Trial of 5-Azacytidine (5-azaCR)," American Association for Cancer Research, 64$^{th}$ Annual Meetin , Apr. 11-13, 1973, Abstract # 385 (1973).
Troetel et al., "Absorption, Distribution, and Excretion of 5-Azacytidine (NSC-102816) in Man," Cancer Chemotherapy Reports, Part I, 56(3):405-11 (1972).
Velez-Garcia et al., "Twice Weekly 5-Azacitidine Infusion in Disseminated Metastatic Cancer: A Phase II Study," Cancer Treatment Reports, 61(9):1675-77 (1977).
Vogler et al., "5-Azacytidine (NSC 102816): A New Drug for the Treatment of Myeloblastic Leukemia," Blood, 48(3): 331-37 (1976).
Ward et al., "An Oral Dosage Formulation of Azacitidine: A Pilot Pharmacokinetic Study," Journal of Clinical Oncology (Jun. 20, 2007 Supplement), 2007 ASCO Annual Meeting Proceedings, Part I, 25(18S), poster # 7084 (2007).
Zaitseva et al., "Convergent Syntheses and Cytostatic Properties of 2-Chloro-2'-Deoxy-2'-Fluoroadenosine and its $N^7$-Isomer," Bioorg. & Med. Chem. Lett., 5(24):2999-3002 (1995).
Ziemba et al., "Development of Oral Demethylating Agents for the Treatment of Myelodysplastic Syndromes," American Association of Cancer Research, 100th Annual Meeting, Apr. 18-22, Abstract #3369 (2009).
Appleton K, et al., Phase I and pharmacodynamic trial of the DNA methyltransferase inhibitor decitabine and carboplatin in solid tumors, J. Clin. Oncol., 2007, 25(29):4603-4609.
Dumlao TL, et al., A phase I/II study of the hypomethylating agent azacitadine with the nanoparticle albumin bound paclitaxel in the treatment of patients with advanced or metastatic solid tumors, J. Clin. Oncol. (Meeting Abstracts), 2011, 29(15):Suppl 3095.
Garcia-Manero G, et al., Phase I study of oral azacitidine in myelodysplastic syndromes, chronic myelomonocytic leukemia, and acute myeloid leukemia, J. Clin. Oncol., 2011, 29(18):2521-2527.
Gordian E, et al., Methylation mediated silencing of TMSI in breast cancer and its potential contribution to docetaxel cytotoxicity, Anticancer Res., 2009, 29(8):3207-3210.
Kaminskas E, et al., FDA Drug Approval Summary: Azacitidine (5-azacytidine, Vidaza™) for Injectable Suspension, The Oncologist, 2005, 10(3):176-182.
Li Y, et al., Azacitidine enhances sensitivity of platinum-resistant ovarian cancer cells to carboplatin through induction of apoptosis, Am. J. Obstet. Gynecol., 2009, 200(2):177.e1-9.

(56) References Cited

OTHER PUBLICATIONS

Pohlmann P, et al., Phase II trial of cisplatin plus decitabine, a new DNA hypomethylating agent, in patients with advanced squamous cell carcinoma of the cervix, Am. J. Clin. Oncol. 2002, 25(5):496-501.

Santos FP, et al., Decitabine in the treatment of myelodysplastic syndromes, Expert Rev. Anticancer Ther., 2010, 10 (1):9-22.

Schaefer M, et al., Azacytidine inhibits RNA methylation at DNMT2 target sites in human cancer cell lines, Cancer Res. 2009, 69(20):8127-8132.

Schwartsmann G, et al., A phase I trial of cisplatin plus decitabine, a new DNA-hypomethylating agent, in patients with advanced solid tumors and a follow-up early phase II evaluation in patients with inoperable non-small cell lung cancer, Invest. New Drugs, 2000, 18(1):83-91.

Stresemann C, et al., Modes of action of the DNA methyltransferase inhibitors azacitidine and decitabine, Int. J. Cancer, 2008, 123(1):8-13.

Venturelli S, et al., Dual antitumour effect of 5-azacytidine by inducing a breakdown of resistance-mediating factors and epigenetic modulation, Gut, 2011, 60(2):156-165.

Beran et al., "Phase I study of oral topotecan in hematological malignancies," Clinical Cancer Res., 9:4084-4091 (2003).

Boyer, M. "Cancer, A Comprehensive Clinical Guide," David Morris, John Kearsley & Chris Williams eds., Harwood Academic Publishers, pp. 49-51 (1998).

Nies, A. S. "Goodman & Gilman's, The Pharmacological Basis of Therapeutics," Tenth Edition, McGraw-Hill pp. 54-56 (2001).

\* cited by examiner

Figure 1: Dosing and Sampling Schema for Part 1, Arm A
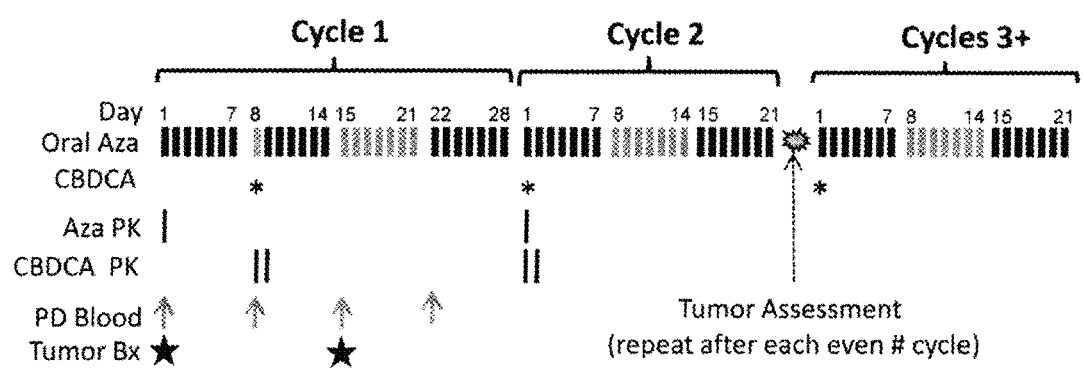

Figure 2: Dosing and Sampling Schema for Part 1 Arm B
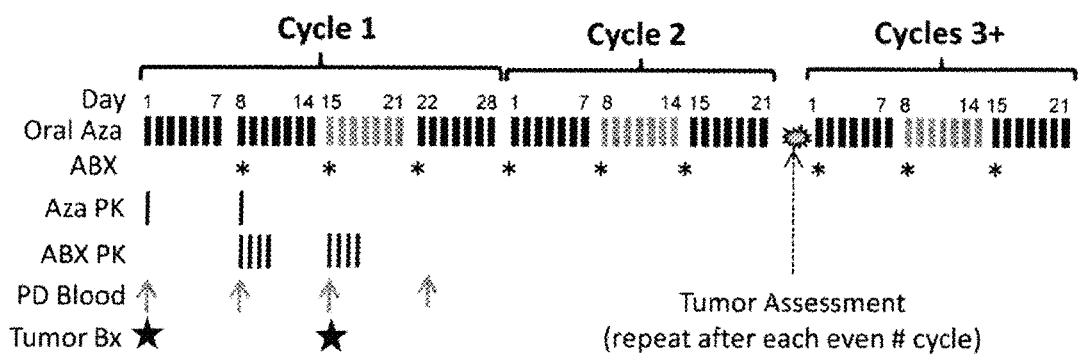
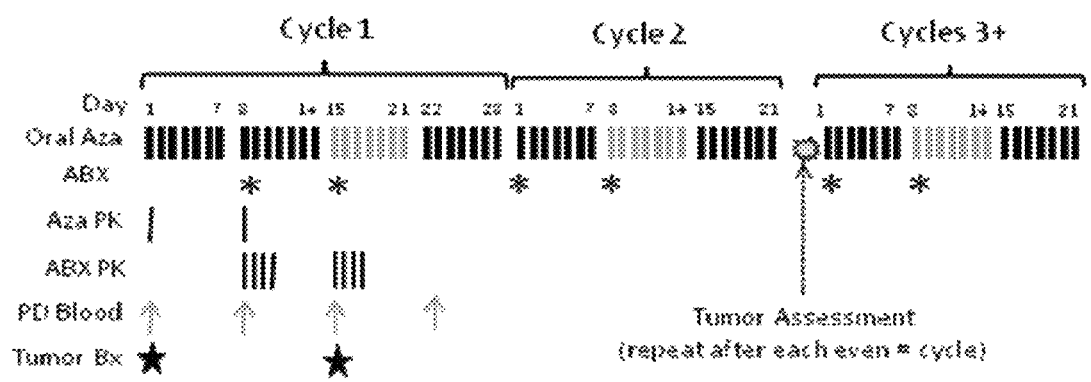

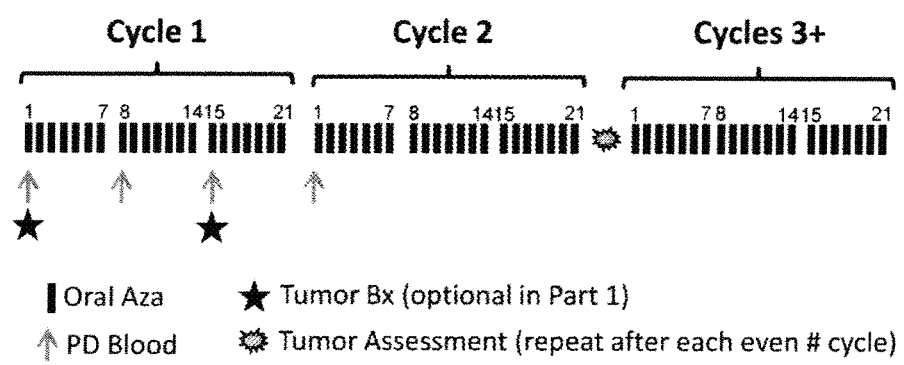
Figure 3: Dosing and Sampling Schedule for Arm C

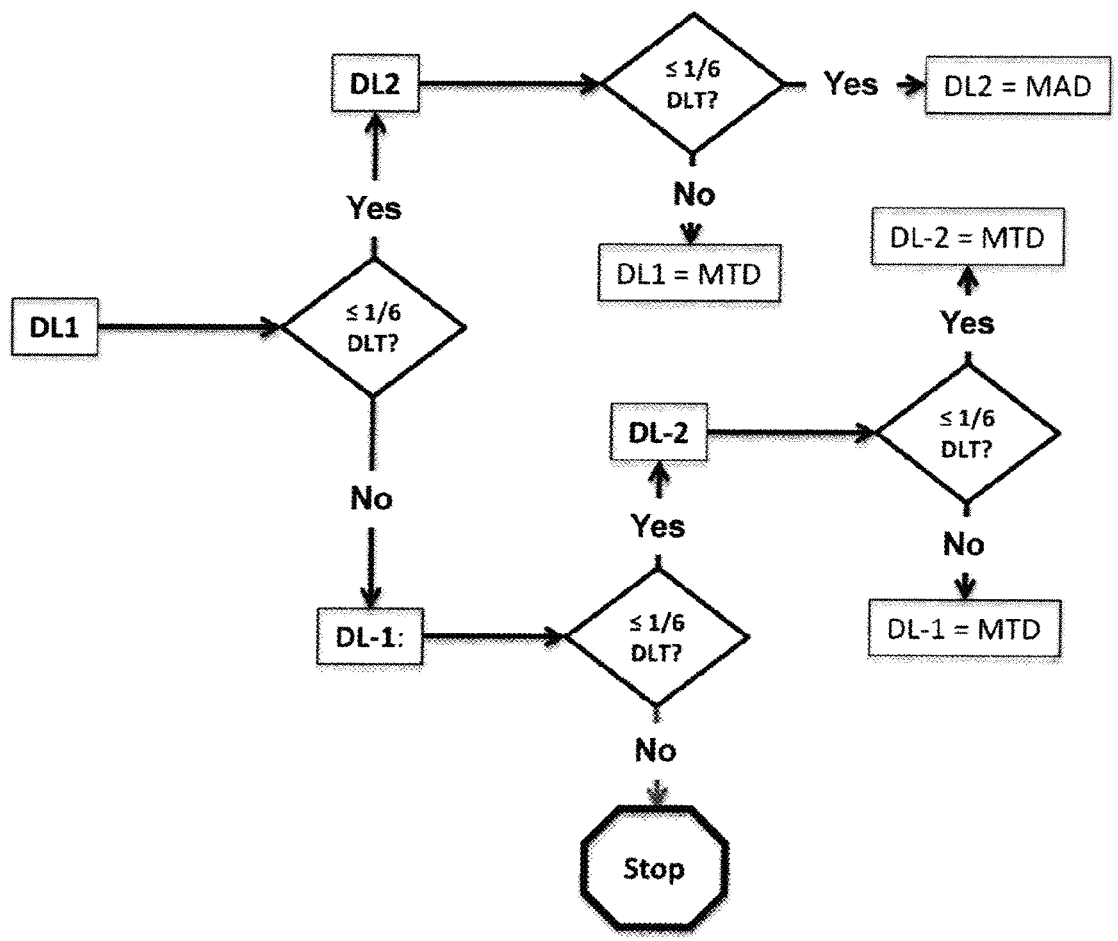
Figure 4: Dose Escalation for Arms A and B

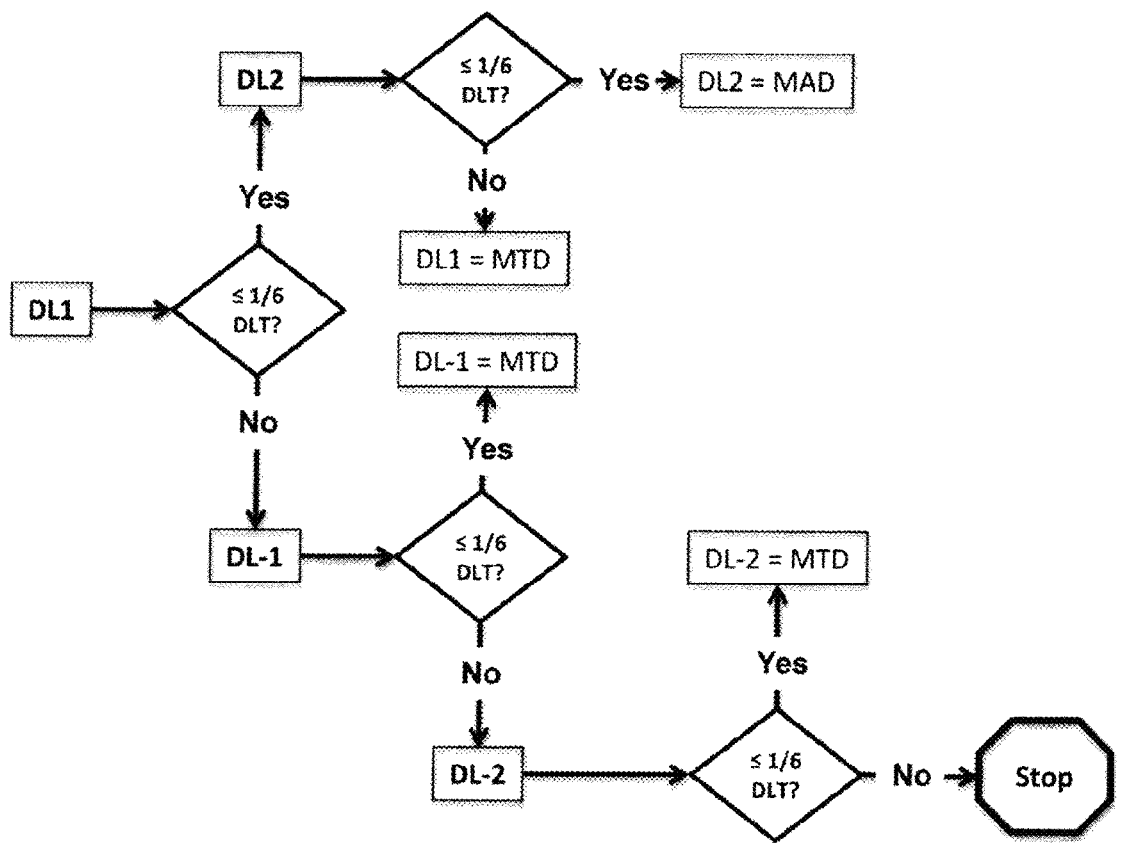
Figure 5: Dose Escalation for Arm C

Figure 6: Modeling of Clinical Dosing Schema
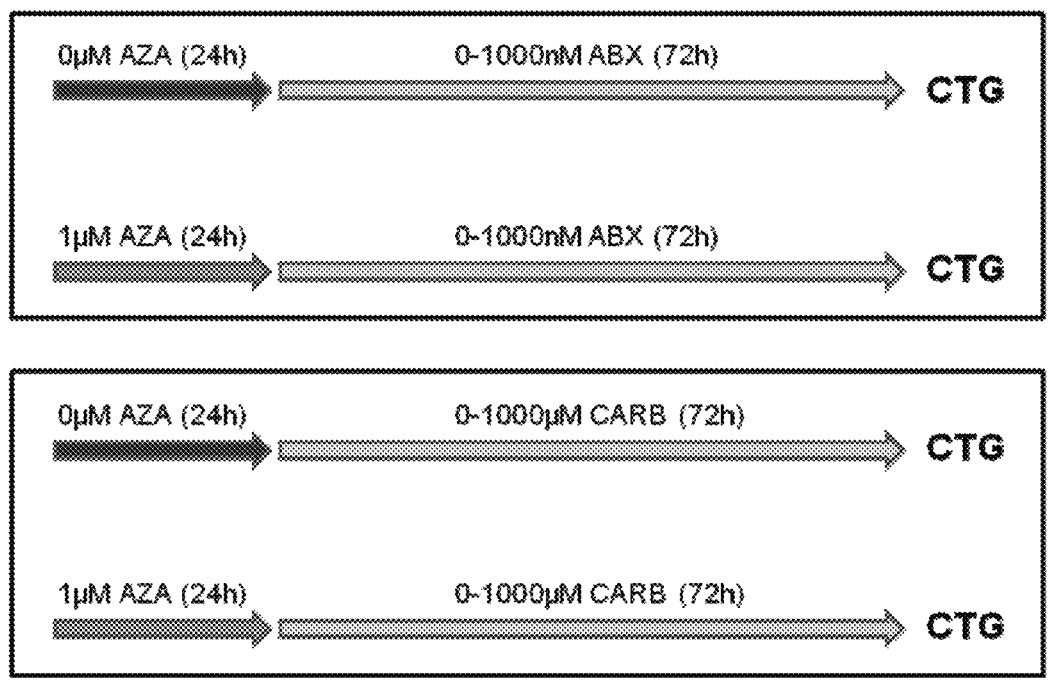

METHODS FOR TREATING CANCERS USING ORAL FORMULATIONS OF CYTIDINE ANALOGS

This application claims priority to U.S. Provisional Patent Application No. 61/554,344, filed Nov. 1, 2011, which is hereby incorporated by reference in its entirety.

I. FIELD

Provided herein are methods for treating, preventing, or managing cancers using a cytidine analog, or a salt, solvate, or hydrate thereof. Also provided are methods for using a cytidine analog, or a salt, solvate, or hydrate thereof, to treat, prevent, or manage diseases and disorders including disorders related to abnormal cell proliferation, hematologic disorders, and immune disorders, among others. In certain of the methods, the cytidine analog is formulated in an oral dosage form and administered orally. In certain of the methods, the cytidine analog is administered alone or in combination with one or more anti-cancer agents.

II. BACKGROUND

Cancer is a major worldwide public health problem; in the United States alone, approximately 570,000 cancer-related deaths were expected in 2005. See, e.g., Jemal et al., *CA Cancer J. Clin.* 55(1):10-30 (2005). Many types of cancer have been described in the medical literature. Examples include cancer of the blood, bone, lung (e.g., non-small-cell lung cancer and small-cell lung cancer), colon, breast, prostate, ovary, brain, and intestine. The incidence of cancer continues to climb as the general population ages and as new forms of cancer develop. A continuing need exists for effective therapies to treat subjects with cancer.

Nucleoside analogs have been used clinically for the treatment of viral infections and certain cancers. Most nucleoside analogs are classified as anti-metabolites. After they enter the cell, nucleoside analogs are successively phosphorylated to nucleoside 5'-mono-phosphates, di-phosphates, and tri-phosphates.

The nucleoside analogs 5-azacytidine (also known as 4-amino-1-β-D-ribofuranosyl-1,3,5-triazin-2(1H)-one; National Service Center designation NSC-102816; CAS Registry Number 320-67-2; azacitidine; Aza and AZA; and currently marketed as VIDAZA®) and 2'-deoxy-5-azacytidine (also known as 5-aza-2'-deoxycytidine, decitabine, 5-aza-CdR, Dac, and DAC, and currently marketed as DACOGEN®) are DNA methyltransferase (DNMT) inhibitors that have been approved by the U.S. Food and Drug Administration for the treatment of myelodysplastic syndromes (MDS). Azacitidine and decitabine are cytidine analogs; a structural difference between these cytidine analogs and their related natural nucleosides is the presence of a nitrogen at position 5 of the cytosine ring in place of a carbon. Azacitidine may be defined as having a molecular formula of $C_8H_{12}N_4O_5$, a molecular weight of 244.21 grams per mole, and a structure as shown below. Decitabine may be defined as having a molecular formula of $C_8H_{12}N_4O_4$, a molecular weight of 228.21 grams per mole, and a structure as shown below.

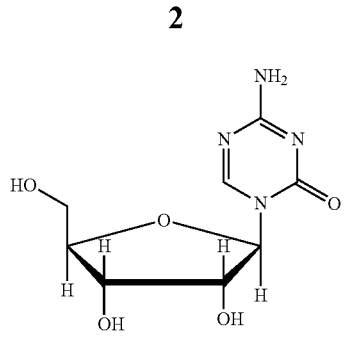

Azacitidine

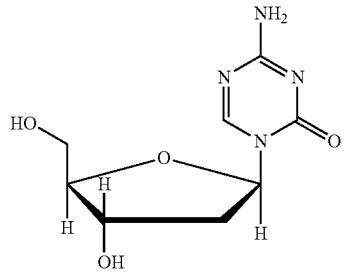

Decitabine

After its incorporation into replicating DNA, 5-azacytidine or 5-aza-2'-deoxycytidine can form a covalent complex with DNA methyltransferases. DNA methyltransferases are responsible for de novo DNA methylation and for reproducing established methylation patterns in daughter DNA strands of replicating DNA. Inhibition of DNA methyltransferases can lead to DNA hypomethylation, thereby restoring normal functions to morphologically dysplastic, immature cells by re-expression of genes involved in normal cell cycle regulation, differentiation and death. The cytotoxic effects of cytidine analogs can cause the death of rapidly dividing cells that are no longer responsive to normal cell growth control mechanisms. 5-Azacytidine, unlike 5-aza-2'-deoxycytidine, also incorporates into RNA. The cytotoxic effects of azacitidine may result from multiple mechanisms, including inhibition of DNA, RNA and protein synthesis, incorporation into RNA and DNA, and activation of DNA damage pathways.

5-Azacytidine and 5-aza-2'-deoxycytidine have been tested in clinical trials and showed significant activity, such as, for example, in the treatment of myelodysplastic syndromes (MDS), acute myelogenous leukemia (AML), chronic myelogenous leukemia (CML), acute lymphocytic leukemia (ALL), and non Hodgkin's lymphoma (NHL). See, e.g., Aparicio et al., *Curr. Opin. Invest. Drugs* 3(4): 627-33 (2002). 5-Azacytidine has undergone NCI-sponsored trials for the treatment of MDS and has been approved for treating all FAB subtypes of MDS. See, e.g., Kornblith et al., *J. Clin. Oncol.* 20(10): 2441-2452 (2002); Silverman et al., *J. Clin. Oncol.* 20(10): 2429-2440 (2002). 5-Azacytidine may alter the natural course of MDS by diminishing the transformation to AML through its cytotoxic activity and its inhibition of DNA methyltransferase. In a Phase III study, 5-azacytidine administered subcutaneously significantly prolonged survival and time to AML transformation or death in subjects with higher-risk MDS. See, e.g., P. Fenaux et al., *Lancet Oncol.*, 2009, 10(3):223-32; Silverman et al., *Blood* 106(11): Abstract 2526 (2005).

Other members of the class of cytidine analogs include, for example: 1-β-D-arabinofuranosylcytosine (Cytarabine or ara-C); pseudoisocytidine (psi ICR); 5-fluoro-2'-deoxycytidine (FCdR); 2'-deoxy-2',2'-difluorocytidine (Gemcitabine);

5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxycarbonyl-5'-deoxy-5-fluorocytidine (Capecitabine); $N^4$-octadecyl-cytarabine; and elaidic acid cytarabine.

5-Azacytidine and certain other cytidine analogs are approved for subcutaneous (SC) or intravenous (IV) administration to treat certain proliferative disorders. Oral dosing of cytidine analogs would be more desirable and convenient for patients and doctors, e.g., by eliminating injection-site reactions that may occur with SC administration and/or by permitting improved patient compliance. However, oral delivery of cytidine analogs has proven difficult due to combinations of chemical instability, enzymatic instability, and/or poor permeability. For example, cytidine analogs have been considered acid labile and unstable in the acidic gastric environment. Previous attempts to develop oral dosage forms of cytidine analogs have required enteric coating of the drug core to protect the active pharmaceutical ingredient (API) from what was understood and accepted to be therapeutically unacceptable hydrolysis in the stomach, such that the drug is preferably absorbed in specific regions of the lower gastrointestinal tract, such as the jejunum in the small intestine. See, e.g., Sands, et al., U.S. Patent Publication No. 2004/0162263 (application Ser. No. 10/698,983). In addition, a generally accepted belief in the art has been that water leads to detrimental hydrolytic degradation of cytidine analogs during formulation, subsequently affecting the stability of the API in the dosage form. As a result, coatings applied to the drug core for prospective oral delivery of cytidine analogs have previously been limited to organic solvent-based systems to minimize exposure of the API to water.

III. SUMMARY

Provided herein are methods for treating, preventing, or managing cancers using a cytidine analog, or a salt, solvate, or hydrate thereof. Also provided are methods for using a cytidine analog, or a salt, solvate, or hydrate thereof, to treat, prevent, or manage diseases and disorders, including disorders related to abnormal cell proliferation, hematologic disorders, and immune disorders, among others. In one embodiment, the cancer is a solid tumor. In one embodiment, the cancer is relapsed or refractory. In one embodiment, the cancer is a cancer of the breast, lung, head and neck, ovary, testicle, prostate, gastrointestinal system, stomach, pancreas, liver, colon, kidney, bladder, brain, skin, or bone, among others. In one embodiment, the cancer is a cancer of the blood or the lymph. In particular embodiments, the cancer is a relapsed or refractory solid tumor. In particular embodiments, the cancer is a cancer of the bladder, ovary, pancreas, lung, colon, head and neck, breast, or skin. In particular embodiments, the cancer is a cancer of the bladder, ovary, pancreas, lung, or colon.

In one embodiment, the cytidine analog is formulated in an oral dosage form provided herein (e.g., a tablet or a capsule). In one embodiment, the cytidine analog is administered orally to a subject in need thereof. In one embodiment, the cytidine analog is administered to a subject in need thereof for a sustained period of time. In one embodiment, the cytidine analog is administered to a subject in need thereof cyclically (e.g., dosing for one or more days, followed by a resting period). In one embodiment, the cytidine analog is administered to a subject in need thereof over multiple dosing cycles.

In one embodiment, the cytidine analog is administered alone as a single agent to a subject in need thereof. In one embodiment, the cytidine analog is administered in combination with one or more additional anti-cancer agent(s), including, but not limited to, carboplatin, paclitaxel, or Abraxane® (paclitaxel protein-bound particles), among others. In one embodiment, the additional anti-cancer agent is an alkylating agent, a cytotoxic agent, an anti-angiogenic agent, an anti-tubulin agent, an anti-metabolite, a kinase inhibitor, a biologics agent, or any other known anti-cancer agent (e.g., an anti-cancer agent provided herein elsewhere). In certain embodiments, in addition to the cytidine analog or the one or more additional anti-cancer agent(s), an anti-emetic is administered to a subject in need thereof.

In one embodiment, the cytidine analog is administered orally or parenterally. In one embodiment, the cytidine analog is administered orally. In particular embodiments, 5-azacytidine is administered orally. In one embodiment, the additional anti-cancer agent is administered orally or parenterally. In one embodiment, the cytidine analog is administered via the same route as the one or more additional anti-cancer agent(s). In one embodiment, the cytidine analog is administered via a different route as the one or more additional anti-cancer agent(s) (e.g., one administered orally and the other administered parenterally).

In one embodiment, the cytidine analog is administered in a particular dosing cycle. In one embodiment, the cytidine analog and the one or more additional anti-cancer agent(s) (including, but not limited to, carboplatin, paclitaxel, or Abraxane®) are co-administered in a particular dosing cycle. In particular embodiments, the cytidine analog is first administered to a subject in need thereof for one or more days (e.g., for 7 days or more), and the one or more additional anti-cancer agent(s) is/are administered to the subject (e.g., starting on Day 8 or later of the treatment cycle). In particular embodiments, when the one or more additional anti-cancer agent(s) is/are administered to the subject, the cytidine analog is also administered to the subject. In particular embodiments, when the one or more additional anti-cancer agent(s) is/are administered to the subject, the cytidine analog is not administered to the subject simultaneously.

In one embodiment, provided herein are pharmaceutical compositions comprising a cytidine analog, wherein the compositions release the API substantially in the stomach upon oral administration. In one embodiment, provided herein are pharmaceutical compositions comprising a cytidine analog, wherein the compositions release the API substantially in the stomach and the upper intestine upon oral administration. Also provided are methods for making the compositions, and methods for using the compositions to treat, prevent, or manage diseases and disorders including cancer, disorders related to abnormal cell proliferation, solid tumors, and hematologic disorders.

In certain embodiments, the cytidine analog is 5-azacytidine. In other embodiments, the cytidine analog is 5-aza-2'-deoxycytidine (decitabine or 5-aza-CdR). In yet other embodiments, the cytidine analog is, for example: 1-β-D-arabinofuranosylcytosine (Cytarabine or ara-C); pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxycarbonyl-5'-deoxy-5-fluorocytidine (Capecitabine); $N^4$-octadecyl-cytarabine; elaidic acid cytarabine; or their derivatives or related analogs.

Certain embodiments herein provide compositions that are single unit dosage forms comprising a cytidine analog. Certain embodiments herein provide compositions that are non-enteric-coated. Certain embodiments herein provide compositions that are tablets comprising a cytidine analog. Certain embodiments herein provide compositions that are capsules comprising a cytidine analog. In certain embodiments, the single unit dosage forms optionally further contain one or more excipients. In certain embodiments, the tablets optionally further contain one or more excipients. In other embodiments, the capsules optionally further contain one or more excipients. In certain embodiments, the composition is a tablet that effects an immediate release of the API upon oral administration. In other embodiments, the composition is a tablet that effects a controlled release of the API substantially in the stomach. In other embodiments, the composition is a tablet that effects a controlled release of the API substantially in the stomach and the upper intestine. In certain embodiments, the composition is a capsule that effects an immediate release of the API upon oral administration. In other embodiments, the composition is a capsule that effects a controlled release of the API substantially in the stomach. In other embodiments, the composition is a capsule that effects a controlled release of the API substantially in the stomach and the upper intestine. In particular embodiments, the tablet contains a drug core that comprises a cytidine analog, and optionally further contains a coating of the drug core, wherein the coating is applied to the drug core using an aqueous solvent, such as, for example, water, or non-aqueous solvent, such as, for example ethanol.

Certain embodiments herein provide methods of making formulations of cytidine analogs intended for oral delivery. Further provided are articles of manufacture containing packaging material, an oral formulation of a cytidine analog, and a label that indicates that the formulation is for the treatment, prevention, or management of certain diseases or disorders including, e.g., a cancer, a disorder related to abnormal cell proliferation, a solid tumor, a hematologic disorder, or an immune disorder.

Certain embodiments herein provide methods of using the formulations provided herein to treat, prevent, or manage diseases or disorders including, e.g., cancer, disorders related to abnormal cell proliferation, solid tumors, hematologic disorders, or immune disorders. In certain embodiments, the formulations of cytidine analogs are orally administered to subjects in need thereof to treat, prevent, or manage a cancer; or a hematological disorder, such as, for example, MDS, AML, ALL, CML, NHL, leukemia, lymphoma, or multiple myeloma; or a solid tumor, such as, for example, sarcoma, melanoma, carcinoma, or cancer of the colon, breast, ovary, gastrointestinal system, kidney, bladder, lung (e.g., non-small-cell lung cancer and small-cell lung cancer), testicle, prostate, stomach, pancreas, liver, head and neck, brain, skin, or bone, among others. In particular embodiments, the cancer is a cancer of the bladder, ovary, pancreas, lung, colon, head and neck, breast, or skin. In particular embodiments, the cancer is a cancer of the bladder, ovary, pancreas, lung, or colon. In certain embodiments, the cancer is refractory. In certain embodiments, the cancer is relapsed. In certain embodiments, the cancer is metastatic. In certain embodiments, the formulations of cytidine analogs are orally administered to subjects in need thereof to treat, prevent, or manage an immune disorder. In certain embodiments, the oral formulations provided herein are co-administered with one or more therapeutic agents to provide a synergistic therapeutic effect in subjects in need thereof. In certain embodiments, the oral formulations provided herein are co-administered with one or more therapeutic agents to provide a resensitization effect in subjects in need thereof. The co-administered agents may be a cancer therapeutic agent, as described herein. In certain embodiments, the co-administered agent(s) may be dosed, e.g., orally or by injection. In certain embodiments, the cytidine and/or the co-administered agent(s) may be dosed cyclically.

In particular embodiments, provided herein are tablets containing 5-azacytidine and methods for making and using the tablets to treat, prevent, or manage cancer, disorders related to abnormal cell proliferation, solid tumors, or hematologic disorders. In certain embodiments, the tablets optionally further contain one or more excipients such as, for example, glidants, diluents, lubricants, colorants, disintegrants, granulating agents, binding agents, polymers, and/or coating agents. Examples of ingredients useful in preparing certain formulations provided herein are described in, e.g., Etter et al., U.S. Patent Publication No. 2008/0057086 (application Ser. No. 11/849,958), and Etter et al., U.S. Patent Publication No. 2009/0286752 (application Ser. No. 12/466,213), both of which are incorporated herein by reference in their entireties.

Specific embodiments herein provide, inter alia, pharmaceutical compositions comprising a therapeutically effective amount of 5-azacytidine. Specific embodiments herein provide, inter alia, pharmaceutical compositions comprising a therapeutically effective amount of 5-azacytidine, wherein the composition releases the 5-azacytidine substantially in the stomach following oral administration to a subject. Further embodiments provide the aforementioned compositions, which: are immediate release compositions; do not have an enteric coating (i.e., are non-enteric-coated); are tablets; are capsules; further comprise an excipient selected from any excipient disclosed herein; further comprise a permeation enhancer; further comprise d-alpha-tocopheryl polyethylene glycol 1000 succinate; further comprise a permeation enhancer in the formulation at about 2% by weight relative to the total weight of the formulation; are essentially free of a cytidine deaminase inhibitor; are essentially free of tetrahydrouridine; have an amount of 5-azacytidine of at least about 40 mg; have an amount of 5-azacytidine of at least about 50 mg; have an amount of 5-azacytidine of at least about 60 mg; have an amount of 5-azacytidine of at least about 80 mg; have an amount of 5-azacytidine of at least about 100 mg; have an amount of 5-azacytidine of at least about 120 mg; have an amount of 5-azacytidine of at least about 150 mg; have an amount of 5-azacytidine of at least about 200 mg; have an amount of 5-azacytidine of at least about 250 mg; have an amount of 5-azacytidine of at least about 300 mg; have an amount of 5-azacytidine of at least about 350 mg; have an amount of 5-azacytidine of at least about 400 mg; have an amount of 5-azacytidine of at least about 450 mg; have an amount of 5-azacytidine of at least about 500 mg; have an amount of 5-azacytidine of at least about 600 mg; have an amount of 5-azacytidine of at least about 1000 mg; have an amount of 5-azacytidine of about 40 mg; have an amount of 5-azacytidine of about 50 mg; have an amount of 5-azacytidine of about 60 mg; have an amount of 5-azacytidine of about 80 mg; have an amount of 5-azacytidine of about 100 mg; have an amount of 5-azacytidine of about 120 mg; have an amount of 5-azacytidine of about 150 mg; have an amount of 5-azacytidine of about 200 mg; have an amount of 5-azacytidine of about 250 mg; have an amount of 5-azacytidine of about 300 mg; have an amount of 5-azacytidine of about 350 mg; have an amount of 5-azacytidine of about 400 mg; have an amount of 5-azacytidine of about 450 mg; have an amount of 5-azacytidine of about 500 mg; have an amount of 5-azacytidine of about 600 mg; have an amount of 5-azacytidine of about 1000 mg; achieve an area-under-the-curve value of at least about 200 ng-hr/mL following oral administration to a subject; achieve an area-under-the-curve value of at least about 400 ng-hr/mL following oral administration to a subject; achieve a maximum plasma concentration of at least about 100 ng/mL following oral administration to a subject; achieve a maximum plasma concentration of at least about 200 ng/mL following oral administration to a subject; achieve a time to maximum plasma concentration of less than about 90 minutes following oral administration to a subject; and/or achieve a time to maximum plasma concentration of less than about 60 minutes following oral administration to a subject.

Specific embodiments herein provide, inter alia, methods for treating a subject having cancer or a disease associated with abnormal cell proliferation, comprising orally administering to the subject a pharmaceutical composition comprising a therapeutically effective amount of 5-azacytidine. Specific embodiments herein provide, inter alia, methods for treating a subject having cancer or a disease associated with abnormal cell proliferation, comprising orally administering to the subject a pharmaceutical composition comprising a therapeutically effective amount of 5-azacytidine, wherein the composition releases the 5-azacytidine substantially in the stomach following oral administration to the subject. Further embodiments herein provide the aforementioned methods, in which: the disease is myelodysplastic syndrome; the disease is acute myelogenous leukemia; the disease is cancer; the disease is a solid tumor; the disease is a cancer of the bladder, ovary, pancreas, lung, colon, head and neck, breast, or skin; the disease is a cancer of the bladder, ovary, pancreas, lung, or colon; the disease is a relapsed or refractory solid tumor; the method further comprises co-administering to the subject in need thereof an additional therapeutic agent selected from any additional therapeutic agent disclosed herein; the composition is an immediate release composition; the composition does not have an enteric coating; the composition further comprises a permeation enhancer; the composition further comprises the permeation enhancer d-alpha-tocopheryl polyethylene glycol 1000 succinate; the composition further comprises d-alpha-tocopheryl polyethylene glycol 1000 succinate in the formulation at about 2% by weight relative to the total weight of the formulation; the method further comprises not co-administering a cytidine deaminase inhibitor with the cytidine analog; the composition is a single unit dosage form; the composition is a tablet; the composition is a capsule; the composition further comprises an excipient selected from any excipient disclosed herein; the amount of 5-azacytidine is at least about 40 mg; the amount of 5-azacytidine is at least about 50 mg; the amount of 5-azacytidine is at least about 60 mg; the amount of 5-azacytidine is at least about 80 mg; the amount of 5-azacytidine is at least about 100 mg; the amount of 5-azacytidine is at least about 120 mg; the amount of 5-azacytidine is at least about 150 mg; the amount of 5-azacytidine is at least about 200 mg; the amount of 5-azacytidine is at least about 250 mg; the amount of 5-azacytidine is at least about 300 mg; the amount of 5-azacytidine is at least about 350 mg; the amount of 5-azacytidine is at least about 400 mg; the amount of 5-azacytidine is at least about 450 mg; the amount of 5-azacytidine is at least about 500 mg; the amount of 5-azacytidine is at least about 600 mg; the amount of 5-azacytidine is at least about 1000 mg; the amount of 5-azacytidine is about 40 mg; the amount of 5-azacytidine is about 50 mg; the amount of 5-azacytidine is about 60 mg; the amount of 5-azacytidine is about 80 mg; the amount of 5-azacytidine is about 100 mg; the amount of 5-azacytidine is about 120 mg; the amount of 5-azacytidine is about 150 mg; the amount of 5-azacytidine is about 200 mg; the amount of 5-azacytidine is about 250 mg; the amount of 5-azacytidine is about 300 mg; the amount of 5-azacytidine is about 350 mg; the amount of 5-azacytidine is about 400 mg; the amount of 5-azacytidine is about 450 mg; the amount of 5-azacytidine is about 500 mg; the amount of 5-azacytidine is about 600 mg; the amount of 5-azacytidine is about 1000 mg; the method achieves an area-under-the-curve value of at least about 200 ng-hr/mL following oral administration to the subject; the method achieves an area-under-the-curve value of at least about 400 ng-hr/mL following oral administration to the subject; the method achieves a maximum plasma concentration of at least about 100 ng/mL following oral administration to the subject; the method achieves a maximum plasma concentration of at least about 200 ng/mL following oral administration to the subject; the method achieves a time to maximum plasma concentration of less than about 90 minutes following oral administration to the subject; and/or the method achieves a time to maximum plasma concentration of less than about 60 minutes following oral administration to the subject.

IV. BRIEF DESCRIPTION OF THE DRAWINGS

FIG. 1: Dosing and sampling schema for Part 1, Arm A of a clinical study on orally dosed 5-azacytidine.

FIG. 2: Dosing and sampling schema for Part 1, Arm B of a clinical study on orally dosed 5-azacytidine.

FIG. 3: Dosing and sampling schema for Part 1, Arm C of a clinical study on orally dosed 5-azacytidine.

FIG. 4: Dose levels and dose escalation rules for Arms A and B of a clinical study on orally dosed 5-azacytidine.

FIG. 5: Dose levels and dose escalation rules for Arm C of a clinical study on orally dosed 5-azacytidine.

FIG. 6: Modeling of clinical dosing schema in cancer cells.

V. DETAILED DESCRIPTION

Unless defined otherwise, all technical and scientific terms used herein have the same meaning as commonly understood by one of ordinary skill in the art. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agent(s), after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. Subjects with familial history of a disease are potential candidates for preventive regimens in certain embodiments. In addition, subjects who have a history of recurring symptoms are also potential candidates for prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, "amelioration" of the symptoms of a particular disorder by administration of a particular pharmaceutical composition refers to any lessening, whether permanent or temporary, lasting or transient, that can be attributed to or associated with administration of the composition.

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptoms associated with the disease or disorder. A "therapeutically effective amount" and "effective amount" of a compound mean an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, the terms "cancer" and "cancerous" refer to or describe the physiological condition in mammals that is typically characterized by unregulated cell growth. Examples of cancer include, but are not limited to blood-borne (e.g., lymphoma, leukemia) and solid tumors.

As used herein, and unless otherwise specified, the term "proliferative" disorder or disease refers to unwanted cell proliferation of one or more subset of cells in a multicellular organism resulting in harm (i.e., discomfort or decreased life expectancy) to the multicellular organism. For example, as used herein, proliferative disorder or disease includes neoplastic disorders and other proliferative disorders.

As used herein, and unless otherwise specified, the term "relapsed" refers to a situation where a subject, that has had a remission of cancer after a therapy, has a return of cancer cells.

As used herein, and unless otherwise specified, the term "refractory" or "resistant" refers to a circumstance where a subject, even after intensive treatment, has residual cancer cells in the body.

As used herein, and unless otherwise specified, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

As used herein, and unless otherwise specified, the term "anti-cancer agent," "anticancer agent" or "cancer therapeutic agent" is meant to include anti-proliferative agents and chemotherapeutic agents, including, but not limited to, antimetabolites (e.g., 5-fluoro uracil, methotrexate, azacitidine, decitabine, fludarabine, cytarabine (also known as cytosine arabinoside or Ara-C), and high dose cytarabine), antimicrotubule agents (e.g., vinca alkaloids, such as vincristine and vinblastine; and taxanes, such as paclitaxel and docetaxel), alkylating agents (e.g., mechlorethamine, chlorambucil, cyclophosphamide, melphalan, ifosfamide, carmustine, busulfan, cyclophosphamide, dacarbazine, ifosfamide, and nitrosoureas, such as carmustine, lomustine, bischloroethylnitrosurea, and hydroxyurea), platinum agents (e.g., cisplatin, carboplatin, oxaliplatin, satraplatin (JM-216), and CI-973), anthracyclines (e.g., doxorubicin and daunorubicin), antitumor antibiotics (e.g., mitomycin, bleomycin, idarubicin, adriamycin, daunomycin (also known as daunorubicin, rubidomycin, or cerubidine), and mitoxantrone), topoisomerase inhibitors (e.g., etoposide and camptothecins), purine antagonists or pyrimidine antagonists (e.g., 6-mercaptopurine, 5-fluorouracil, cytarabine, clofarabine, and gemcitabine), cell maturing agents (e.g., arsenic trioxide and tretinoin), DNA repair enzyme inhibitors (e.g., podophyllotoxines, etoposide, irinotecan, topotecan, and teniposide), enzymes that prevent cell survival (e.g., asparaginase and pegaspargase), histone deacetylase inhibitors (e.g., vorinostat), any other cytotoxic agents (e.g., estramustine phosphate, dexamethasone, prednimustine, and procarbazine), hormones (e.g., dexamethasone, prednisone, methylprednisolone, tamoxifen, leuprolide, flutamide, and megestrol), monoclonal antibodies (e.g., gemtuzumab ozogamicin, alemtuzumab, rituximab, and yttrium-90-ibritumomab tiuxetan), immuno-modulators (e.g., thalidomide and lenalidomide), Bcr-Abl kinase inhibitors (e.g., AP23464, AZD0530, CGP76030, PD180970, SKI-606, imatinib, BMS354825 (dasatinib), AMN107 (nilotinib), and VX-680), hormone agonists or antagonists, partial agonists or partial antagonists, kinase inhibitors, surgery, radiotherapy (e.g., gamma-radiation, neutron bean radiotherapy, electron beam radiotherapy, proton therapy, brachytherapy, and systemic radioactive isotopes), endocrine therapy, biological response modifiers (e.g., interferons, interleukins, and tumor necrosis factor), hyperthermia and cryotherapy, and agents to attenuate any adverse effects (e.g., antiemetics).

As used herein, and unless otherwise specified, the terms "co-administration" and "in combination with" include the administration of two or more therapeutic agents simultaneously, concurrently, or sequentially within no specific time limits unless otherwise indicated. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The terms "composition," "formulation," and "dosage form," as used herein are intended to encompass compositions comprising the specified ingredient(s) (in the specified amounts, if indicated), as well as any product(s) which result, directly or indirectly, from combination of the specified ingredient(s) in the specified amount(s). By "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof. Unless indicated otherwise, the terms "composition," "formulation," and "dosage form" are used herein interchangeably.

The term "immediate release," when used herein in reference to a composition, formulation, or dosage form provided herein, means that the composition, formulation, or dosage form does not comprise a component (e.g., a coating) that serves to delay the spatial and/or temporal release of some or all of the API from the composition, formulation, or dosage form following oral administration. In certain embodiments, an immediate release composition, formulation, or dosage form is one that releases the API substantially in the stomach following oral administration. In certain embodiments, an immediate release composition, formulation, or dosage form is one that releases the API substantially in the stomach or the upper intestine following oral administration. In specific embodiments, an immediate release composition, formulation, or dosage form is one that is not delayed-release. In specific embodiments, an immediate release composition, formulation, or dosage form is one that does not comprise an enteric coating.

The term "non-enteric-coated," when used herein, refers to a pharmaceutical composition, formulation, or dosage form that does not comprise a coating intended to release the active ingredient(s) beyond the stomach (e.g., in the intestine). In certain embodiments, a non-enteric-coated composition, formulation, or dosage form is designed to release the active ingredient(s) substantially in the stomach. In certain embodiments, a non-enteric-coated composition, formulation, or dosage form is designed to release the active ingredient(s) substantially in the stomach and the upper intestine.

The term "substantially in the stomach," when used herein in reference to a composition, formulation, or dosage form provided herein, means that at least about 99%, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, or at least about 10% of the cytidine analog is released in the stomach. The term "released in the stomach" and related terms as used herein refer to the process whereby the cytidine analog is made available for uptake by or transport across cells lining the stomach and then made available to the body.

The term "isotopic composition" refers to the amount of each isotope present in a given atomic position, and "natural isotopic composition" refers to the naturally occurring isotopic composition or abundance for a given atomic position. Atomic positions containing their natural isotopic composition may also be referred to herein as "non-enriched." Unless otherwise designated, the atomic positions of the compounds recited herein are meant to represent any stable isotope of that atom. For example, unless otherwise stated, when a position is designated specifically as "H" or "hydrogen," the position is understood to have hydrogen at its natural isotopic composition.

The term "isotopically enriched" refers to an atomic position having an isotopic composition other than the natural isotopic composition of that atom. "Isotopically enriched" may also refer to a compound containing at least one atomic position having an isotopic composition other than the natural isotopic composition of that atom. As used herein, an "isotopologue" is an isotopically enriched compound.

The term "isotopic enrichment" refers to the percentage of incorporation of an amount of a specific isotope at a given atomic position in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%.

The term "isotopic enrichment factor" refers to the ratio between the isotopic composition and the natural isotopic composition of a specified isotope.

With regard to the compounds provided herein, when a particular atomic position is designated as having deuterium or "D," it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000 (30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

The isotopic enrichment and isotopic enrichment factor of the compounds provided herein can be determined using conventional analytical methods known to one of ordinary skill in the art, including, e.g., mass spectrometry, nuclear magnetic resonance spectroscopy, and crystallography.

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as, e.g., a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. In one embodiment, by "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof. See, e.g., Remington, *The Science and Practice of Pharmacy,* 21st Edition; Lippincott Williams & Wilkins: Philadelphia, Pa., 2005; *Handbook of Pharmaceutical Excipients,* 5th Edition; Rowe et al., ed., The Pharmaceutical Press and the American Pharmaceutical Association: 2005; and *Handbook of Pharmaceutical Additives,* 3rd Edition; Ash and Ash ed., Gower Publishing Company: 2007; *Pharmaceutical Preformulation and Formulation,* Gibson ed., CRC Press LLC: Boca Raton, Fla., 2004.

As used herein, and unless otherwise specified, the term "hydrate" means a compound provided herein or a salt thereof, which further includes a stoichiometric or non-stoichiometric amount of water bound by non-covalent intermolecular forces.

As used herein, and unless otherwise specified, the term "solvate" means a solvate formed from the association of one or more solvent molecules to a compound provided herein. The term "solvate" includes hydrates (e.g., mono-hydrate, dihydrate, trihydrate, tetrahydrate and the like).

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

B. Cytidine Analogs

1. Overview

Provided herein are dosage forms, pharmaceutical formulations, and compositions comprising cytidine analogs that release the API substantially in the stomach upon oral administration. In certain embodiments, the cytidine analog is 5-azacytidine. In certain embodiments, the cytidine analog is 5-aza-2'-deoxycytidine (decitabine or 5-aza-CdR). In certain embodiments, the cytidine analog is, for example: 1-β-D-arabinofuranosylcytosine (Cytarabine or ara-C); pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxy-carbonyl-5'-deoxy-5-fluorocytidine (Capecitabine); $N^4$-octadecyl-cytarabine; elaidic acid cytarabine; or a conjugated compound comprising a cytidine analog and a fatty acid (e.g., an azacitidine-fatty acid conjugate, including, but not limited to, CP-4200 (Clavis Pharma ASA) or a compound disclosed in WO 2009/042767, such as aza-C-5'-petroselinic acid ester or aza-C-5'-petroselaidic acid ester).

In certain embodiments, cytidine analogs provided herein include esterified derivatives of cytidine analogs, such as, e.g., esterified derivatives of 5-azacytidine. In particular embodiments, esterified derivatives are cytidine analogs that contain an ester moiety (e.g., an acetyl group) at one or more positions on the cytidine analog molecule. Esterified derivatives may be prepared by any method known in the art. In certain embodiments, esterified derivatives of a cytidine analog serve as prodrugs of the cytidine analog, such that, e.g., following administration of an esterified derivative, the derivative is deacetylated in vivo to yield the cytidine analog. A particular embodiment herein provides 2',3',5'-triacetyl-5-azacytidine (TAC), which possesses favorable physical-chemical and therapeutic properties. See, e.g., International Publication No. WO 2008/092127 (International Application No. PCT/US2008/052124); Ziemba, A. J., et al., "Development of Oral Demethylating Agents for the Treatment of Myelodysplastic Syndrome" (Abstract No. 3369), In: *Proceedings of the 100th Annual Meeting of the American Association for Cancer Research;* 2009 Apr. 18-22; Denver, Co. Philadelphia (PA): AACR; 2009 (both of which are incorporated by reference herein in their entireties).

In certain embodiments, the cytidine analogs provided herein include any compound which is structurally related to cytidine or deoxycytidine and functionally mimics and/or antagonizes the action of cytidine or deoxycytidine. Certain embodiments herein provide salts, cocrystals, solvates (e.g., hydrates), complexes, prodrugs, precursors, metabolites, and/or other derivatives of the cytidine analogs provided herein. For example, particular embodiments provide salts, cocrystals, solvates (e.g., hydrates), complexes, precursors, metabolites, and/or other derivatives of 5-azacytidine. Certain embodiments provide cytidine analogs that are not salts, cocrystals, solvates (e.g., hydrates), or complexes of the cytidine analogs provided herein. For example, particular embodiments provide 5-azacytidine in a non-ionized, non-solvated (e.g., anhydrous), non-complexed form. Certain embodiments herein provide mixtures of two or more cytidine analogs provided herein.

Cytidine analogs provided herein may be prepared using synthetic methods and procedures referenced herein or otherwise available in the literature. For example, particular methods for synthesizing 5-azacytidine are taught in, e.g., U.S. Pat. No. 7,038,038 and references discussed therein, each of which is incorporated herein by reference. 5-Azacytidine is also available from Celgene Corporation, Warren, N.J. Other cytidine analogs provided herein may be prepared using previously disclosed synthetic procedures available to a person of ordinary skill in the art.

It should be noted that if there is a discrepancy between a depicted structure and a chemical name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers. Where the compound provided herein contains an alkenyl or alkenylene group, the compound may exist as one geometric (i.e., cis/trans or E/Z) isomer or a mixture of geometric (i.e., cis/trans or E/Z) isomers. Unless otherwise specified, a compound provided herein is intended to encompass all geometric isomers.

Where structural isomers are inter-convertible, the compound may exist as a single tautomer or a mixture of tautomers. This can take the form of proton tautomerism in the compound that contains, for example, an imino, keto, or oxime group; or so-called valence tautomerism in the compound that contain, for example, an aromatic moiety. It follows that a single compound may exhibit more than one type of isomerism. It will be understood that unless otherwise specified, a compound provided herein is intended to encompass all possible tautomers. Similarly, unless otherwise specified, a compound provided herein is intended to encompass all possible stereoisomers.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. Conventional techniques for the preparation/isolation of individual enantiomers include synthesis from a suitable optically pure precursor, asymmetric synthesis from achiral starting materials, or resolution of an enantiomeric mixture, for example, by chiral chromatography, recrystallization, resolution, diastereomeric salt formation, or derivatization into diastereomeric adducts followed by separation. In some instances, for compounds that undergo epimerization in vivo, one of skill in the art will recognize that administration of a compound in its (R) form is equivalent to administration of the compound in its (S) form, and vice versa.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of a compound provided herein, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In certain embodiments, exemplary cytidine analogs have the structures provided below:

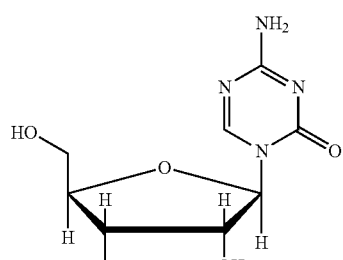

Azacitidine

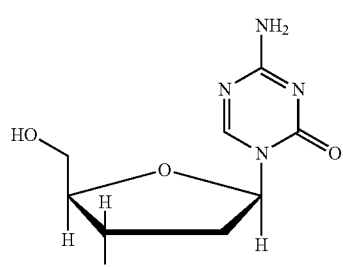

Decitabine

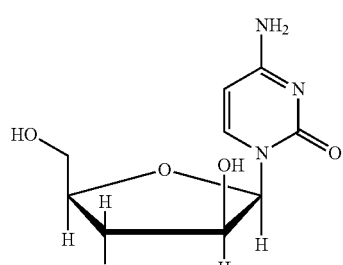

Cytarabine (Ara-C)

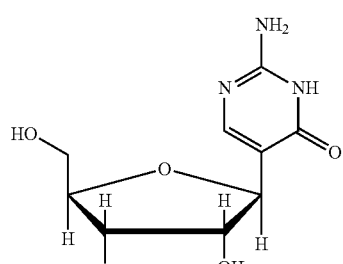

Pseudoisocytidine (psi ICR)

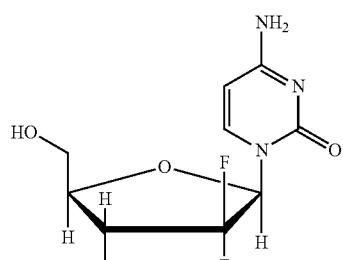

Gemcitabine

-continued

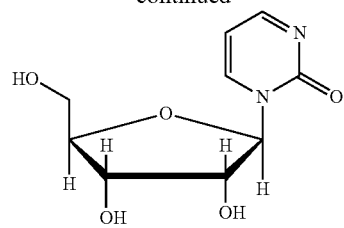

Zebularine

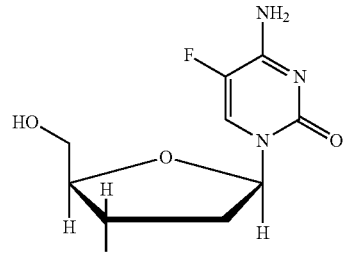

FCdR

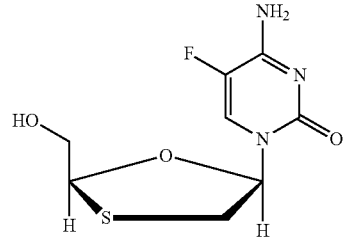

Emtriva

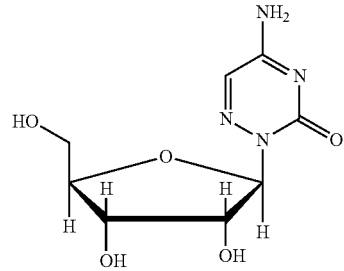

6-Azacytidine

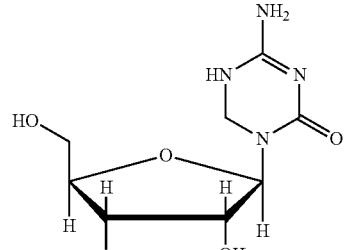

5-6-Dihydro-5-azacytidine

2. Isotopically Enriched Cytidine Analogs

Particular embodiments herein provide isotopically enriched cytidine analogs, prodrugs thereof, synthetic intermediates thereof, and metabolites thereof. For example, specific embodiments herein provide isotopically enriched 5-azacytidine.

Isotopic enrichment (e.g., deuteration) of pharmaceuticals to improve pharmacokinetics ("PK"), pharmacodynamics ("PD"), and toxicity profiles, has been demonstrated previously with some classes of drugs. See, e.g., Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade, D., Chem. Biol. Interact. 117: 191 (1999).

Without being limited by any particular theory, isotopic enrichment of a drug can be used, for example, to: (1) reduce or eliminate unwanted metabolites; (2) increase the half-life of the parent drug; (3) decrease the number of doses needed to achieve a desired effect; (4) decrease the amount of a dose necessary to achieve a desired effect; (5) increase the formation of active metabolites, if any are formed; and/or (6) decrease the production of deleterious metabolites in specific tissues and/or create a more effective drug and/or a safer drug for combination therapy, whether the combination therapy is intentional or not.

Replacement of an atom for one of its isotopes may often result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). See, e.g., Foster et al., Adv. Drug Res., vol. 14, pp. 1-36 (1985); Kushner et al., Can. J. Physiol. Pharmacol., vol. 77, pp. 79-88 (1999).

Certain embodiments herein provide deuterium enriched 5-azacytidine analogs, wherein one or more hydrogen(s) in the 5-azacytidine molecule is/are isotopically enriched with deuterium. In certain embodiments, provided herein are compounds of formula (I):

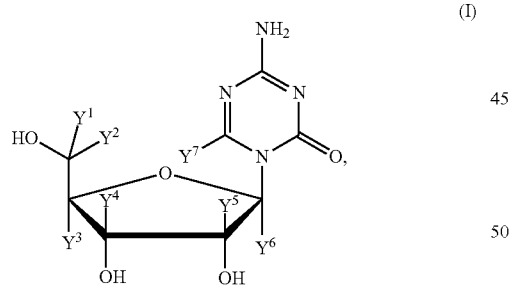

(I)

wherein one or more Y atom(s) (i.e., $Y^1$, $Y^2$, $Y^3$, $Y^4$, $Y^5$, $Y^6$, and $Y^7$) is/are hydrogen(s) isotopically enriched with deuterium, and any remaining Y atom(s) is/are non-enriched hydrogen atom(s). In particular embodiments, one, two, three, four, five, six, or seven of the indicated Y atom(s) is/are isotopically enriched with deuterium, and any remaining Y atom(s) is/are non-enriched hydrogen(s).

In certain embodiments, one or more Y atoms on the ribose moiety of Compound (I) are deuterium-enriched. Particular examples include, but are not limited to, the following compounds, in which the label "D" indicates a deuterium-enriched atomic position, i.e., a sample comprising the given compound has a deuterium enrichment at the indicated position(s) above the natural abundance of deuterium:

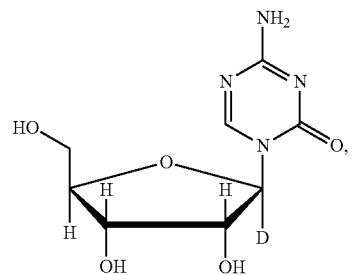

I-1

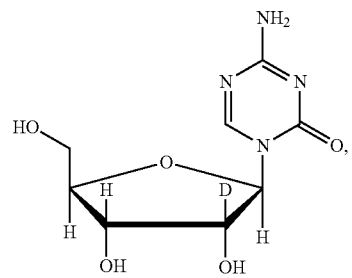

I-2

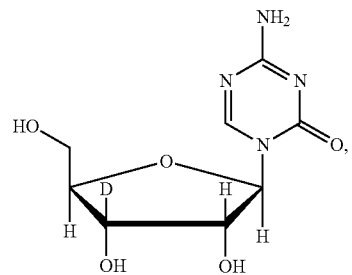

I-3

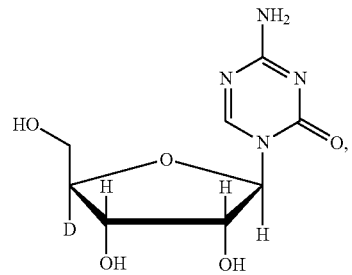

I-4

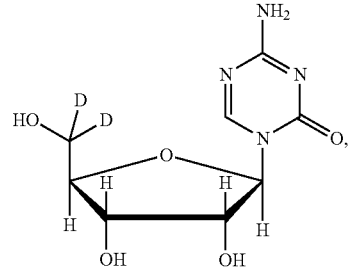

I-5

-continued

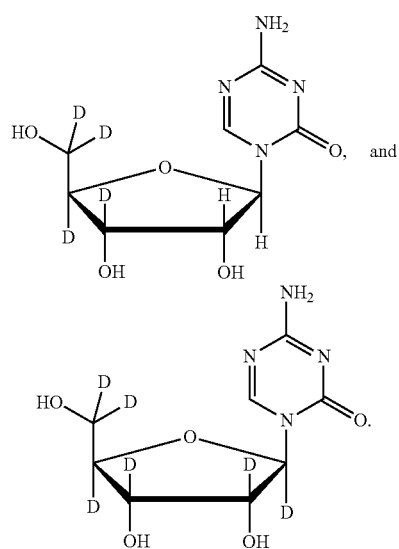

I-6

I-7

In certain embodiments, the Y atom on the 5-azacytosine moiety of Compound (I) is deuterium-enriched. Particular example includes the following compound, in which the label "D" indicates a deuterium-enriched atomic position, i.e., a sample comprising the given compound has a deuterium enrichment at the indicated position(s) above the natural abundance of deuterium:

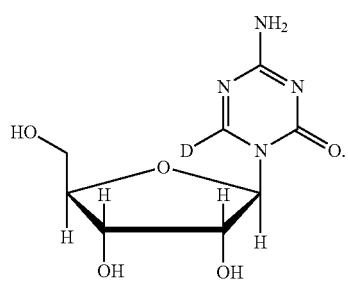

I-8

In certain embodiments, one or more Y atoms on the ribose moiety and the Y atom on the 5-azacytosine moiety of Compound (I) are deuterium-enriched. Particular examples include, but are not limited to, the following compounds, in which the label "D" indicates a deuterium-enriched atomic position, i.e., a sample comprising the given compound has a deuterium enrichment at the indicated position(s) above the natural abundance of deuterium:

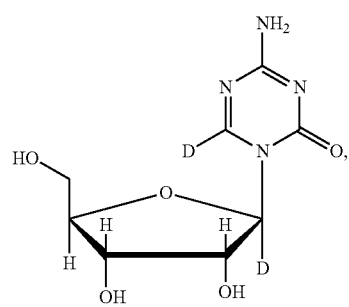

I-9

-continued

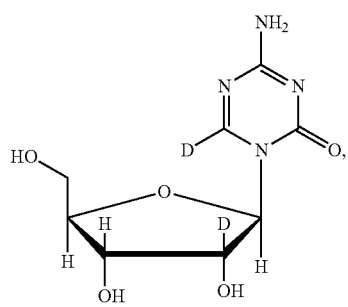

I-10

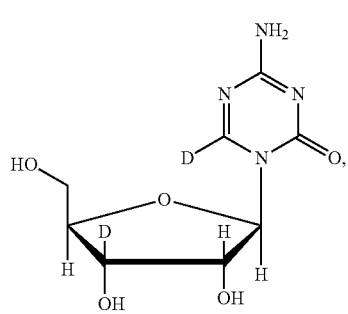

I-11

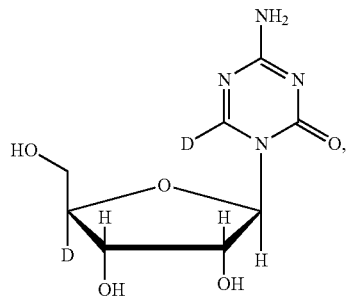

I-12

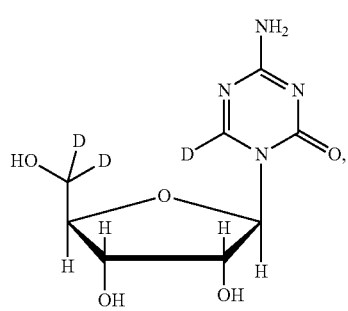

I-13

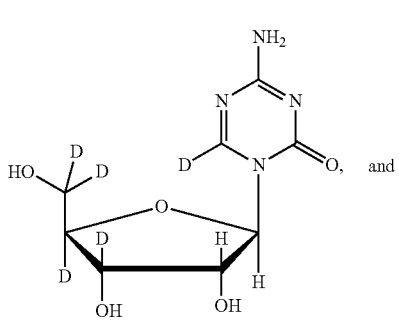

I-14

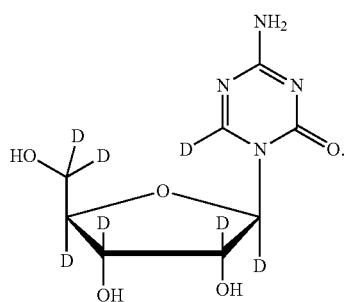

I-15

It is understood that one or more deuterium(s) may exchange with hydrogen under physiological conditions.

Certain embodiments herein provide carbon-13 enriched analogs of 5-azacytidine, wherein one or more carbon(s) in the 5-azacytidine molecule is/are isotopically enriched with carbon-13. In certain embodiments, provided herein are compounds of formula (II):

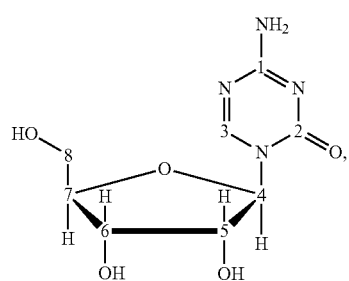

(II)

wherein one or more of 1, 2, 3, 4, 5, 6, 7, or 8 is/are carbon atom(s) isotopically enriched with carbon-13, and any remaining atom(s) of 1, 2, 3, 4, 5, 6, 7, or 8 is/are non-enriched carbon atom(s). In particular embodiments, one, two, three, four, five, six, seven, or eight carbon atom(s) (i.e., atoms 1, 2, 3, 4, 5, 6, 7, and 8) is/are isotopically enriched with carbon-13, and any remaining carbon atom(s) is/are non-enriched.

In certain embodiments, one or more carbon atom(s) of the ribose moiety of Compound (II) are enriched with carbon-13. Particular examples include, but are not limited to, the following compounds, in which the asterisk ("*") indicates a carbon-13 enriched atomic position, i.e., a sample comprising the given compound has a carbon-13 enrichment at the indicated position(s) above the natural abundance of carbon-13:

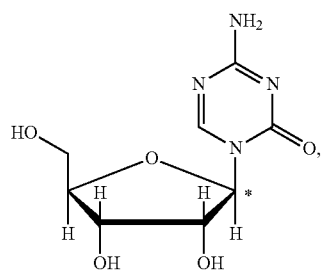

II-1

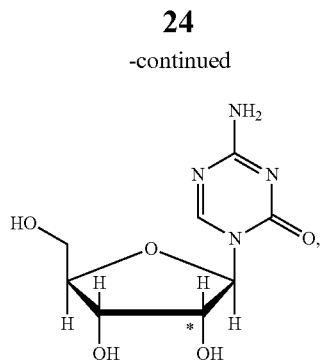

II-2

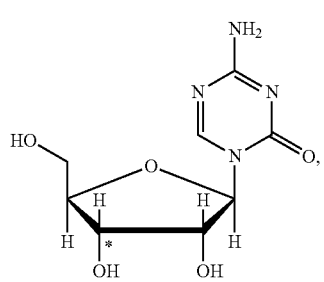

II-3

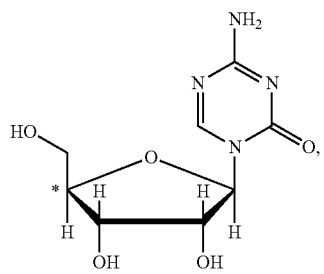

II-4

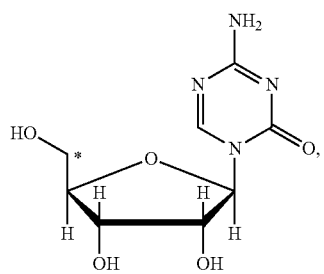

II-5

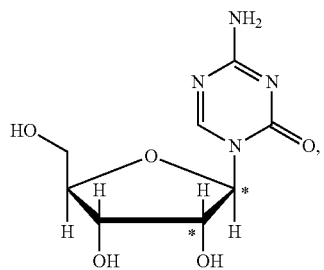

II-6

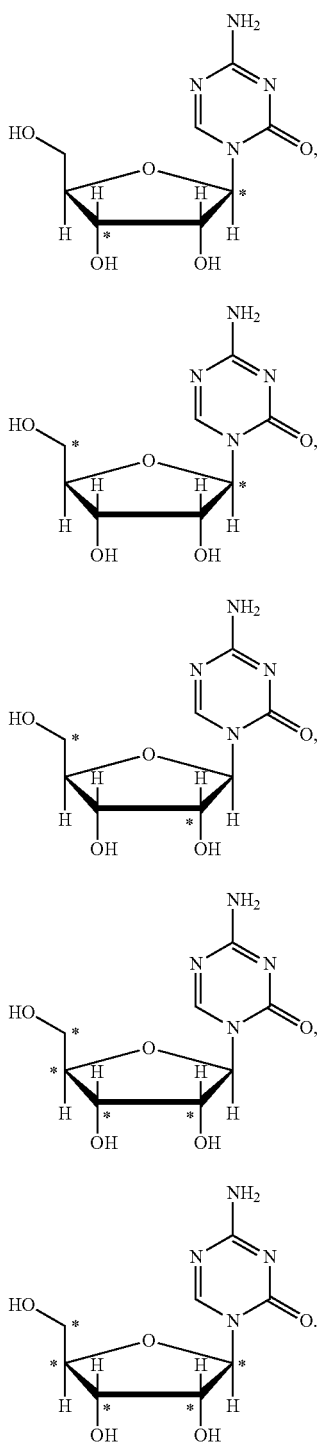
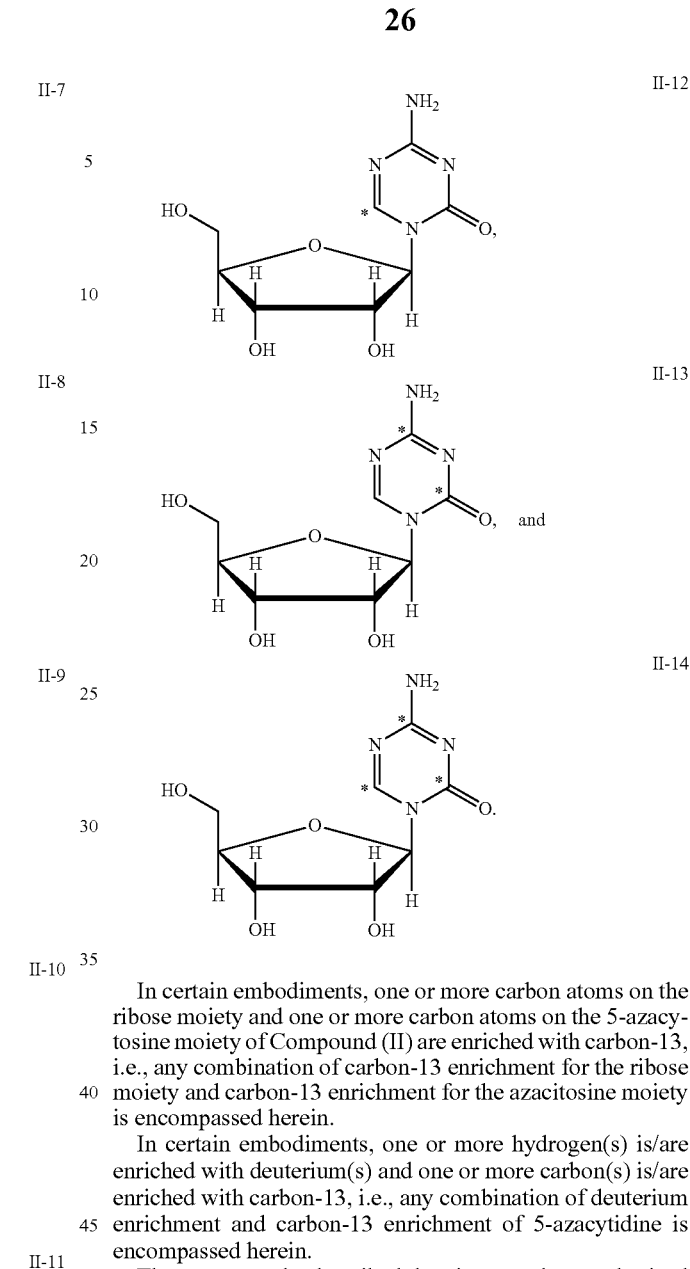

In certain embodiments, one or more carbon atom(s) of the 5-azacytosine moiety of Compound (II) are enriched with carbon-13. Particular examples include, but are not limited to, the following compounds, in which the asterisk "*" indicates a carbon-13 enriched atomic position, i.e., a sample comprising the given compound has a carbon-13 enrichment at the indicated position(s) above the natural abundance of carbon-13:

In certain embodiments, one or more carbon atoms on the ribose moiety and one or more carbon atoms on the 5-azacytosine moiety of Compound (II) are enriched with carbon-13, i.e., any combination of carbon-13 enrichment for the ribose moiety and carbon-13 enrichment for the azacitosine moiety is encompassed herein.

In certain embodiments, one or more hydrogen(s) is/are enriched with deuterium(s) and one or more carbon(s) is/are enriched with carbon-13, i.e., any combination of deuterium enrichment and carbon-13 enrichment of 5-azacytidine is encompassed herein.

The compounds described herein may be synthesized using any method known to one of ordinary skill in the art. For example, particular compounds described herein are synthesized using standard synthetic organic chemistry techniques known to those of ordinary skill in the art. In some embodiments, known procedures for the synthesis of 5-azacytidine are employed, wherein one or more of the reagents, starting materials, precursors, or intermediates are replaced by one or more isotopically-enriched reagents, starting materials, precursors, or intermediates, including but not limited to one or more deuterium-enriched reagents, starting materials, precursors, or intermediates, and/or one or more carbon-13-enriched reagents, starting materials, precursors, or intermediates. Isotopically enriched reagents, starting materials, precursors, or intermediates are commercially available or may be prepared by routine chemical reactions known to one of skill in the art. In some embodiments, the routes are based on those disclosed in U.S. Pat. No. 7,038,038 and U.S. Patent Publication No. 2009/0286752 (application Ser. No. 12/466,213), both of which are incorporated herein by reference in their entireties.

C. Pharmaceutical Compositions

In one embodiment, provided herein are pharmaceutical compositions, which comprise a cytidine analog, or a pharmaceutically acceptable salt, solvate, or hydrate thereof, as an active ingredient, in combination with one or more pharmaceutically acceptable excipient or carrier. In one embodiment, the pharmaceutical composition comprises at least one non-release controlling excipient or carrier. In one embodiment, the pharmaceutical composition comprises at least one release controlling and at least one nonrelease controlling excipient or carrier.

In certain embodiments, the cytidine analog used in the pharmaceutical compositions provided herein is in a solid form. Suitable solid forms include, but are not limited to, solid forms comprising the free base of the cytidine analog, and solid forms comprising salts of the cytidine analog. In certain embodiments, solid forms provided herein include polymorphs, solvates (including hydrates), and cocrystals comprising the cytidine analog and/or salts thereof. In certain embodiments, the solid form is a crystal form of the cytidine analog, or a pharmaceutically acceptable salt, solvate, or hydrate thereof.

In one embodiment, the pharmaceutical compositions provided herein may be formulated in various dosage forms for oral, parenteral, and topical administration. The pharmaceutical compositions may also be formulated as modified release dosage forms, including delayed-, extended-, prolonged-, sustained-, pulsed-, controlled-, accelerated- and fast-, targeted-, programmed-release, and gastric retention dosage forms. These dosage forms can be prepared according to conventional methods and techniques known to those skilled in the art. See, e.g., Remington, *The Science and Practice of Pharmacy*, 21st Edition; Lippincott Williams & Wilkins: Philadelphia, Pa., 2005; Modified-Release Drug Delivery Technology, Rathbone et al., eds., Drugs and the Pharmaceutical Science, Marcel Dekker, Inc.: New York, N.Y., 2003; Vol. 126.

In one embodiment, the pharmaceutical compositions are provided in a dosage form for oral administration. In another embodiment, the pharmaceutical compositions are provided in a dosage form for parenteral administration. In yet another embodiment, the pharmaceutical compositions are provided in a dosage form for topical administration.

In one embodiment, the pharmaceutical compositions provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

In one embodiment, the pharmaceutical compositions provided herein may be administered once or multiple times, at particular intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

1. Overview of Oral Dosage Forms

In one embodiment, the pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

In one embodiment, provided herein are pharmaceutical formulations and compositions comprising a cytidine analog (e.g., 5-azacytidine or another cytidine analog provided herein), and optionally a permeation enhancer, wherein the formulations and compositions are prepared for oral administration. In a particular embodiment, the formulations and compositions are prepared for release of the cytidine analog substantially in the stomach. In specific embodiments, the cytidine analog (e.g., 5-azacytidine or another cytidine analog provided herein) and the pharmaceutical formulation and composition are used for treating, preventing, or managing diseases and disorders associated with abnormal cell proliferation, for example, a solid tumor, wherein the cytidine analog, the formulation and composition are prepared for oral administration, preferably for release of the cytidine analog substantially in the stomach. Particular embodiments relate to the use of one or more cytidine analogs (e.g., 5-azacytidine or another cytidine analog provided herein) for the preparation of pharmaceutical formulations and compositions for treating particular medical indications, as provided herein. The pharmaceutical formulations and compositions comprising a cytidine analog provided herein are intended for oral delivery of the cytidine analog in subjects in need thereof. Oral delivery formats include, but are not limited to, tablets, capsules, caplets, solutions, suspensions, and syrups, and may also comprise a plurality of granules, beads, powders or pellets that may or may not be encapsulated. Such formats may also be referred to herein as the "drug core" which contains the cytidine analog.

Particular embodiments herein provide solid oral dosage forms that are tablets or capsules. In certain embodiments, the formulation is a tablet comprising a cytidine analog. In certain embodiments, the formulation is a capsule comprising a cytidine analog. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the API, e.g., substantially in the stomach. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the stomach. In certain embodiments, the formulation is a rapidly disintegrating tablet that dissolves substantially in the mouth following administration. In certain embodiments, embodiments herein encompass the use of a cytidine analog (e.g., 5-azacytidine or another cytidine analog provided herein) for the preparation of a pharmaceutical composition for treating a disease associated with abnormal cell proliferation, wherein the composition is prepared for oral administration.

2. Performance of Certain Dosage Forms Provided Herein

In certain embodiments, the formulations comprising a cytidine analog, such as, for example, 5-azacytidine or another cytidine analog provided herein, effect an immediate release of the API upon oral administration. In particular embodiments, the formulations comprising a cytidine analog, such as, for example, 5-azacytidine or another cytidine analog provided herein, comprise a therapeutically or prophylactically effective amount of the cytidine analog (and, optionally, one or more excipients) and effect an immediate release of the API upon oral administration.

In certain embodiments, the formulations comprising a cytidine analog, such as, for example, 5-azacytidine or another cytidine analog provided herein, effect a controlled release of the API substantially in the stomach upon oral administration. In certain embodiments, the formulations comprising a cytidine analog, such as, for example, 5-azacytidine or another cytidine analog provided herein, comprise a therapeutically or prophylactically effective amount of the cytidine analog and a drug release controlling component which is capable of releasing the cytidine analog substantially in the stomach. In certain embodiments, matrices (e.g., polymer matrices) may be employed in the formulation to control the release of the cytidine analog. In certain embodiments, coatings and/or shells may be employed in the formulation to control the release of the cytidine analog in the substantially in the stomach.

In certain embodiments, the formulations comprising a cytidine analog, such as, for example, 5-azacytidine or another cytidine analog provided herein, release the API substantially in the stomach upon oral administration. In certain embodiments, the formulations effect an immediate release of the cytidine analog upon oral administration. In certain embodiments, the formulations optionally further comprises a drug release controlling component, wherein the drug release controlling component is adjusted such that the release of the cytidine analog occurs substantially in the stomach. In particular embodiments, the drug release controlling component is adjusted such that the release of the cytidine analog is immediate and occurs substantially in the stomach. In particular embodiments, the drug release controlling component is adjusted such that the release of the cytidine analog is sustained and occurs substantially in the stomach. In certain embodiments, the formulation of a cytidine analog, such as, for example, 5-azacytidine or another cytidine analog provided herein, releases the API substantially in the stomach, and, subsequently, releases the remainder of the API in the intestine upon oral administration.

Methods by which skilled practitioners can assess where a drug is released in the gastrointestinal tract of a subject are known in the art, and include, for example, scintigraphic studies, testing in a bio-relevant medium which simulates the fluid in relevant portions of the gastrointestinal tract, among other methods.

Particular embodiments herein provide pharmaceutical formulations (e.g., immediate release oral formulations and/or formulations that release the API substantially in the stomach) comprising a cytidine analog (e.g., 5-azacytidine or another cytidine analog provided herein) that achieve a particular exposure in the subject to which the formulation is orally administered, as compared to a SC dose of the same cytidine analog. Particular embodiments provide oral formulations that achieve an exposure of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%, as compared to a SC dose.

In certain embodiments, the formulation (e.g., immediate release oral formulation and/or formulation that release the API substantially in the stomach) comprising a cytidine analog, such as, for example, 5-azacytidine or another cytidine analog provided herein, renders a certain percentage of the cytidine analog in the formulation systemically bioavailable upon oral administration. In certain embodiments, after the subject is orally administered the formulation, the cytidine analog in the formulation is absorbed substantially in the stomach, and becomes available to the body through systemic exposure. In particular embodiments, the oral bioavailability of a formulation comprising a cytidine analog provided herein is, e.g., greater than about 1%, greater than about 5%, greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, or about 100%, of the total amount of the cytidine analog in the formulation.

Methods by which skilled practitioners can assess the oral bioavailability of a drug formulation in a subject are known in the art. Such methods, include, for example, comparing certain dosing-related parameters, such as, but not limited to, maximum plasma concentration ("Cmax"), time to maximum plasma concentration ("Tmax"), or area-under-the-curve ("AUC") determinations.

Particular embodiments herein provide pharmaceutical formulations (e.g., immediate release oral formulations and/or formulations that release the API substantially in the stomach) comprising a cytidine analog (e.g., 5-azacytidine or another cytidine analog provided herein) that achieve a particular AUC value (e.g., AUC(0–t) or AUC(0–∞)) in the subject (e.g., human) to which the formulation is orally administered. Particular embodiments provide oral formulations that achieve an AUC value of at least about 25 ng-hr/mL, at least about 50 ng-hr/mL, at least about 75 ng-hr/mL, at least about 100 ng-hr/mL, at least about 150 ng-hr/mL, at least about 200 ng-hr/mL, at least about 250 ng-hr/mL, at least about 300 ng-hr/mL, at least about 350 ng-hr/mL, at least about 400 ng-hr/mL, at least about 450 ng-hr/mL, at least about 500 ng-hr/mL, at least about 550 ng-hr/mL, at least about 600 ng-hr/mL, at least about 650 ng-hr/mL, at least about 700 ng-hr/mL, at least about 750 ng-hr/mL, at least about 800 ng-hr/mL, at least about 850 ng-hr/mL, at least about 900 ng-hr/mL, at least about 950 ng-hr/mL, at least about 1000 ng-hr/mL, at least about 1100 ng-hr/mL, at least about 1200 ng-hr/mL, at least about 1300 ng-hr/mL, at least about 1400 ng-hr/mL, at least about 1500 ng-hr/mL, at least about 1600 ng-hr/mL, at least about 1700 ng-hr/mL, at least about 1800 ng-hr/mL, at least about 1900 ng-hr/mL, at least about 2000 ng-hr/mL, at least about 2250 ng-hr/mL, or at least about 2500 ng-hr/mL. In particular embodiments, the AUC determination is obtained from a time-concentration pharmacokinetic profile obtained from the blood samples of animals or human volunteers following dosing.

Particular embodiments herein provide pharmaceutical formulations (e.g., immediate release oral formulations and/or formulations that release the API substantially in the stomach) comprising a cytidine analog (e.g., 5-azacytidine or another cytidine analog provided herein) that achieve a particular maximum plasma concentration ("Cmax") in the subject to which the formulation is orally administered. Particular embodiments provide oral formulations that achieve a Cmax of the cytidine analog of at least about 25 ng/mL, at least about 50 ng/mL, at least about 75 ng/mL, at least about 100 ng/mL, at least about 150 ng/mL, at least about 200 ng/mL, at least about 250 ng/mL, at least about 300 ng/mL, at least about 350 ng/mL, at least about 400 ng/mL, at least about 450 ng/mL, at least about 500 ng/mL, at least about 550 ng/mL, at least about 600 ng/mL, at least about 650 ng/mL, at least about 700 ng/mL, at least about 750 ng/mL, at least about 800 ng/mL, at least about 850 ng/mL, at least about 900 ng/mL, at least about 950 ng/mL, at least about 1000 ng/mL, at least about 1100 ng/mL, at least about 1200 ng/mL, at least about 1300 ng/mL, at least about 1400 ng/mL, at least about 1500 ng/mL, at least about 1600 ng/mL, at least about 1700 ng/mL, at least about 1800 ng/mL, at least about 1900 ng/mL, at least about 2000 ng/mL, at least about 2250 ng/mL, or at least about 2500 ng/mL.

Particular embodiments herein provide pharmaceutical formulations (e.g., immediate release oral formulations and/or formulations that release the API substantially in the stomach) comprising a cytidine analog (e.g., 5-azacytidine or another cytidine analog provided herein) that achieve a particular time to maximum plasma concentration ("Tmax") in the subject to which the formulation is orally administered. Particular embodiments provide oral formulations that achieve a Tmax of the cytidine analog of less than about 10 min., less than about 15 min., less than about 20 min., less than about 25 min., less than about 30 min., less than about 35 min., less than about 40 min., less than about 45 min., less than about 50 min., less than about 55 min., less than about 60 min., less than about 65 min., less than about 70 min., less than about 75 min., less than about 80 min., less than about 85 min., less than about 90 min., less than about 95 min., less than about 100 min., less than about 105 min., less than about 110 min., less than about 115 min., less than about 120 min., less than about 130 min., less than about 140 min., less than about 150 min., less than about 160 min., less than about 170 min., less than about 180 min., less than about 190 min., less than about 200 min., less than about 210 min., less than about 220 min., less than about 230 min., or less than about 240 min. In particular embodiments, the Tmax value is measured from the time at which the formulation is orally administered.

Particular embodiments herein provide oral dosage forms comprising a cytidine analog, wherein the oral dosage forms have an enteric coating. Particular embodiments provide a permeable or partly permeable (e.g., "leaky") enteric coating with pores. In particular embodiments, the permeable or partly permeable enteric-coated tablet releases the 5-azacytidine in an immediate release manner substantially in the stomach.

3. Compositions of Certain Dosage Forms Provided Herein

Provided herein are dosage forms designed to maximize the absorption and/or efficacious delivery of certain cytidine analogs, e.g., 5-azacytidine or other cytidine analogs provided herein, upon oral administration, e.g., for release substantially in the stomach. Accordingly, certain embodiments herein provide a solid oral dosage form of a cytidine analog, such as, for example, 5-azacytidine or another cytidine analog provided herein, using pharmaceutical excipients designed for immediate release of the API upon oral administration, e.g., substantially in the stomach. Particular immediate release formulations comprise a specific amount of a cytidine analog and optionally one or more excipients. In certain embodiments, the formulation may be an immediate release tablet or an immediate release capsule (such as, e.g., an HPMC capsule).

Provided herein are methods of making the formulations provided herein comprising a cytidine analog provided herein (e.g., immediate release oral formulations and/or formulations that release the API substantially in the stomach). In particular embodiments, the formulations provided herein may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PREFORMULATION AND FORMULATION, CRC Press (2001).

In particular embodiments, formulations provided herein (e.g., immediate release oral formulations, formulations that release the API substantially in the stomach, or rapidly disintegrating formulations that dissolve substantially in the mouth) comprise a cytidine analog, such as, for example, 5-azacytidine or another cytidine analog provided herein, in a specific amount. In particular embodiments, the specific amount of the cytidine analog in the formulation is, e.g., about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 120 mg, about 140 mg, about 150 mg, about 160 mg, about 180 mg, about 200 mg, about 220 mg, least about 240 mg, about 250 mg, about 260 mg, about 280 mg, about 300 mg, about 320 mg, about 340 mg, about 350 mg, about 360 mg, about 380 mg, about 400 mg, about 420 mg, about 440 mg, about 450 mg, about 460 mg, about 480 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 3000 mg, about 4000 mg, or about 5000 mg. In particular embodiments, the specific amount of the cytidine analog in the formulation is, e.g., at least about 10 mg, at least about 20 mg, at least about 40 mg, at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 250 mg, at least about 260 mg, at least about 280 mg, at least about 300 mg, at least about 320 mg, at least about 340 mg, at least about 350 mg, at least about 360 mg, at least about 380 mg, at least about 400 mg, at least about 420 mg, at least about 440 mg, at least about 450 mg, at least about 460 mg, at least about 480 mg, at least about 500 mg, at least about 550 mg, at least about 600 mg, at least about 650 mg, at least about 700 mg, at least about 750 mg, at least about 800 mg, at least about 900 mg, at least about 1000 mg, at least about 1100 mg, at least about 1200 mg, at least about 1300 mg, at least about 1400 mg, at least about 1500 mg, at least about 1600 mg, at least about 1700 mg, at least about 1800 mg, at least about 1900 mg, at least about 2000 mg, at least about 2100 mg, at least about 2200 mg, at least about 2300 mg, at least about 2400 mg, at least about 2500 mg, at least about 3000 mg, at least about 4000 mg, or at least about 5000 mg.

In certain embodiments, the formulation is a tablet, wherein the tablet is manufactured using standard, art-recognized tablet processing procedures and equipment. In certain embodiments, the method for forming the tablets is direct compression of a powdered, crystalline and/or granular composition comprising the cytidine analog, alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the formulation is a capsule, wherein the capsules may be manufactured using standard, art-recognized capsule processing procedures and equipments. In certain embodiments, soft gelatin capsules may be prepared in which the capsules contain a mixture of the cytidine analog and vegetable oil or non-aqueous, water miscible materials such as, for example, polyethylene glycol and the like. In certain embodiments, hard gelatin capsules may be prepared containing granules of the cytidine analog in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In certain embodiments, the formulation of the cytidine analog, such as, for example, 5-azacytidine or another cytidine analog provided herein, is prepared using aqueous solvents without causing significant hydrolytic degradation of the cytidine analog. In particular embodiments, the formulation of the cytidine analog, such as, for example, 5-azacytidine or another cytidine analog provided herein, is a tablet which contains a coating applied to the drug core using aqueous solvents without causing significant hydrolytic degradation of the cytidine analog in the formulation. In certain embodiments, water is employed as the solvent for coating the drug core. In certain embodiments, the oral dosage form of the cytidine analog is a tablet containing a film coat applied to the drug core using aqueous solvents. In particular embodiments, water is employed as the solvent for film-coating. In particular embodiments, the tablet containing the cytidine analog is film-coated using aqueous solvents without effecting degradation of the pharmaceutical composition. In particular embodiments, water is used as the film coating solvent without effecting degradation of the pharmaceutical composition. In particular embodiments, an oral dosage form comprising 5-azacytidine and an aqueous film coating effects immediate drug release upon oral delivery. In particular embodiments, the oral dosage form comprising 5-azacytidine and an aqueous film coating effects controlled drug release to the upper gastrointestinal tract, e.g., the stomach, upon oral administration. In particular embodiments, a tablet with an aqueous-based film coating comprises 5-azacytidine as the API.

In certain embodiments, provided herein is a controlled release pharmaceutical formulation for oral administration of a cytidine analog that releases the cytidine analog substantially in the stomach, comprising: a) a specific amount of a cytidine analog; b) a drug release controlling component for controlling the release of the cytidine analog substantially in the upper gastrointestinal tract, e.g., the stomach; and c) optionally one or more excipients. In certain embodiments, the oral dosage form comprising the cytidine analog is prepared as a controlled release tablet or capsule which includes a drug core comprising the pharmaceutical composition and optional excipients. Optionally, a "seal coat" or "shell" is applied. In certain embodiments, a formulation provided herein comprising a cytidine analog provided herein is a controlled release tablet or capsule, which comprises a therapeutically effective amount of the cytidine analog, a drug release controlling component that controls the release of the cytidine analog substantially in the stomach upon oral administration, and optionally, one or more excipients.

Particular embodiments provide a drug release controlling component that is a polymer matrix, which swells upon exposure to gastric fluid to effect the gastric retention of the formulation and the sustained release of the cytidine analog from the polymer matrix substantially in the stomach. In certain embodiments, such formulations may be prepared by incorporating the cytidine analog into a suitable polymeric matrix during formulation. Examples of such formulations are known in the art. See, e.g., Shell et al., U.S. Patent Publication No. 2002/0051820 (application Ser. No. 09/990,061); Shell et al., U.S. Patent Publication No. 2003/0039688 (application Ser. No. 10/045,823); Gusler et al., U.S. Patent Publication No. 2003/0104053 (application Ser. No. 10/029,134), each of which is incorporated herein by reference in its entirety.

In certain embodiments, the drug release controlling component may comprise a shell surrounding the drug-containing core, wherein the shell releases the cytidine analog from the core by, e.g., permitting diffusion of the cytidine analog from the core and promoting gastric retention of the formulation by swelling upon exposure to gastric fluids to a size that is retained in the stomach. In certain embodiments, such formulations may be prepared by first compressing a mixture of the cytidine analog and one or more excipients to form a drug core, and compressing another powdered mixture over the drug core to form the shell, or enclosing the drug core with a capsule shell made of suitable materials. Examples of such formulations are known in the art. See, e.g., Berner et al., U.S. Patent Publication No. 2003/0104062 application Ser. No. 10/213,823), incorporated herein by reference in its entirety.

Certain embodiments herein provide oral dosage forms comprising a cytidine analog, wherein the dosage form contains pores in the conventional enteric coating. In particular embodiments, the oral dosage form of the cytidine analog is a tablet that contains a permeable or partly permeable (e.g., "leaky") enteric coating with pores. In particular embodiments, the permeable or partly permeable enteric-coated tablet controls the release of the cytidine analog from the tablet primarily to the upper gastrointestinal tract, e.g., the stomach. In particular embodiments, the permeable or partly permeable enteric-coated tablet comprises 5-azacytidine. In particular embodiments, the remainder of the cytidine analog is subsequently released beyond the stomach (e.g., in the intestine).

In certain embodiments, the pharmaceutical formulation provided herein is a compressed tablet comprising a cytidine analog. In addition to the cytidine analog, the tablet optionally comprises one or more excipients, including (a) diluents or fillers, which may add necessary bulk to a formulation to prepare tablets of the desired size; (b) binders or adhesives, which may promote adhesion of the particles of the formulation, enabling a granulation to be prepared and maintaining the integrity of the final tablet; (c) disintegrants or disintegrating agents, which, after administration, may promote breakup of the tablets to smaller particles for improved drug availability; (d) anti-adherents, glidants, lubricants or lubricating agents, which may enhance flow of the tableting material into the tablet dies, minimize wear of the punches and dies, prevent the sticking of fill material to the punches and dies, and produce tablets having a sheen; and (e) miscellaneous adjuncts such as colorants and flavorants. After compression, tablets provided herein may be coated with various materials as described herein.

In certain embodiments, the pharmaceutical formulation provided herein is a multiple compressed tablet of a cytidine analog. Multiple compressed tablets are prepared by subjecting the fill material to more than a single compression. The result may be a multiple-layered tablet or a tablet-within-a-tablet, the inner tablet being the core comprising a cytidine analog and optionally one or more excipients, and the outer portion being the shell, wherein the shell comprises one or more excipients, and may or may not contain the cytidine analog. Layered tablets may be prepared by the initial compaction of a portion of fill material in a die followed by additional fill material and compression to form two- or three-layered tablets, depending upon the number of separate fills. Each layer may contain a different therapeutic agent, separate from one another for reasons of chemical or physical incompatibility, or the same therapeutic agent for staged drug release, or simply for the unique appearance of the multiple-layered tablet. Each portion of fill may be colored differently to prepare a distinctive looking tablet. In the preparation of tablets having a compressed tablet as the inner core, special machines may be used to place the preformed tablet precisely within the die for the subsequent compression of surrounding fill material.

In certain embodiments, the compressed tablet of a cytidine analog may be coated with a colored or an uncolored sugar layer. The coating may be water-soluble and quickly dissolved after oral ingestion. The sugar coating may serve the purpose of protecting the enclosed drug from the environment and providing a barrier to an objectionable taste or smell. The sugar coating may also enhance the appearance of the compressed tablet and permit the imprinting of identifying manufacturer's information. In certain embodiments, sugar-coated tablets may be 50% larger and heavier than the original uncoated tablets. The sugar-coating of tablets may be divided into the following optional steps: (1) waterproofing and sealing (if needed); (2) sub-coating; (3) smoothing and final rounding; (4) finishing and coloring (if desired); (5) imprinting (if needed); and (6) polishing.

In certain embodiments, the compressed tablet of a cytidine analog may be film-coated. Film-coated tablets may be compressed tablets coated with a thin layer of a polymer capable of forming a skin-like film over the tablet. The film is usually colored and has the advantage to be more durable, less bulky, and less time-consuming to apply. By its composition, the coating may be designed to rupture and expose the core tablet at the desired location within the gastrointestinal tract. The film-coating process, which places a thin skin-tight coating of a plastic-like material over the compressed tablet, may produce coated tablets having essentially the same weight, shape, and size as the originally compressed tablet. The film-coating may be colored to make the tablets attractive and distinctive. Film-coating solutions may be non-aqueous or aqueous. In particular embodiments, the non-aqueous solutions may optionally contain one or more of the following types of materials to provide the desired coating to the tablets: (1) a film former capable of producing smooth, thin films reproducible under conventional coating conditions and applicable to a variety of tablet shapes, such as, for example, cellulose acetate phthalate; (2) an alloying substance providing water solubility or permeability to the film to ensure penetration by body fluids and therapeutic availability of the drug, such as, for example, polyethylene glycol; (3) a plasticizer to produce flexibility and elasticity of the coating and thus provide durability, such as, for example, castor oil; (4) a surfactant to enhance spreadability of the film during application, such as, for example, polyoxyethylene sorbitan derivatives; (5) opaquants and colorants to make the appearance of the coated tablets attractive and distinctive, such as, for example, titanium dioxide as an opaquant, and FD&C or D&C dyes as a colorant; (6) sweeteners, flavors, or aromas to enhance the acceptability of the tablet to the subject, such as, for example, saccharin as sweeteners, and vanillin as flavors and aromas; (7) a glossant to provide a luster to the tablets without a separate polishing operation, such as, for example, beeswax; and (8) a volatile solvent to allow the spread of the other components over the tablets while allowing rapid evaporation to permit an effective yet speedy operation, such as, for example, alcohol-acetone mixture. In certain embodiments, an aqueous film-coating formulation may contain one or more of the following: (1) film-forming polymer, such as, for example, cellulose ether polymers as hydroxypropyl methyl-cellulose, hydroxypropyl cellulose, and methyl-cellulose; (2) plasticizer, such as, for example, glycerin, propylene glycol, polyethylene glycol, diethyl phthalate, and dibutyl subacetate; (3) colorant and opacifier, such as, for example, FD&C or D&C lakes and iron oxide pigments; or (4) vehicle, such as, for example, water.

In certain embodiments, the compressed tablet of a cytidine analog may be compression-coated. The coating material, in the form of a granulation or powder, may be compressed onto a tablet core of drug with a special tablet press.

In certain embodiments, the pharmaceutical formulation is a gelatin-coated tablet comprising a cytidine analog. A gelatin-coated tablet is a capsule-shaped compressed tablet that allows the coated product to be smaller than a capsule filled with an equivalent amount of powder. The gelatin coating facilitates swallowing and compared to unsealed capsules, gelatin-coated tablets may be more tamper-evident.

In certain embodiments, the pharmaceutical formulation may be a sublingual tablet of a cytidine analog. The sublingual tablet is intended to be dissolved beneath the tongue for absorption through the oral mucosa. The sublingual tablet may dissolve promptly and provide rapid release of the drug.

In certain embodiments, the pharmaceutical formulation is an immediate release tablet of a cytidine analog. In certain embodiments, the immediate release tablet is designed, e.g., to disintegrate and release the API absent of any special rate-controlling features, such as special coatings and other techniques. In certain embodiments, the formulation is a rapidly disintegrating tablet that, e.g., dissolves substantially in the mouth following administration. In certain embodiments, the pharmaceutical formulation is an extended release tablet of a cytidine analog. In certain embodiments, the extended release tablet is designed, e.g., to release the API over an extended period of time and substantially in the stomach.

In certain embodiments, compressed tablets may be prepared by wet granulation. Wet granulation is a widely employed method for the production of compressed tablets, and, in particular embodiments, requires one or more the following steps: (1) weighing and blending the ingredients; (2) preparing a damp mass; (3) screening the damp mass into pellets or granules; (4) drying the granulation; (5) sizing the granulation by dry screening; (6) adding lubricant and blending; and (7) tableting by compression.

In certain embodiments, compressed tablets may be prepared by dry granulation. By the dry granulation method, the powder mixture is compacted in large pieces and subsequently broken down or sized into granules. But this method, either the active ingredient or the diluent has cohesive property. After weighing and mixing the ingredients, the powder mixture may be slugged or compressed into large flat tablets or pellets. The slugs then are broken up by hand or by a mill and passed through a screen of desired mesh for sizing. Lubricant is added in the usual manner, and tablets are prepared by compression. Alternatively, instead of slugging, powder compactors may be used to increase the density of a powder by pressing it between high-pressure rollers. The compressed material then is broken up, sized, and lubricated, and tablets are prepared by compression in the usual manner. The roller compaction method is often preferred over slugging. Binding agents used in roller compaction formulations include methylcellulose or hydroxyl-methylcellulose and can produce good tablet hardness and friability.

In certain embodiments, compressed tablets may be prepared by direct compression. Some granular chemicals possess free flowing and cohesive properties that enable them to be compressed directly in a tablet machine without the need of wet or dry granulation. For chemicals that do not possess this quality, special pharmaceutical excipients may be used which impart the necessary qualities for the production of tablets by direct compression. Particular tableting excipients include, e.g.: fillers, such as spray-dried lactose, micro-crystals of alpha-monohydrate lactose, sucrose-invert sugar-corn starch mixtures, micro-crystalline cellulose, crystalline maltose, and di-calcium phosphate; disintegrating agents, such as direct-compression starch, sodium carboxymethyl starch, cross-linked carboxymethylcellulose fibers, and cross-linked polyvinylpyrrolidone; lubricants, such as magnesium searate and talc; and glidants, such as fumed silicon dioxide.

In certain embodiments, tablets provided herein may be prepared by molding. The base for molded tablets is generally a mixture of finely powdered lactose with or without a portion of powdered sucrose. In preparing the fill, the drug is mixed uniformly with the base by geometric dilution. The powder mixture may be wetted with a mixture of water and alcohol sufficient only to dampen the powder so that it may be compacted. The solvent action of the water on a portion of the lactose/sucrose base effects the biding of the powder mixture upon drying. The alcohol portion hastens the drying process.

In certain embodiments, the pharmaceutical formulations provided herein contain a cytidine analog and, optionally, one or more excipients to form a "drug core." Optional excipients include, e.g., diluents (bulking agents), lubricants, disintegrants, fillers, stabilizers, surfactants, preservatives, coloring agents, flavoring agents, binding agents, excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, formulations provided herein comprise one or more binders. Binders may be used, e.g., to impart cohesive qualities to a tablet, and thus ensure that the tablet remains intact after compression. Suitable binders include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropylmethylcellulose, methyl cellulose, ethyl cellulose, hydroxyethyl cellulose, carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, ceratonia, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein. The binding agent can be, relative to the drug core, in the amount of about 2% w/w of the drug core; about 4% w/w of the drug core, about 6% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, about 34% w/w of the drug core, about 36% w/w of the drug core, about 38% w/w of the drug core, about 40% w/w of the drug core, about 42% w/w of the drug core, about 44% w/w of the drug core, about 46% w/w of the drug core, about 48% w/w of the drug core, about 50% w/w of the drug core, about 52% w/w of the drug core, about 54% w/w of the drug core, about 56% w/w of the drug core, about 58% w/w of the drug core, about 60% w/w of the drug core, about 62% w/w of the drug core, about 64% w/w of the drug core, about 66% w/w of the drug core; about 68% w/w of the drug core, about 70% w/w of the drug core, about 72% w/w of the drug core, about 74% w/w of the drug core, about 76% w/w of the drug core, about 78% w/w of the drug core, about 80% w/w of the drug core, about 82% w/w of the drug core, about 84% w/w of the drug core, about 86% w/w of the drug core, about 88% w/w of the drug core, about 90% w/w of the drug core, about 92% w/w of the drug core, about 94% w/w of the drug core, about 96% w/w of the drug core, about 98% w/w of the drug core, or more, if determined to be appropriate. In certain embodiments, a suitable amount of a particular binder is determined by one of ordinary skill in the art.

In certain embodiments, formulations provided herein comprise one or more diluents. Diluents may be used, e.g., to increase bulk so that a practical size tablet is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethylacrylates, simethicone, sodium alginate, sodium chloride, sorbitol, starch, pregelatinized starch, sucrose, sulfobutylether-β-cyclodextrin, talc, tragacanth, trehalose, and xylitol. Diluents may be used in amounts calculated to obtain a desired volume for a tablet or capsule; in certain embodiments, a diluent is used in an amount of about 5% or more, about 10% or more, about 15% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 68% or more, about 70% or more, about 72% or more, about 74% or more, about 76% or more, about 78% or more, about 80% or more, about 85% or more, about 90% or more, or about 95% or more, weight/weight, of a drug core; between about 10% and about 90% w/w of the drug core; between about 20% and about 80% w/w of the drug core; between about 30% and about 70% w/w of the drug core; between about 40% and about 60% w/w of the drug core. In certain embodiments, a suitable amount of a particular diluent is determined by one of ordinary skill in the art.

In certain embodiments, formulations provided herein comprise one or more lubricants. Lubricants may be used, e.g., to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. In certain embodiments, stearates, if present, represent no more than approximately 2 weight % of the drug-containing core. Further examples of lubricants include, e.g., calcium stearate, glycerin monostearate, glyceryl behenate, glyceryl palmitostearate, magnesium lauryl sulfate, magnesium stearate, myristic acid, palmitic acid, poloxamer, polyethylene glycol, potassium benzoate, sodium benzoate, sodium chloride, sodium lauryl sulfate, sodium stearyl fumarate, stearic acid, talc, and zinc stearate. In particular embodiments, the lubricant is magnesium stearate. In certain embodiments, the lubricant is present, relative to the drug core, in an amount of about 0.2% w/w of the drug core, about 0.4% w/w of the drug core, about 0.6% w/w of the drug core, about 0.8% w/w of the drug core, about 1.0% w/w of the drug core, about 1.2% w/w of the drug core, about 1.4% w/w of the drug core, about 1.6% w/w of the drug core, about 1.8% w/w of the drug core, about 2.0% w/w of the drug core, about 2.2% w/w of the drug core, about 2.4% w/w of the drug core, about 2.6% w/w of the drug core, about 2.8% w/w of the drug core, about 3.0% w/w of the drug core, about 3.5% w/w of the drug core, about 4% w/w of the drug core, about 4.5% w/w of the drug core, about 5% w/w of the drug core, about 6% w/w of the drug core, about 7% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 25% w/w of the drug core, about 30% w/w of the drug core, about 35% w/w of the drug core, about 40% w/w of the drug core, between about 0.2% and about 10% w/w of the drug core, between about 0.5% and about 5% w/w of the drug core, or between about 1% and about 3% w/w of the drug core. In certain embodiments, a suitable amount of a particular lubricant is determined by one of ordinary skill in the art.

In certain embodiments, formulations provided herein comprise one or more disintegrants. Disintegrants may be used, e.g., to facilitate disintegration of the tablet, and may be, e.g., starches, clays, celluloses, algins, gums or crosslinked polymers. Disintegrants also include, e.g., alginic acid, carboxymethylcellulose calcium, carboxymethylcellulose sodium (e.g., AC-DI-SOL, PRIMELLOSE), colloidal silicon dioxide, croscarmellose sodium, crospovidone (e.g., KOLLIDON, POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB) and starch. Additional disintegrants include, e.g., calcium alginate, chitosan, sodium docusate, hydroxypropyl cellulose, and povidone. In certain embodiments, the disintegrant is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, greater than about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular disintegrant is determined by one of ordinary skill in the art.

In certain embodiments, formulations provided herein comprise one or more stabilizers. Stabilizers (also called absorption enhancers) may be used, e.g., to inhibit or retard drug decomposition reactions that include, by way of example, oxidative reactions. Stabilizing agents include, e.g., d-Alpha-tocopheryl polyethylene glycol 1000 succinate (Vitamin E TPGS), acacia, albumin, alginic acid, aluminum stearate, ammonium alginate, ascorbic acid, ascorbyl palmitate, bentonite, butylated hydroxytoluene, calcium alginate, calcium stearate, calcium carboxymethylcellulose, carrageenan, ceratonia, colloidal silicon dioxide, cyclodextrins, diethanolamine, edetates, ethylcellulose, ethyleneglycol palmitostearate, glycerin monostearate, guar gum, hydroxypropyl cellulose, hypromellose, invert sugar, lecithin, magnesium aluminum silicate, monoethanolamine, pectin, poloxamer, polyvinyl alcohol, potassium alginate, potassium polacrilin, povidone, propyl gallate, propylene glycol, propylene glycol alginate, raffinose, sodium acetate, sodium alginate, sodium borate, sodium carboxymethyl cellulose, sodium stearyl fumarate, sorbitol, stearyl alcohol, sufobutylb-cyclodextrin, trehalose, white wax, xanthan gum, xylitol, yellow wax, and zinc acetate. In certain embodiments, the stabilizer is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular stabilizer is determined by one of ordinary skill in the art.

In certain embodiments, formulations provided herein comprise one or more glidants. Glidants may be used, e.g., to improve the flow properties of a powder composition or granulate or to improve the accuracy of dosing. Excipients that may function as glidants include, e.g., colloidal silicon dioxide, magnesium trisilicate, powdered cellulose, starch, tribasic calcium phosphate, calcium silicate, powdered cellulose, colloidal silicon dioxide, magnesium silicate, magnesium trisilicate, silicon dioxide, starch, tribasic calcium phosphate, and talc. In certain embodiments, the glidant is, relative to the drug core, present in the amount of less than about 1% w/w of the drug core, about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular glidant is determined by one of ordinary skill in the art.

In one embodiment, formulations provided herein comprise one or more complexing agents. In certain embodiments, the complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In certain embodiments, formulations provided herein comprise one or more permeation enhancers (also called, e.g., permeability enhancers). In certain embodiments, the permeation enhancer enhances the uptake of a cytidine analog through the gastrointestinal wall (e.g., the stomach). In certain embodiments, the permeation enhancer alters the rate and/or amount of the cytidine analog that enters the bloodstream. In particular embodiments, d-alpha-tocopheryl polyethylene glycol-1000 succinate (Vitamin E TPGS) is used as a permeation enhancer. In particular embodiments, one or more other suitable permeation enhancers are used, including, e.g., any permeation enhancer known in the art. Specific examples of suitable permeation enhancers include, e.g., those listed below:

| Product name | Chemical Name | Example of Supplier |
|---|---|---|
| Pluronic F 127 | Poloxamer F 127 | Sigma |
| Lutrol F 68 | Poloxamer 188 | BASF |
| Carbopol 934-P | Carbomer 934-P | Spectrum Chemical |
| Tween 80 | Polysorbate 80 | Sigma |
| Chitosan | Chitosan Low Mol Wt | Aldrich |
| Capric acid/Na cap | Sodium Decanoate | Sigma |
| Lauric acid/Na laur | Sodium Dodecanoate | Sigma |
| Disodium EDTA | Ethylenediamine tetraacetic acid disodium dihydrate | Sigma |
| Propylene glycol | 1,2 Propanediol | Sigma |
| CM Cellulose | Carboxymethyl Cellulose | Sigma |
| Labrasol | Caprylocaproyl macrogol-8 glycerides | Gattefosse |
| N,N-Dimethylacetamide | (minimum 99%) | Sigma |
| Vitamin E TPGS | d-Alpha-Tocopheryl PolyethyleneGlycol-1000 Succinate | Eastman |
| Solutol HS 15 | Polyethylene glycol 660 12-hydroxystearate | BASF |
| Labrafil M 1944 CS (2) | Oleyl Macrogolglyerides | Gattefosse |

Other potential permeation enhancers include, e.g., alcohols, dimethyl sulfoxide, glyceryl monooleate, glycofurol, isopropyl myristate, isopropyl palmitate, lanolin, linoleic acid, myristic acid, oleic acid, oleyl alcohol, palmitic acid, polyoxyethylene alkyl ethers, 2-pyrrolidone, sodium lauryl sulfate, and thymol.

In certain embodiments, the permeation enhancer is present in the formulation in an amount by weight, relative to the total weight of the formulation, of about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1% about 4.2%, about 4.3%, about 4.4%, about 4.5%, about 4.6%, about 4.7%, about 4.8%, about 4.9%, about 5%, about 5.1% about 5.2%, about 5.3%, about 5.4%, about 5.5%, about 5.6%, about 5.7%, about 5.8%, about 5.9%, about 6%, about 6.1% about 6.2%, about 6.3%, about 6.4%, about 6.5%, about 6.6%, about 6.7%, about 6.8%, about 6.9%, about 7%, about 7.1% about 7.2%, about 7.3%, about 7.4%, about 7.5%, about 7.6%, about 7.7%, about 7.8%, about 7.9%, about 8%, about 8.1% about 8.2%, about 8.3%, about 8.4%, about 8.5%, about 8.6%, about 8.7%, about 8.8%, about 8.9%, about 9%, about 9.1% about 9.2%, about 9.3%, about 9.4%, about 9.5%, about 9.6%, about 9.7%, about 9.8%, about 9.9%, about 10%, greater than about 10%, greater than about 12%, greater than about 14%, greater than about 16%, greater than about 18%, greater than about 20%, greater than about 25%, greater than about 30%, greater than about 35%, greater than about 40%, greater than about 45%, or greater than about 50%. In certain embodiments, the appropriate amount of a suitable permeation enhancer provided herein is determined by one of skill in the art.

Without intending to be limited to any particular theory, the permeation enhancers provided herein may function by, inter alia, facilitating (e.g., increasing the rate or extent of) the transport of a cytidine analog through the gastrointestinal wall. In general, movement through the gastrointestinal wall may occur by, e.g.: passive diffusion, such as the movement of drug across a membrane in a manner driven solely by the concentration gradient; carrier-mediated diffusion, such as the movement of drug across a cell membrane via a specialized transport system embedded in the cell membrane; paracellular diffusion, such as the movement of a drug across a membrane by going between, rather than through, two cells; and transcellular diffusion, such as the movement of a drug across the cell. Additionally, there are numerous cellular proteins capable of preventing intracellular accumulation of drugs by pumping out drug that enters the cell. These are sometimes called efflux pumps. One such efflux pump is that involving p-glycoprotein, which is present in many different tissues in the body (e.g., intestine, placental membrane, blood-brain barrier). Permeation enhancers can function by, inter alia, facilitating any of the processes mentioned above (such as by increasing fluidity of membranes, opening tight junctions between cells, and/or inhibiting efflux, among others).

In certain embodiments, the compositions provided herein comprising a cytidine analog, e.g., 5-azacytidine or another cytidine analog provided herein, are essentially free of a cytidine deaminase inhibitor (e.g., do not comprise a cytidine deaminase inhibitor). In certain embodiments, the compositions provided herein are essentially free of (e.g., do not comprise) the cytidine deaminase inhibitor tetrahydrouridine (THU). Certain embodiments herein provide pharmaceutical compositions comprising a therapeutically effective amount of a cytidine analog (e.g., 5-azacytidine or another cytidine analog provided herein), wherein the compositions release the cytidine analog substantially in the stomach following oral administration to a subject, and wherein the compositions are essentially free of (e.g., do not comprise) a cytidine deaminase inhibitor (e.g., THU). Certain embodiments herein provide pharmaceutical compositions comprising a therapeutically effective amount of a cytidine analog (e.g., 5-azacytidine or another cytidine analog provided herein), wherein the compositions release the cytidine analog substantially in the stomach following oral administration to a subject, wherein the compositions are essentially free of (e.g., do not comprise) a cytidine deaminase inhibitor (e.g., THU), and wherein the compositions achieve a particular biological parameter provided herein (e.g., a particular Cmax value, Tmax value, and/or AUC value provided herein). In particular embodiments, a composition provided herein that is essentially free of a cytidine deaminase inhibitor (e.g., THU) comprises, e.g., less than 200 mg, less than 150 mg, less than 100 mg, less than 50 mg, less than 25 mg, less than 10 mg, less than 5 mg, less than 1 mg, or less than 0.1 mg of the cytidine deaminase inhibitor.

4. Other Embodiments of Oral Dosage Forms

In other embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. In one embodiment, enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. In one embodiment, film coating imparts the same general characteristics as sugar coating. Multiple compressed tablets are compressed tablets made by more than one compression cycle, including layered tablets, and press-coated or dry-coated tablets.

In one embodiment, the tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are useful in the formation of chewable tablets and lozenges.

In one embodiment, the pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In one embodiment, the pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

In one embodiment, other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

In one embodiment, the pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in the dosage forms provided herein.

In one embodiment, the pharmaceutical compositions provided herein may be formulated as immediate or modified release dosage forms, including delayed-, sustained-, pulsed-, controlled-, targeted-, and programmed-release forms.

In one embodiment, the pharmaceutical compositions provided herein may be co-formulated with other active ingredients which do not impair the desired therapeutic action, or with substances that supplement the desired action.

In one embodiment, active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5. Parenteral Dosage Forms

In another embodiment, the pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

In one embodiment, the pharmaceutical compositions provided herein may be formulated in dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington, *The Science and Practice of Pharmacy*, supra).

In one embodiment, the pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

In one embodiment, suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

In one embodiment, suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In one embodiment, the pharmaceutical compositions provided herein may be formulated for single or multiple dosage administration. The single dosage formulations are packaged in an ampoule, a vial, or a syringe. The multiple dosage parenteral formulations may contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

In one embodiment, the pharmaceutical compositions provided herein may be formulated as immediate or modified release dosage forms, including delayed-, sustained, pulsed-, controlled, targeted-, and programmed-release forms.

In one embodiment, the pharmaceutical compositions may be formulated as a suspension, solid, semi-solid, or thixotropic liquid, for administration as an implanted depot.

In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

In one embodiment, suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

In one embodiment, suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyloxyethanol copolymer, and ethylene/vinyl acetate/vinyl alcohol terpolymer.

In specific embodiments, provided herein is a pharmaceutical composition prepared for parenteral administration (e.g., IV or SC). In one embodiment, the composition comprises 5-azacytidine as a lyophilized powder. In one embodiment, the composition comprises 5-azacytidine and mannitol as a lyophilized powder. In one embodiment, the amount of 5-azacytidine in the composition is about 100 mg. In one embodiment, the weight ratio of 5-azacytidine to mannitol is about 1:1. In one embodiment, the lyophilized powder comprising 5-azacytidine is reconstituted with sterile water for IV or SC administration. In one embodiment, the dose for parenteral administration is about 75 mg/m$^2$. In one embodiment, the dose for parenteral administration is from about 75 mg/m$^2$ to about 100 mg/m$^2$. In specific embodiments, the composition is administered daily for 7 days at a dose of about 75 mg/m$^2$ to about 100 mg/m$^2$. In specific embodiments, the composition is administered daily for 7 days at a dose of about 75 mg/m$^2$ to about 100 mg/m$^2$, and the cycle is repeated every 4 weeks. In one embodiment, the compositions is administered for at least 4 to 6 cycles.

In some embodiments, azacitidine is administered at about 20-200 mg/kg per day (including for example 50 mg/kg, 80 mg/kg, 100 mg/kg, 120 mg/kg, 140 mg/kg, 180 mg/kg).

In some embodiments, decitabine is administered at about 0.75-4 mg/kg per day (including for example 1.0 mg/kg, 1.5 mg/kg, 2.00 mg/kg, 2.5 mg/kg, 3.0 mg/kg, 3.5 mg/kg).

In some embodiments, azacitidine or decitabine is administered at about 10-200 mg/m$^2$ (including for example about 50-100 mg/m$^2$ or for example about 75 mg/m$^2$).

6. Topical Dosage Forms

In yet another embodiment, the pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in, e.g., Remington, *The Science and Practice of Pharmacy*, supra.

In one embodiment, rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

In one embodiment, the pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

In one embodiment, solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

In one embodiment, the pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

In one embodiment, capsules, blisters and cartridges for use in an inhaler or insufflator may be formulated to contain a powder mix of the pharmaceutical compositions provided herein; a suitable powder base, such as lactose or starch; and a performance modifier, such as L-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

In one embodiment, the pharmaceutical compositions provided herein for topical administration may be formulated to be immediate release or modified release, including delayed-, sustained-, pulsed-, controlled-, targeted, and programmed release.

7. Additional Therapeutic Agents

In some embodiments, provided herein is a pharmaceutical composition comprising one, two, three, or more other pharmacologically active substances (also termed herein "additional therapeutic agents," "second active agents," or the like) (e.g., other than cytidine analog). In some embodiments, the cytidine analog formulations provided herein further comprise one, two, three, or more other pharmacologically active substances (also termed herein "additional therapeutic agents," "second active agents," or the like). In other embodiments, the cytidine analog formulations provided herein is co-administered with one, two, three, or more other pharmacologically active substances. In particular embodiments, the oral formulations provided herein comprise the additional therapeutic agent(s) in a therapeutically effective amount. In particular embodiments, the cytidine analog (e.g., 5-azacytidine or another cytidine analog provided herein) and the additional therapeutic agent(s) are co-formulated together in the same dosage form using methods of co-formulating active pharmaceutical ingredients, including methods disclosed herein and methods known in the art. In other embodiments, the cytidine analog (e.g., 5-azacytidine or another cytidine analog provided herein) and the additional therapeutic agent(s) are co-administered in separate dosage forms. It is believed that certain combinations work synergistically in the treatment of particular diseases or disorders, including, e.g., types of cancer and certain diseases and conditions associated with, or characterized by, undesired angiogenesis or abnormal cell proliferation, for example, solid tumors. Cytidine analog dosage forms provided herein can also work to alleviate adverse effects associated with certain second active agents, and some second active agents can be used to alleviate adverse effects associated with cytidine analog dosage forms provided herein. In certain embodiments, the formulations of cytidine analogs provided herein are co-administered with one or more therapeutic agents to provide a resensitization effect in subjects in need thereof. Additional therapeutic agents can be, e.g., large molecules (e.g., proteins) or small molecules (e.g., synthetic inorganic, organometallic, or organic molecules).

Examples of particular additional therapeutic agents useful in the compositions and methods disclosed herein include, but are not limited to, e.g., cytotoxic agents, anti-metabolites, antifolates, HDAC inhibitors (e.g., entinostat, also known as SNDX-275 or MS-275; or vorinostat, also known as suberoylanilide hydroxamic acid (SAHA) or N-hydroxy-N-phenyloctanediamide), DNA intercalating agents, DNA cross-linking agents, DNA alkylating agents, DNA cleaving agents, topoisomerase inhibitors, CDK inhibitors, JAK inhibitors, anti-angiogenic agents, Bcr-Abl inhibitors, HER2 inhibitors, EGFR inhibitors, VEGFR inhibitors, PDGFR inhibitors, HGFR inhibitors, IGFR inhibitors, c-Kit inhibitors, Ras pathway inhibitors, PI3K inhibitors, multi-targeted kinase inhibitors, mTOR inhibitors, anti-estrogens, anti-androgens, aromatase inhibitors, somatostatin analogs, ER modulators, anti-tubulin agents, vinca alkaloids, taxanes, HSP inhibitors, Smoothened antagonists, telomerase inhibitors, COX-2 inhibitors, anti-metastatic agents, immunosuppressants, biologics such as antibodies, and hormonal therapies. In particular embodiments, the co-administered therapeutic agent is an immunomodulatory compound, e.g., thalidomide, lenalidomide, or pomalidomide. In particular embodiments, the co-administered therapeutic agent is carboplatin. In particular embodiments, the co-administered therapeutic agent is paclitaxel (e.g., Abraxane®). See, e.g., U.S. Pat. Nos. 7,758,891, 7,771,751, 7,820,788, 7,923,536, 8,034,375; U.S. Patent Publication No. 2010/0048499; see also U.S. Pat. Nos. 5,916, 596; 6,506,405; 6,749,868, and 6,537,579, and U.S. Pat. Pub. Nos. 2007/0082838; all of which are incorporated herein by reference in their entireties. Other references include PCT Application Publication Nos. WO08/057,562, WO09/126, 938, WO09/126,401, WO09/126,175, incorporated herein by reference. In one embodiment, the co-administered agent may be dosed, e.g., orally or by injection.

In one embodiment, the additional therapeutic agent is a composition comprising nanoparticles comprising a taxane (such as paclitaxel) and a carrier protein. In some embodiments, the nanoparticle composition comprises nanoparticles comprising paclitaxel and an albumin. In some embodiments, the nanoparticles in the composition described herein have an average diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least about any one of 60%, 70%, 80%, 90%, 95%, or 99%) of all the nanoparticles in the composition have a diameter of no greater than about 200 nm, including for example no greater than about any one of 190, 180, 170, 160, 150, 140, 130, 120, 110, 100, 90, 80, 70, or 60 nm. In some embodiments, at least about 50% (for example at least any one of 60%, 70%, 80%, 90%, 95%, or 99%) of all the nanoparticles in the composition fall within the range of about 20 to about 400, including for example about 20 to about 200 nm, about 30 to about 180 nm, and any one of about 40 to about 150, about 50 to about 120, and about 60 to about 100 nm. In some embodiments, the carrier protein has sulfhydryl groups that can form disulfide bonds. In some embodiments, at least about 5% (including for example at least about any one of 10%, 15%, 20%, 25%, 30%, 40%, 50%, 60%, 70%, 80%, or 90%) of the carrier protein in the nanoparticle portion of the composition are crosslinked (for example crosslinked through one or more disulfide bonds).

In some embodiments, the nanoparticles comprise the taxane (such as paclitaxel) coated with a carrier protein, such as albumin (e.g., human serum albumin). In some embodiments, the composition comprises taxane in both nanoparticle and non-nanoparticle form, wherein at least about any one of 50%, 60%, 70%, 80%, 90%, 95%, or 99% of the taxane in the composition are in nanoparticle form. In some embodiments, the taxane in the nanoparticles constitutes more than about any one of 50%, 60%, 70%, 80%, 90%, 95%, or 99% of the nanoparticles by weight. In some embodiments, the nanoparticles comprise a core of taxane that is substantially free of polymeric materials (such as polymeric matrix).

In some embodiments, the nanoparticle composition is substantially free (such as free) of surfactants (such as Cremophor®, Tween 80, or other organic solvents used for the administration of taxanes). In some embodiments, the nanoparticle composition contains less than about any one of 20%, 15%, 10%, 7.5%, 5%, 2.5%, or 1% organic solvent. In some embodiments, the weight ratio of carrier protein (such as albumin) and taxane in the nanoparticle composition is about 18:1 or less, such as about 15:1 or less, for example about 9:1 or less. In some embodiments, the weight ratio of carrier protein (such as albumin) and taxane in the composition falls within the range of any one of about 1:1 to about 18:1, about 2:1 to about 15:1, about 3:1 to about 13:1, about 4:1 to about 12:1, about 5:1 to about 10:1, about 9:1. In some embodiments, the weight ratio of carrier protein and taxane in the nanoparticle portion of the composition is about any one of 1:2, 1:3, 1:4, 1:5, 1:9, 1:10, 1:15, or less.

In some embodiments, the particle composition comprises one or more of the above characteristics. In some embodiments, the nanoparticle composition is Abraxane®. Nanoparticle compositions comprising other taxanes (such as docetaxel and ortataxel) may also comprise one or more of the above characteristics.

In some embodiments, Abraxane® is intravenously administering at a dose of about 80 to about 200 mg/m² (such as about 100 mg/m²). In some embodiments, Abraxane® is administered weekly. In some embodiments, Abraxane® is administered once every two weeks. In some embodiments, Abraxane® is administered once every three weeks. In some embodiments, Abraxane® is administered as part of a cyclic treatment regimen (e.g., in cycles). In some embodiments, Abraxane® is administered on Days 1 and 8 of a 21-day cycle. In some embodiments, Abraxane® is administered on Days 8 and 15 of a 21-day cycle.

In some embodiment, carboplatin is intravenously administering at the dose of about AUC 2 to AUC 6 (such as AUC 2, AUC 4, AUC 6). In some embodiments, carboplatin is administered weekly. In some embodiments, carboplatin is administered once every two weeks. In some embodiments, carboplatin is administered once every three weeks. In some embodiments, carboplatin is administered as part of a cyclic treatment regimen (e.g., in cycles).

Other examples of additional therapeutic agents include, but are not limited to, hematopoietic growth factor, a cytokine, an anti-cancer agent, granulocyte colony-stimulating factor (G-CSF), granulocyte-macrophage colony-stimulating factor (GM-CSF), erythropoietin (EPO), interleukin (IL), interferon (IFN), oblimersen, melphalan, topotecan, pentoxifylline, taxotere, irinotecan, ciprofloxacin, doxorubicin, vincristine, dacarbazine, Ara-C, vinorelbine, prednisone, cyclophosphamide, bortezomib, arsenic trioxide. Such additional therapeutic agents are particularly useful in methods and compositions disclosed herein including, but not limited to, those relating to treatment of multiple myeloma.

Other examples of additional therapeutic agents include, but are not limited to, an antibody (e.g., rituximab, anti-CD33), hematopoietic growth factor, cytokine, anti-cancer agent, antibiotic, cox-2 inhibitor, immunomodulatory agent, immunosuppressive agent, corticosteroid, or a pharmacologically active mutant or derivative thereof. See, e.g., S, Nand et al., *Leukemia and Lymphoma,* 2008, 49(11):2141-47 (describing a Phase II study involving the administration of a combination of hydroxyurea, azacitidine and low dose gemtuzumab ozogamicin to elderly patients with AML and high-risk MDS, and concluding that this combination appears to be a safe and effective regimen in the treatment of AML and high risk MDS in this group of patients). Such additional therapeutic agents are particularly useful in methods and compositions disclosed herein including, but not limited to, those relating to treatment of the diseases and disorders disclosed herein.

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions provided herein include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Embodiments herein encompass the use of native, naturally occurring, and recombinant proteins. Particular embodiments encompass mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with oral formulations disclosed herein include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. Oral formulations disclosed herein can also comprise, be combined with, or used in combination with anti-TNF-α antibodies.

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits provided herein. See, e.g., Emens, L. A., et al., *Curr. Opinion Mol. Ther.* 3(1):77-84 (2001).

In one embodiment, the additional therapeutic agent (e.g., large-molecule compound or small-molecule compound) reduces, eliminates, or prevents an adverse effect associated with the administration (e.g., oral administration) of a cytidine analog provided herein. Depending on the particular cytidine analog and the disease or disorder begin treated, adverse effects can include, but are not limited to, anemia, neutropenia, febrile neutropenia, thrombocytopenia, hepatotoxicity (e.g., including, but not limited to, hepatoxicity in patients with preexisting hepatic impairment), elevated serum creatinine, renal failure, renal tubular acidosis, hypokalemia, hepatic coma, nausea, vomiting, dyspepsia, abdominal pain, pyrexia, leukopenia, diarrhea, constipation, ecchymosis, petechiae, rigors, weakness, pneumonia, anxiety, insomnia, lethargy, and decrease in weight, among others known in the art to be associated with particular cytidine analogs.

Like some large molecules, many small-molecule compounds are believed to be capable of providing a synergistic effect when administered with (e.g., before, after or simultaneously) a cytidine analog oral formulation disclosed herein. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol;

duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®)), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific additional therapeutic agents include, but are not limited to, oblimersen (Genasense), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacliataxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil), paclitaxel, ganciclovir, adriamycin, estramustine sodium phosphate (Emcyt®), sulindac, and etoposide.

8. Kits

In one embodiment, active ingredients provided herein are not administered to a patient at the same time or by the same route of administration. Provided herein are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

In one embodiment, kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

D. Methods of Use

In one embodiment, provided herein are methods for treating, preventing or managing cancer by administering a cytidine analog, or a pharmaceutically acceptable salt, solvate, or hydrate thereof, to a subject having cancer. In one embodiment, the methods comprise treating cancer with a cytidine analog, or a pharmaceutically acceptable salt, solvate, or hydrate thereof. In one embodiment, the methods comprise preventing cancer with a cytidine analog, or a pharmaceutically acceptable salt, solvate, or hydrate thereof. In one embodiment, the methods comprise managing cancer with a cytidine analog, or a pharmaceutically acceptable salt, solvate, or hydrate thereof. In certain embodiments, the cytidine analog is 5-azacytidine. In certain embodiments, the cytidine analog is decitabine. In certain embodiments, the methods comprise co-administering one or more additional active agents (e.g., an anti-cancer agent provided herein). In certain embodiments, the subject is a mammal. In certain embodiments, the subject is a human. In particular embodiments, the cancer is a solid tumor (e.g., a relapsed or refractory solid tumor).

In one embodiment, provided herein is use of a cytidine analog (e.g., 5-azacytidine or another cytidine analog provided herein), or a pharmaceutically acceptable salt, solvate, or hydrate thereof, in the manufacture of a medicament for the treatment, prevention, and/or management of cancer (e.g., a relapsed or refractory solid tumor).

In one embodiment, provided herein is a cytidine analog (e.g., 5-azacytidine or another cytidine analog provided herein), or a pharmaceutically acceptable salt, solvate, or hydrate thereof, for use in the treatment, prevention, and/or management of cancer (e.g., a relapsed or refractory solid tumor).

In one embodiment, provided herein are methods of treating, preventing, or managing certain types of cancer, including but not limited to, a solid tumor or a blood-borne tumor; a refractory cancer or a relapsed cancer; or a refractory solid tumor or a relapsed solid tumor. In one embodiment, provided herein are methods of treating, preventing, or managing certain types of cancer, including but not limited to, cancers of the breast, lung, head and neck, ovary, testicle, prostate, gastrointestinal system, stomach, pancreas, liver, colon, kidney, bladder, brain, skin, or bone. In other embodiments, the cancer is a cancer of the blood or the lymph.

In one embodiment, provided herein are methods of treating, preventing, or managing breast cancer, comprising administering a cytidine analog (e.g., orally) and at least one additional therapeutic agent (e.g., additional therapeutic agent described herein).

In one embodiment, provided herein are methods of treating, preventing, or managing lung cancer (e.g., NSCLC or SCLC), comprising administering a cytidine analog (e.g., orally) and at least one additional therapeutic agent (e.g., additional therapeutic agent described herein).

In one embodiment, provided herein are methods of treating, preventing, or managing head and neck cancer, comprising administering a cytidine analog (e.g., orally) and at least one additional therapeutic agent (e.g., additional therapeutic agent described herein).

In one embodiment, provided herein are methods of treating, preventing, or managing ovarian cancer, comprising administering a cytidine analog (e.g., orally) and at least one additional therapeutic agent (e.g., additional therapeutic agent described herein).

In one embodiment, provided herein are methods of treating, preventing, or managing testicular cancer, comprising administering a cytidine analog (e.g., orally) and at least one additional therapeutic agent (e.g., additional therapeutic agent described herein).

In one embodiment, provided herein are methods of treating, preventing, or managing prostate cancer, comprising administering a cytidine analog (e.g., orally) and at least one additional therapeutic agent (e.g., additional therapeutic agent described herein).

In one embodiment, provided herein are methods of treating, preventing, or managing gastrointestinal cancer, comprising administering a cytidine analog (e.g., orally) and at least one additional therapeutic agent (e.g., additional therapeutic agent described herein).

In one embodiment, provided herein are methods of treating, preventing, or managing stomach cancer, comprising administering a cytidine analog (e.g., orally) and at least one additional therapeutic agent (e.g., additional therapeutic agent described herein).

In one embodiment, provided herein are methods of treating, preventing, or managing pancreatic cancer, comprising administering a cytidine analog (e.g., orally) and at least one additional therapeutic agent (e.g., additional therapeutic agent described herein).

In one embodiment, provided herein are methods of treating, preventing, or managing liver cancer, comprising administering a cytidine analog (e.g., orally) and at least one additional therapeutic agent (e.g., additional therapeutic agent described herein).

In one embodiment, provided herein are methods of treating, preventing, or managing colorectal cancer, comprising administering a cytidine analog (e.g., orally) and at least one additional therapeutic agent (e.g., additional therapeutic agent described herein).

In one embodiment, provided herein are methods of treating, preventing, or managing renal cancer, comprising administering a cytidine analog (e.g., orally) and at least one additional therapeutic agent (e.g., additional therapeutic agent described herein).

In one embodiment, provided herein are methods of treating, preventing, or managing bladder cancer, comprising administering a cytidine analog (e.g., orally) and at least one additional therapeutic agent (e.g., additional therapeutic agent described herein).

In one embodiment, provided herein are methods of treating, preventing, or managing brain cancer, comprising administering a cytidine analog (e.g., orally) and at least one additional therapeutic agent (e.g., additional therapeutic agent described herein).

In one embodiment, provided herein are methods of treating, preventing, or managing skin cancer (e.g., melanoma), comprising administering a cytidine analog (e.g., orally) and at least one additional therapeutic agent (e.g., additional therapeutic agent described herein).

In one embodiment, provided herein are methods of treating, preventing, or managing bone cancer, comprising administering a cytidine analog (e.g., orally) and at least one additional therapeutic agent (e.g., additional therapeutic agent described herein).

In one embodiment, provided herein are methods of treating, preventing, or managing blood cancer, comprising administering a cytidine analog (e.g., orally) and at least one additional therapeutic agent (e.g., additional therapeutic agent described herein).

In one embodiment, provided herein are methods of treating, preventing, or managing leukemia, comprising administering a cytidine analog (e.g., orally) and at least one additional therapeutic agent (e.g., additional therapeutic agent described herein).

In one embodiment, provided herein are methods of treating, preventing, or managing lymphoma, comprising administering a cytidine analog (e.g., orally) and at least one additional therapeutic agent (e.g., additional therapeutic agent described herein).

In one embodiment, provided herein are methods of treating, preventing, or managing multiple myeloma, comprising administering a cytidine analog (e.g., orally) and at least one additional therapeutic agent (e.g., additional therapeutic agent described herein).

In one embodiment, provided herein are methods of treating, preventing, or managing myelodysplastic syndrome, comprising administering a cytidine analog (e.g., orally) and at least one additional therapeutic agent (e.g., additional therapeutic agent described herein).

In one embodiment, provided herein are methods of treating, preventing, or managing cancer in the primary tumor, lymph nodes, or distant metastasis, by administering a cytidine analog, or a pharmaceutically acceptable salt, solvate, or hydrate thereof, to a subject in need thereof. In one embodiment, provided herein are methods of treating, preventing, or managing cancer in the primary tumor, lymph nodes, or distant metastasis, by administering 5-azacytidine, or a pharmaceutically acceptable salt, solvate, or hydrate thereof, to a subject in need thereof.

In one embodiment, provided herein are methods of treating, preventing, or managing cancer in a subject having surgically resectable cancer, locally or regionally advanced cancer, or distant metastatic cancer, by administering a cytidine analog, or a pharmaceutically acceptable salt, solvate, or hydrate thereof. In one embodiment, provided herein are methods of treating, preventing, or managing cancer in a subject having surgically resectable cancer, locally or regionally advanced cancer, or distant metastatic cancer, by administering 5-azacytidine, or a pharmaceutically acceptable salt, solvate, or hydrate thereof. In particular embodiments, provided herein are methods of treating surgically resectable cancer, by administering 5-azacytidine to a subject having cancer. In particular embodiments, provided herein are methods of treating locally or regionally advanced cancer, by administering 5-azacytidine to a subject having cancer. In particular embodiments, provided herein are methods of treating distant metastatic cancer, by administering 5-azacytidine to a subject having cancer.

In one embodiment, the methods comprise treating, preventing or managing certain stages of cancer, e.g., Stage O, Stage I, Stage II, Stage III, and Stage IV, by administering a cytidine analog, or a pharmaceutically acceptable salt, solvate, or hydrate thereof, to a subject having cancer. The staging of cancer may be defined according to methods known in the art, for example, according to the guidelines provided by the American Joint Committee on Cancer (AJCC). In one embodiment, the staging of cancer is designated and grouped based on the TNM classification, i.e., a classification based on the status of primary tumor (e.g., TX, T0, T is, T1, T2, T3, T4), regional lymph nodes (e.g., NX, N0, N1, N2, N3), and/or distant metastasis (e.g., MX, M0, M1), in a subject having cancer.

In particular embodiments, methods provided herein comprise administering a cytidine analog to a subject having a solid tumor that is surgically resectable. In particular embodiments, the methods provided herein comprise administering a cytidine analog to a subject having locally advanced solid tumor. In particular embodiments, methods provided herein comprise administering a cytidine analog to a subject having regionally advanced solid tumor. In particular embodiments, the methods provided herein comprise administering a cytidine analog to a subject having a distant metastasis, e.g., at the time of diagnosis.

Particular embodiments provide treating a subject having cancer using one or more of the methods provided herein, together with surgery. Particular embodiments provide treating a subject having cancer using one or more of the methods provided herein, together with chemotherapy. Particular embodiments provide treating a subject having cancer using one or more of the methods provided herein, together with immunotherapy. Particular embodiments provide treating a subject having cancer using one or more of the methods provided herein, together with targeted therapy. Particular embodiments provide treating a subject having cancer using one or more of the methods provided herein, together with radiation therapy. Particular embodiments provide treating a subject having cancer using one or more of the methods provided herein, together with two or more of the treatments selected from surgery, chemotherapy, immunotherapy, targeted therapy, and radiation therapy. Particular embodiments provide treating a subject having cancer using one or more of the methods provided herein, together with two or more of the treatments selected from surgery, chemotherapy, and radiation therapy.

In certain embodiments, the subject to be treated with one of the methods provided herein has not been treated with anticancer therapy prior to the administration of the cytidine analog. In certain embodiments, the subject to be treated with one of the methods provided herein has been treated with one or more anticancer therapies prior to the administration of the cytidine analog. In certain embodiments, the subject to be treated with one of the methods provided herein has been treated with a cancer therapeutic agent, as described herein. In certain embodiments, the subject to be treated with one of the methods provided herein has developed drug resistance to anticancer therapy. In certain embodiments, the subject to be treated with the methods provided herein has a relapsed cancer. In certain embodiments, the subject to be treated with the methods provided herein has a refractory cancer. In certain embodiments, the subject to be treated with the methods provided herein has a metastatic cancer.

In one embodiment, the methods provided herein encompass treating a subject regardless of patient's age, although some diseases or disorders are more common in certain age groups. Further provided herein is a method for treating a subject who has undergone surgery in an attempt to treat the disease or condition at issue. Further provided herein is a method for treating a subject who has not undergone surgery as an attempt to treat the disease or condition at issue. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

In each embodiment provided herein, the method may further comprise one or more diagnostic steps, to determine, e.g., the type of cancer, the presence of particular cell types, the genetic profile of a subject, and/or the staging of the disease in a subject.

In each embodiment provided herein, the method may further comprise a disease evaluation step after the cytidine analog has been administered to the subject, to determine, e.g., changes in one or more molecular markers as described herein elsewhere, changes in tumor size and location, and/or other benchmarks used by those skilled in the art to determine the prognosis of cancer in a subject.

Certain methods herein provide administration of a cytidine analog by, e.g., intravenous (IV), subcutaneous (SC) or oral routes of administration. Certain methods herein provide administration of a cytidine analog by oral route of administration. Certain embodiments herein provide co-administration of a cytidine analog (e.g., 5-azacytidine or another cytidine analog provided herein) with one or more additional active agents to provide a synergistic therapeutic effect in subjects in need thereof. The co-administered agent(s) may be a cancer therapeutic agent, as described herein. In certain embodiments, the co-administered agent(s) may be dosed, e.g., orally or by injection (e.g., IV or SC).

Certain embodiments herein provide methods for treating disorders of abnormal cell proliferation comprising administering a cytidine analog using, e.g., IV, SC and/or oral administration methods. Certain embodiments herein provide methods for treating disorders of abnormal cell proliferation comprising administering a cytidine analog using oral administration methods. In certain embodiments, treatment cycles comprise multiple doses administered to a subject in need thereof over multiple days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days), optionally followed by treatment dosing holidays (e.g., 1, 2, 3, 4, 5, 6, 7, 8, 9, 10, 11, 12, 13, 14, 15, 16, 17, 18, 19, 20, 21, 22, 23, 24, 25, 26, 27, 28, or greater than 28 days). Suitable dosage amounts for the methods provided herein include, e.g., therapeutically effective amounts and prophylactically effective amounts. In specific embodiments, a treatment cycle comprises multiple doses administered to a subject in need thereof once a day or more than once a day, for 3 days, for 5 days, for 7 days, for 14 days, for 21 days, or for 28 days. In specific embodiments, a treatment cycle comprises a resting period of 1 day, 2 days, 3 days, 4 days, 5 days, 7 days, 14 days, 21 days, or 28 days. In specific embodiments, a subject is treated with multiple treatment cycles, for example, multiple 7-day, 14-day, 21-day, 28-day, 35-day, or 42-day treatment cycles for a total period of treatment of about 1, 2, 3, 4, 5, 6, 7, 8, 9, 10, 11, 12, 13, 14, 15, 16, 17, 18, 19, 20, 21, 22, 23, or 24 months, or greater than 24 months. In specific embodiments, a subject is treated with multiple treatment cycles, that may be the same or different (e.g., a 7-day treatment cycle followed by a 14-day, 21-day, or 28-day treatment cycle).

In one embodiment, the amount of the cytidine analog (e.g., 5-azacytidine or another cytidine analog provided herein) administered in the methods provided herein may range, e.g., between about 50 mg/m$^2$/day and about 2,000 mg/m$^2$/day, between about 100 mg/m$^2$/day and about 1,000 mg/m$^2$/day, between about 50 mg/m$^2$/day and about 200 mg/m$^2$/day, between about 50 mg/m$^2$/day and about 100 mg/m$^2$/day, between about 100 mg/m$^2$/day and about 500 mg/m$^2$/day, or between about 120 mg/m$^2$/day and about 250 mg/m$^2$/day. In certain embodiments, particular dosages are, e.g., about 50 mg/m$^2$/day, about 75 mg/m$^2$/day, about 100 mg/m$^2$/day, about 120 mg/m$^2$/day, about 140 mg/m$^2$/day, about 150 mg/m$^2$/day, about 180 mg/m$^2$/day, about 200 mg/m$^2$/day, about 220 mg/m$^2$/day, about 240 mg/m$^2$/day, about 250 mg/m$^2$/day, about 260 mg/m$^2$/day, about 280 mg/m$^2$/day, about 300 mg/m$^2$/day, about 320 mg/m$^2$/day, about 350 mg/m$^2$/day, about 380 mg/m$^2$/day, about 400 mg/m$^2$/day, about 450 mg/m$^2$/day, or about 500 mg/m$^2$/day. In certain embodiments, particular dosages are, e.g., up to about 100 mg/m$^2$/day, up to about 120 mg/m$^2$/day, up to about 140 mg/m$^2$/day, up to about 150 mg/m$^2$/day, up to about 180 mg/m$^2$/day, up to about 200 mg/m$^2$/day, up to about 220 mg/m$^2$/day, up to about 240 mg/m$^2$/day, up to about 250 mg/m$^2$/day, up to about 260 mg/m$^2$/day, up to about 280 mg/m$^2$/day, up to about 300 mg/m$^2$/day, up to about 320 mg/m$^2$/day, up to about 350 mg/m$^2$/day, up to about 380 mg/m$^2$/day, up to about 400 mg/m$^2$/day, up to about 450 mg/m$^2$/day, up to about 500 mg/m$^2$/day, up to about 750 mg/m$^2$/day, or up to about 1000 mg/m$^2$/day.

In one embodiment, the amount of the cytidine analog (e.g., 5-azacytidine or another cytidine analog provided herein) administered in the methods provided herein may range, e.g., between about 5 mg/day and about 2,000 mg/day, between about 10 mg/day and about 2,000 mg/day, between about 20 mg/day and about 2,000 mg/day, between about 50 mg/day and about 1,000 mg/day, between about 100 mg/day and about 600 mg/day, between about 100 mg/day and about 500 mg/day, between about 150 mg/day and about 500 mg/day, between about 250 mg/day and about 350 mg/day, or between about 150 mg/day and about 250 mg/day. In certain embodiments, particular dosages are, e.g., about 10 mg/day, about 20 mg/day, about 50 mg/day, about 75 mg/day, about 100 mg/day, about 120 mg/day, about 150 mg/day, about 180 mg/day, about 200 mg/day, about 240 mg/day, about 250 mg/day, about 280 mg/day, about 300 mg/day, about 320 mg/day, about 350 mg/day, about 360 mg/day, about 400 mg/day, about 450 mg/day, about 500 mg/day, about 600 mg/day, about 700 mg/day, about 800 mg/day, about 900 mg/day, about 1,000 mg/day, about 1,200 mg/day, or about 1,500 mg/day. In certain embodiments, particular dosages are, e.g., up to about 10 mg/day, up to about 20 mg/day, up to about 50 mg/day, up to about 75 mg/day, up to about 100 mg/day, up to about 120 mg/day, up to about 150 mg/day, up to about 200 mg/day, up to about 250 mg/day, up to about 300 mg/day, up to about 350 mg/day, up to about 400 mg/day, up to about 450 mg/day, up to about 500 mg/day, up to about 600 mg/day, up to about 700 mg/day, up to about 800 mg/day, up to about 900 mg/day, up to about 1,000 mg/day, up to about 1,200 mg/day, or up to about 1,500 mg/day.

In one embodiment, the amount of the cytidine analog (e.g., 5-azacytidine or another cytidine analog provided herein) in the pharmaceutical composition or dosage form provided herein may range, e.g., between about 5 mg and about 2,000 mg, between about 10 mg and about 2,000 mg, between about 20 mg and about 2,000 mg, between about 50 mg and about 1,000 mg, between about 100 mg and about 600 mg, between about 100 mg and about 500 mg, between about 150 mg and about 500 mg, between about 250 mg and about 350 mg, or between about 150 mg and about 250 mg. In certain embodiments, particular amounts are, e.g., about 10 mg, about 20 mg, about 50 mg, about 75 mg, about 100 mg, about 120 mg, about 150 mg, about 180 mg, about 200 mg, about 240 mg, about 250 mg, about 300 mg, about 320 mg, about 350 mg, about 360 mg, about 400 mg, about 420 mg, about 450 mg, about 480 mg, about 500 mg, about 600 mg, about 700 mg, about 800 mg, about 900 mg, about 1,000 mg, about 1,200 mg, or about 1,500 mg. In certain embodiments, particular amounts are, e.g., up to about 10 mg, up to about 20 mg, up to about 50 mg, up to about 75 mg, up to about 100 mg, up to about 120 mg, up to about 150 mg, up to about 200 mg, up to about 250 mg, up to about 300 mg, up to about 350 mg, up to about 400 mg, up to about 450 mg, up to about 500 mg, up to about 600 mg, up to about 700 mg, up to about 800 mg, up to about 900 mg, up to about 1,000 mg, up to about 1,200 mg, or up to about 1,500 mg.

In one embodiment, depending on the disease to be treated and the subject's condition, the cytidine analog (e.g., 5-azacytidine or another cytidine analog provided herein) may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. In some embodiments, the cytidine analog may be formulated, alone or together with one or more active agent(s), in suitable dosage unit with pharmaceutically acceptable excipients, carriers, adjuvants and vehicles, appropriate for each route of administration. In one embodiment, the cytidine analog (e.g., 5-azacytidine or another cytidine analog provided herein) is administered orally. In another embodiment, the cytidine analog (e.g., 5-azacytidine or another cytidine analog provided herein) is administered parenterally. In yet another embodiment, the cytidine analog (e.g., 5-azacytidine or another cytidine analog provided herein) is administered intravenously. In yet another embodiment, the cytidine analog (e.g., 5-azacytidine or another cytidine analog provided herein) is administered subcutaneously.

In one embodiment, the cytidine analog (e.g., 5-azacytidine or another cytidine analog provided herein) can be delivered as a single dose such as, e.g., a single bolus injection, or oral tablets or pills; or over time such as, e.g., continuous infusion over time or divided bolus doses over time. In one embodiment, the cytidine analog (e.g., 5-azacytidine or another cytidine analog provided herein) can be administered repetitively if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. See, e.g., Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In one embodiment, the cytidine analog (e.g., 5-azacytidine or another cytidine analog provided herein) can be administered once daily (QD), or divided into multiple daily doses such as twice daily (BID), three times daily (TID), and four times daily (QID). In one embodiment, the administration can be continuous (i.e., daily for consecutive days or every day), intermittent, e.g., in cycles (i.e., including days, weeks, or months of rest when no drug is administered). In one embodiment, the cytidine analog is administered daily, for example, once or more than once each day for a period of time. In one embodiment, the cytidine analog is administered daily for an uninterrupted period of at least 7 days, in some embodiments, up to 52 weeks. In one embodiment, the cytidine analog is administered intermittently, i.e., stopping and starting at either regular or irregular intervals. In one embodiment, the cytidine analog is administered for one to six days per week. In one embodiment, the cytidine analog is administered in cycles (e.g., daily administration for about one, two, three, four, five, six, seven, or eight consecutive weeks, then a rest period with no administration for about one, two, three, or four weeks). In one embodiment, the cytidine analog is administered on alternate days. In one embodiment, the cytidine analog is administered in cycles (e.g., administered daily or continuously for a certain period interrupted with a rest period).

In one embodiment, the frequency of administration ranges from about daily to about monthly. In certain embodiments, the cytidine analog (e.g., 5-azacytidine or another cytidine analog provided herein) is administered once a day, twice a day, three times a day, four times a day, once every other day, twice a week, once every week, once every two weeks, once every three weeks, or once every four weeks. In one embodiment, the cytidine analog is administered once a day. In another embodiment, the cytidine analog is administered twice a day. In yet another embodiment, the cytidine analog is administered three times a day. In still another embodiment, the cytidine analog is administered four times a day.

In one embodiment, the cytidine analog (e.g., 5-azacytidine or another cytidine analog provided herein) is administered once per day from one day to six months, from one week to three months, from one week to four weeks, from one week to three weeks, or from one week to two weeks. In certain embodiments, the cytidine analog is administered once per day for one week, two weeks, three weeks, or four weeks. In one embodiment, the cytidine analog is administered once per day for one week. In another embodiment, the cytidine analog is administered once per day for two weeks. In yet another embodiment, the cytidine analog is administered once per day for three weeks. In still another embodiment, the cytidine analog is administered once per day for four weeks.

In one embodiment, the cytidine analog (e.g., 5-azacytidine or another cytidine analog provided herein) is administered once per day for about 1 week, about 2 weeks, about 3 weeks, about 4 weeks, about 6 weeks, about 9 weeks, about 12 weeks, about 15 weeks, about 18 weeks, about 21 weeks, or about 26 weeks. In certain embodiments, the cytidine analog is administered intermittently. In certain embodiments, the cytidine analog is administered intermittently in the amount of between about 50 $mg/m^2$/day and about 2,000 $mg/m^2$/day. In certain embodiments, the cytidine analog is administered intermittently in the amount of between about 100 mg/day and about 600 mg/day. In certain embodiments, the cytidine analog is administered continuously. In certain embodiments, the cytidine analog is administered continuously in the amount of between about 50 $mg/m^2$/day and about 1,000 $mg/m^2$/day. In certain embodiments, the cytidine analog is administered continuously in the amount of between about 100 mg/day and about 600 mg/day.

In certain embodiments, the cytidine analog (e.g., 5-azacytidine or another cytidine analog provided herein) is administered to a patient in cycles. Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

In one embodiment, the cytidine analog (e.g., 5-azacytidine or another cytidine analog provided herein) is administered daily in single or divided doses for about 3 days, about 5 days, about one week, about two weeks, about three weeks, about four weeks, about five weeks, about six weeks, about seven weeks, about eight weeks, about ten weeks, about fifteen weeks, or about twenty weeks, followed by a rest period of about 1 day to about ten weeks. In one embodiment, the methods provided herein contemplate cycling treatments of about one week, about two weeks, about three weeks, about four weeks, about five weeks, about six weeks, about eight weeks, about ten weeks, about fifteen weeks, or about twenty weeks. In some embodiments, the cytidine analog is administered daily in single or divided doses for about 3 days, about 5 days, about one week, about two weeks, about three weeks, about four weeks, about five weeks, or about six weeks with a rest period of about 1, 2, 3, 4, 5, 6, 7, 8, 9, 10, 12, 14, 16, 18, 20, 22, 24, 26, 28, 29, or 30 days. In some embodiments, the rest period is 1 day. In some embodiments, the rest period is 3 days. In some embodiments, the rest period is 7 days. In some embodiments, the rest period is 14 days. In some embodiments, the rest period is 28 days. The frequency, number and length of dosing cycles can be increased or decreased.

In one embodiment, the methods provided herein comprise: i) administering to the subject a first daily dose of a cytidine analog; ii) optionally resting for a period of at least one day where the cytidine analog is not administered to the subject; iii) administering a second dose of the cytidine analog to the subject; and iv) repeating steps ii) to iii) a plurality of times. In certain embodiments, the first daily dose is between about 50 mg/m$^2$/day and about 2,000 mg/m$^2$/day. In certain embodiments, the second daily dose is between about 50 mg/m$^2$/day and about 2,000 mg/m$^2$/day. In certain embodiments, the first daily dose is between about 100 mg/day and about 1,000 mg/day. In certain embodiments, the second daily dose is between about 100 mg/day and about 1,000 mg/day. In certain embodiments, the first daily dose is higher than the second daily dose. In certain embodiments, the second daily dose is higher than the first daily dose. In one embodiment, the rest period is 1 day, 2 days, 3 days, 5 days, 7 days, 10 days, 12 days, 13 days, 14 days, 15 days, 17 days, 21 days, or 28 days.

In certain embodiments, the cytidine analog (e.g., 5-azacytidine or another cytidine analog provided herein) is administered continuously for between about 1 and about 52 weeks. In certain embodiments, the cytidine analog is administered continuously for about 0.5, 1, 2, 3, 4, 5, 6, 7, 8, 9, 10, 11, or 12 months. In certain embodiments, the cytidine analog is administered continuously for about 7, about 14, about 21, about 28, about 35, about 42, about 84, or about 112 days. It is understood that the duration of the treatment may vary with the age, weight, and condition of the subject being treated, and may be determined empirically using known testing protocols or according to the professional judgment of the person providing or supervising the treatment. The skilled clinician will be able to readily determine, without undue experimentation, an effective drug dose and treatment duration, for treating an individual subject having a particular type of cancer.

1. Methods of Using Oral Formulations Provided Herein

As described herein, certain embodiments herein provide oral formulations of cytidine analogs useful in methods relating to, e.g., permitting different dosing amounts and/or dosing periods; providing alternative pharmacokinetic profiles, pharmacodynamic profiles, and/or safety profiles; permitting the evaluation of long-term and/or maintenance therapies; providing treatment regimens that maximize demethylation and/or gene re-expression; providing treatment regimens that prolong continuous demethylation; providing new indications for cytidine analogs; and/or providing other potential advantageous benefits.

Provided herein are methods of treating, preventing, or managing patho-physiological conditions manifested by abnormal cell proliferation, such as, for example, cancer, including hematological disorders and solid tumors, by orally administering a pharmaceutical formulation comprising a cytidine analog, such as, for example, 5-azacytidine, wherein the formulation releases the cytidine analog substantially in the stomach. Other embodiments herein provide methods of treating, preventing, or managing immune disorders. In particular embodiments, the methods provided herein involve oral administering a formulation that effects an immediate release of the cytidine analog. In certain embodiments, the cytidine analog and one or more therapeutic agents are co-administered to subjects to yield a synergistic therapeutic effect. The co-administered agent may be a cancer therapeutic agent dosed orally or by injection.

In certain embodiments, methods provided herein for treating, preventing, or managing disorders related to abnormal cell proliferation comprise orally administering a formulation comprising a therapeutically effective amount of a cytidine analog. Particular therapeutic indications relating to the methods provided herein are disclosed herein. In certain embodiments, the therapeutically effective amount of the cytidine analog in the pharmaceutical formulation is an amount as disclosed herein. In certain embodiments, the precise therapeutically effective amount of the cytidine analog in the pharmaceutical formulation will vary depending on, e.g., the age, weight, disease and/or condition of the subject.

In particular embodiments, the disorders related to abnormal cell proliferation include, but are not limited to, solid tumors, sarcoma, melanoma, carcinoma, adenocarcinoma, chordoma, breast cancer, colorectal cancer, ovarian cancer, lung cancer (e.g., non-small-cell lung cancer and small-cell lung cancer), testicular cancer, renal cancer, bladder cancer, pancreatic cancer, bone cancer, gastric cancer, head and neck cancer, prostate cancer, MDS, AML, ALL, CML, leukemia, chronic lymphocytic leukemia (CLL), lymphoma (including non-Hodgkin's lymphoma (NHL) and Hodgkin's lymphoma), and multiple myeloma (MM). In particular embodiments, the disorder related to abnormal cell proliferation is a solid tumor. In particular embodiments, the disorder related to abnormal cell proliferation is a relapsed or refractory solid tumor. In particular embodiments, the disorder related to abnormal cell proliferation is MDS. In particular embodiments, the disorder related to abnormal cell proliferation is AML. In particular embodiments, the disorder related to abnormal cell proliferation is breast cancer. In particular embodiments, the disorder related to abnormal cell proliferation is bladder cancer. In particular embodiments, the disorder related to abnormal cell proliferation is head and neck cancer. In particular embodiments, the disorder related to abnormal cell proliferation is pancreatic cancer. In particular embodiments, the disorder related to abnormal cell proliferation is lung cancer (e.g., NSCLC or SCLC). In particular embodiments, the disorder related to abnormal cell proliferation is ovarian cancer. In particular embodiments, the disorder related to abnormal cell proliferation is colorectal cancer. In particular embodiments, the disorder related to abnormal cell proliferation is skin cancer (e.g., melanoma). In particular embodiments, the disorder related to abnormal cell proliferation is uterine cancer. In particular embodiments, the disorder related to abnormal cell proliferation is sarcoma.

In one embodiment, methods provided herein for treating, preventing, or managing disorders of abnormal cell proliferation comprise administering a cytidine analog orally. In other embodiments, methods provided herein for treating, preventing, or managing disorders of abnormal cell proliferation comprise administering a cytidine analog using at least two of IV, SC and oral administration methods. For example, particular embodiments herein provide administering an initial treatment cycle of a cytidine analog, such as, for example, 5-azacytidine, administered either SC or IV, followed by subsequent orally administered treatment cycles of the cytidine analog. In certain embodiments, treatment cycles comprise multiple doses administered to a subject in need thereof over multiple days (e.g., 1, 2, 3, 4, 5, 6, 7, 8, 9, 10, 11, 12, 13, 14, 15, 16, 17, 18, 19, 20, 21, or greater than 21 days), optionally followed by treatment dosing holidays (e.g., 1, 2, 3, 4, 5, 6, 7, 8, 9, 10, 11, 12, 13, 14, or greater than 14 days). Particular embodiments herein provide a treatment schedule comprising SC and/or IV administration for one, two, three, four, five, or more initial cycles, followed by oral administration for subsequent cycles. For example, particular embodiments herein provide a treatment schedule comprising SC administration for cycle 1, followed by oral administration for subsequent cycles. Suitable dosage ranges and amounts for the methods provided herein are provided throughout the specification. For example, in certain embodiments, the SC dose is about 75 mg/m$^2$. In certain embodiments, the oral dose is about 50 mg, about 60 mg, about 70 mg, about 80 mg, about 90 mg, about 100 mg, about 120 mg, about 140 mg, about 150 mg, about 160 mg, about 180 mg, about 200 mg, about 220 mg, about 240 mg, about 250 mg, about 260 mg, about 280 mg, about 300 mg, about 320 mg, about 340 mg, about 350 mg, about 360 mg, about 380 mg, about 400 mg, about 420 mg, about 450 mg, about 480 mg, about 500 mg, about 600 mg, or greater than about 600 mg. In certain embodiments, oral doses are calculated to achieve about 80%, 100%, or 120% of SC AUC.

In certain embodiments, methods of treating disorders of abnormal cell proliferation comprises orally administering a formulation comprising a cytidine analog (e.g., 5-azacytidine or another cytidine analog provided herein) as single or multiple daily doses. In particular embodiments, a formulation comprising a cytidine analog is orally administered once per day, twice per day, three times per day, four times per day, or more than four times per day. For example, in certain embodiments, a formulation comprising a cytidine analog is administered using a treatment cycle comprising administration of about 50 mg, about 60 mg, about 70 mg, about 80 mg, about 90 mg, about 100 mg, about 120 mg, about 140 mg, about 150 mg, about 160 mg, about 180 mg, about 200 mg, about 220 mg, about 240 mg, about 250 mg, about 260 mg, about 280 mg, about 300 mg, about 320 mg, about 340 mg, about 350 mg, about 360 mg, about 380 mg, about 400 mg, about 420 mg, about 450 mg, about 480 mg, about 500 mg, about 600 mg, about 700 mg, about 800 mg, about 900 mg, or about 1,000 mg of the cytidine analog once, twice, three, or four times per day for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In certain embodiments, the method of treating comprises continuous low-dose administration. In certain embodiments, the formulation comprising the cytidine analog is administered using a treatment cycle comprising administration of about 200 mg of the cytidine analog once per day for 7 or more days. In certain embodiments, the formulation comprising the cytidine analog is administered using a treatment cycle comprising administration of about 200 mg of the cytidine analog twice per day for 7 or more days. In certain embodiments, the formulation comprising the cytidine analog is administered using a treatment cycle comprising administration of about 200 mg of the cytidine analog once per day for 14 or more days. In certain embodiments, the formulation comprising the cytidine analog is administered using a treatment cycle comprising administration of about 200 mg of the cytidine analog twice per day for 14 or more days. In certain embodiments, the formulation comprising the cytidine analog is administered using a treatment cycle comprising administration of about 200 mg of the cytidine analog once per day for 21 or more days. In certain embodiments, the formulation comprising the cytidine analog is administered using a treatment cycle comprising administration of about 200 mg of the cytidine analog twice per day for 21 or more days. In certain embodiments, the formulation comprising the cytidine analog is administered using a treatment cycle comprising administration of about 200 mg of the cytidine analog three times per day for 7 or more days. In certain embodiments, the formulation comprising the cytidine analog is administered using a treatment cycle comprising administration of about 200 mg of the cytidine analog three times per day for 14 or more days. In certain embodiments, the formulation comprising the cytidine analog is administered using a treatment cycle comprising administration of about 300 mg of the cytidine analog once per day for 7 or more days. In certain embodiments, the formulation comprising the cytidine analog is administered using a treatment cycle comprising administration of about 300 mg of the cytidine analog twice per day for 7 or more days. In certain embodiments, the formulation comprising the cytidine analog is administered using a treatment cycle comprising administration of about 300 mg of the cytidine analog once per day for 14 or more days. In certain embodiments, the formulation comprising the cytidine analog is administered using a treatment cycle comprising administration of about 300 mg of the cytidine analog twice per day for 14 or more days. In certain embodiments, the formulation comprising the cytidine analog is administered using a treatment cycle comprising administration of about 300 mg of the cytidine analog once per day for 21 or more days. In certain embodiments, the formulation comprising the cytidine analog is administered using a treatment cycle comprising administration of about 300 mg of the cytidine analog twice per day for 21 or more days. In certain embodiments, the formulation comprising the cytidine analog is administered using a treatment cycle comprising administration of about 300 mg of the cytidine analog three times per day for 7 or more days. In certain embodiments, the formulation comprising the cytidine analog is administered using a treatment cycle comprising administration of about 300 mg of the cytidine analog three times per day for 14 or more days. In certain embodiments, methods provided herein comprise administering a formulation comprising a cytidine analog using one or more of the cycles provided herein, and repeating one or more of the cycles for a period of, e.g., about 1, 2, 3, 4, 5, 6, 7, 8, 9, 10, 11, 12, or greater than 12 months.

In certain embodiments, methods herein comprise administering particular oral formulations provided herein to, e.g., overcome limitations associated with IV or SC administration of cytidine analogs. For example, IV or SC administration may limit the ability to deliver a cytidine analog for longer periods of time on a regular basis, thereby potentially limiting the maximal efficacy of the cytidine analog. Due to the difficulties of complying with the rigors of a prolonged IV or SC dosing schedule, prolonged SC or IV exposure to a cytidine analog may cause subjects (e.g., subjects with multiple cytopenias) to discontinue from the regimen. See, e.g., Lyons, R. M., et al., Hematologic Response to Three Alternative Dosing Schedules of Azacitidine in Patients With Myelodysplastic Syndromes, *J. Clin. Oncol.* (2009) (DOI: 10.1200/JCO.2008.17.1058), which is incorporated by reference herein in its entirety. Accordingly, in certain embodiments, methods provided herein comprise administering an oral formulation provided herein to overcome these or other limitations associated with SC or IV cytidine analog administration. For example, in certain embodiments, methods provided herein comprise administering daily to a subject an oral formulation provided herein for 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, or 28 or more days.

Certain embodiments herein provide methods comprising administering oral formulations of cytidine analogs provided herein comprising delivering the cytidine analog (e.g., 5-azacytidine or another cytidine analog provided herein) at a lower dose over a more prolonged period of time, as compared to IV or SC administration. In particular embodiments, such methods comprise managing dose-related cytopenias (including, e.g., dose-related cytopenias associated with 5-azacytidine) by administering an oral formulation provided herein. In certain embodiments, methods provided herein comprise administering an oral formulation provided herein to achieve an improved safety profile as compared to an IV or SC dose comprising the same cytidine analog.

As described herein, certain embodiments provide methods for improved treatment of particular diseases or disorders (e.g., treatment of solid tumors) by administering an oral formulation provided herein, as compared to IV or SC administration of the cytidine analog. In particular embodiments, certain methods herein provide administering oral formulations provided herein at lower doses for more prolonged periods of time, leading to improved demethylation. For example, certain methods provided herein comprise administering an oral formulation provided herein to treat a solid tumor while avoiding certain dose-limiting-toxicity-related side effects associated with dosing the cytidine analog via SC or IV administration. An example of certain toxicity-related drawbacks associated with administration of a cytidine analog are described, e.g., in K. Appleton et al., *J. Clin. Oncol.*, Vol. 25(29):4603-4609 (2007), which is incorporated by reference herein in its entirety.

Particular embodiments herein provide methods for treating a subject having a disease or disorder provided herein by orally administering a pharmaceutical composition provided herein, wherein the treatment results in improved survival of the subject. In certain embodiments, the improved survival is measured as compared to one or more conventional care regimens. Particular embodiments herein provide methods for treating a subject having a disease or disorder provided herein by orally administering a pharmaceutical composition provided herein, wherein the treatment provides improved effectiveness. In particular embodiments, the improved effectiveness is measured using one or more endpoints for cancer clinical trials, as recommended by the U.S. Food and Drug Administration (FDA). For example, FDA provides Guidance for Industry on Clinical Trial Endpoints for the Approval of Cancer Drugs and Biologics (http://www.fda.gov/CbER/gdlns/clintrialend.htm). The FDA endpoints include, but are not limited to, Overall Survival, Endpoints Based on Tumor Assessments such as (i) Disease-Free Survival (ii) Objective Response Rate, (iii) Time to Progression and Progression-Free Survival and (iv) Time-to-Treatment Failure. Endpoints Involving Symptom Endpoints may include Specific Symptom Endpoints such as (i) Time to progression of cancer symptoms and (ii) A composite symptom endpoint. Biomarkers assayed from blood or body fluids may also be useful to determine the management of the disease.

In certain embodiments, the methods of treating disorders of abnormal cell proliferation comprise orally administering a formulation of a cytidine analog with food. In certain embodiments, the methods of treating disorders of abnormal cell proliferation comprise orally administering a formulation of a cytidine analog without food. In certain embodiments, pharmacological parameters (e.g., Cmax, Tmax) depend on the fed state of the subject. In certain embodiments, the formulation of the cytidine analog is administered sublingually.

In certain embodiments, the cytidine analog, e.g., 5-azacytidine or another cytidine analog provided herein, is not co-administered with a cytidine deaminase inhibitor. In certain embodiments, the oral formulation comprising a cytidine analog as provided herein is not co-administered with THU. Certain embodiments herein provide methods of treating a disease or disorder provided herein (e.g., a disease associated with abnormal cell proliferation) comprising orally administering a cytidine analog provided herein for release substantially in the stomach, wherein the methods achieve a particular biological parameter provided herein (e.g., a particular Cmax value, $T_{max}$ value, and/or AUC value provided herein), and wherein the methods comprise not co-administering a cytidine deaminase inhibitor with the cytidine analog. Certain embodiments herein provide methods of treating a disease or disorder provided herein (e.g., a disease associated with abnormal cell proliferation) comprising orally administering a cytidine analog provided herein for release substantially in the stomach, wherein the methods avoid adverse effects associated with administering a cytidine deaminase inhibitor (e.g., THU) by not co-administering the cytidine deaminase inhibitor with the cytidine analog. In particular embodiments, a cytidine deaminase inhibitor (e.g., THU) is co-administered with the cytidine analog in an amount of, e.g., less than about 500 mg/d, less than about 200 mg/d, less than about 150 mg/d, less than about 100 mg/d, less than about 50 mg/d, less than about 25 mg/d, less than about 10 mg/d, less than about 5 mg/d, less than about 1 mg/d, or less than about 0.1 mg/d.

Certain embodiments herein provide methods for delivering a cytidine analog to a subject comprising administering to the subject in need thereof an oral formulation comprising a cytidine analog. In particular embodiments, oral formulations comprise (1) a therapeutically effective amount of a cytidine analog; and (2) an optional drug release controlling component capable of releasing the cytidine analog substantially in the stomach after a subject ingests the oral formulation comprising the cytidine analog. Certain embodiments herein provide a method for enhancing the oral bioavailability of a cytidine analog in a subject. Certain embodiments herein provide a method of increasing the oral bioavailability of a cytidine analog comprising orally administering a pharmaceutical composition provided herein. In certain methods provided herein, a pharmaceutical composition provided herein is orally administered to a subject, contacts the biological fluids of the subject's body, and is absorbed in the upper gastrointestinal tract, such as, for example, substantially in the stomach.

Certain embodiments herein provide a method of achieving a particular exposure value provided herein by administering an oral formulation comprising a cytidine analog provided herein. Certain embodiments herein provide a method of achieving a particular oral bioavailability value provided herein by administering an oral formulation comprising a cytidine analog provided herein. Certain embodiments herein provide a method of achieving a particular AUC value provided herein by administering an oral formulation comprising a cytidine analog provided herein. Certain embodiments herein provide a method of achieving a particular Cmax value provided herein by administering an oral formulation comprising a cytidine analog provided herein. Certain embodiments herein provide a method of achieving a particular Tmax value provided herein by administering an oral formulation comprising a cytidine analog provided herein.

Certain embodiments herein provide methods of treating a condition involving undesirable or uncontrolled cell proliferation by administering an oral formulation comprising a cytidine analog as provided herein. Such conditions include, e.g., benign tumors, various types of cancers such as primary tumors and tumor metastasis, solid tumors (e.g., relapsed or refractory solid tumors), hematological disorders (e.g. leukemia, myelodysplastic syndrome and sickle cell anemia), restenosis (e.g. coronary, carotid, and cerebral lesions), abnormal stimulation of endothelial cells (arteriosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

In certain embodiments, cells in a benign tumor retain their differentiated features and do not divide in a completely uncontrolled manner. A benign tumor may be localized and/or nonmetastatic. Specific types of benign tumors that can be treated using the methods, compositions, and formulations provided herein include, e.g., hemangiomas, hepatocellular adenoma, cavernous hemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In certain embodiments, cells in a malignant tumor become undifferentiated, do not respond to the body's growth control signals, and/or multiply in an uncontrolled manner. The malignant tumor may be invasive and capable of spreading to distant sites (metastasizing). Malignant tumors may be divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.).

Without being limited by a particular theory, methylation can lead to the silencing of genes critical to cellular control (i.e., epigenetic gene silencing), and can be an early event in the development of malignant tumors including, e.g., colorectal cancer or lung cancer. See, e.g., M. V. Brock et al., *N. Engl. J. Med.,* 2008, 358(11):1118-28; P. M. Das et al., *Mol. Cancer,* 2006, 5(28); G. Gifford et al., *Clin. Cancer Res.,* 2004, 10:4420-26; J. G. Herman et al., *N. Engl. J. Med.,* 2003, 349:2042-54; A. M. Jubb et al., *J. Pathology,* 2001, 195:111-34. Accordingly, in certain embodiments, without being limited by a particular theory, methods herein provide using oral formulations provided herein to prevent or reverse epigenetic gene silencing, e.g., by reversing abnormal DNA methylation. In specific embodiments, oral formulations provided herein are used for early intervention to prevent the development of cancer in patients at risk of developing cancer, e.g., familial polyposis or lung cancer, wherein a cause of the cancer is epigenetic gene silencing. In particular embodiments, such early intervention would be impractical by means other than oral administration (e.g., IV or SC administration). In specific embodiments, oral formulations provided herein are used for early intervention to prevent the recurrence of cancer in patients at risk for early relapse, e.g., colorectal cancer or non-small-cell lung cancer. In certain embodiments, the early intervention is achieved via prolonged oral dosing schedules, using formulations and/or methods as described herein. Certain embodiments provide methods for administering oral formulations provided herein to reverse the effect of gene silencing, e.g., in patients at risk of gene silencing due to epigenetic changes.

In certain embodiments, specific types of cancers or malignant tumors, either primary or secondary, that can be treated using the methods, compositions, and formulations provided herein include, e.g., leukemia, lymphoma, breast cancer, skin cancer, bone cancer, prostate cancer, liver cancer, lung cancer (e.g., non-small-cell lung cancer and small-cell lung cancer), brain cancer, cancer of the larynx, gall bladder, pancreas, rectum, uterine, prostate, parathyroid, thyroid, adrenal, neural tissue, head and neck, colon, stomach, bronchi, kidney, or bladder, basal cell carcinoma, squamous cell carcinoma of both ulcerating and papillary type, melanoma, metastatic skin carcinoma, sarcoma, osteo sarcoma, Ewing's sarcoma, veticulum cell sarcoma, myeloma, multiple myeloma, giant cell tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronmas, intestinal ganglioneuromas, hyperplastic corneal nerve tumor, marfanoid habitus tumor, Wilm's tumor, seminoma, ovarian cancer, leiomyoma tumor, cervical squamous cell carcinoma, cervical dysplasia and in situ carcinoma, neuroblastoma, retinoblastoma, medulloblastoma, soft tissue sarcoma, malignant carcinoid, topical skin lesion, mycosis fungoides, rhabdomyosarcoma, Kaposi's sarcoma, osteogenic and other sarcoma, malignant hypercalcemia, renal cell tumor, polycythermia vera, adenocarcinoma, glioblastoma multiforma, malignant melanoma, epidermoid carcinoma, other carcinomas and sarcomas, relapsed or refractory solid tumors, and advanced metastatic solid tumors.

Particular embodiments herein provide using the methods, compositions, and formulations provided herein to treat abnormal cell proliferation due to, e.g., insults to body tissue during surgery for a variety of surgical procedures, including, e.g., joint surgery, bowel surgery, and cheloid scarring. Proliferative responses associated with organ transplantation that may be treated using the methods, compositions, and formulations provided herein include those proliferative responses contributing to potential organ rejections or associated complications. Specifically, these proliferative responses may occur during transplantation of the heart, lung (e.g., non-small-cell lung cancer and small-cell lung cancer), liver, kidney, and other body organs or organ systems.

In certain embodiments, the amount of the cytidine analog in the oral formulations provided herein, the methods of administration thereof, or the methods of treatment as set forth herein, is a specific dosage amount as provided herein.

2. Biomarkers

In certain embodiments, appropriate biomarkers may be used to determine or predict the effect of the methods provided herein on the disease state and to provide guidance as to the dosing schedule. For example, particular embodiments herein provide a method for determining whether a patient diagnosed with cancer has an increased probability of obtaining a greater benefit from treatment with a pharmaceutical composition comprising a cytidine analog, e.g., by assessing the patient's nucleic acid methylation status. In particular embodiments, the cytidine analog is 5-azacytidine. In particular embodiments, the cytidine analog is decitabine. In particular embodiments, the nucleic acid is DNA or RNA. In particular embodiments, the greater benefit is an overall survival benefit. In particular embodiments, the methylation status is examined in one or more genes, e.g., genes associated with the particular cancer. Specific embodiments involve methods for determining whether baseline DNA methylation levels influence overall survival in patients with cancer treated with a cytidine analog, such as 5-azacytidine or decitabine. Specific embodiments provide methods for determining whether gene promoter methylation levels influence overall survival in patients with cancer.

In one embodiment, provided herein is a method for determining whether a patient diagnosed with cancer has an increased probability of obtaining a greater benefit from treatment with a pharmaceutical composition comprising a cytidine analog by assessing the gene expression profile in the patient. In one embodiment, provided herein is a method for determining whether a patient diagnosed with cancer has an increased probability of obtaining a greater benefit from treatment with a pharmaceutical composition comprising a cytidine analog by assessing molecular markers, including one or more cell cycle markers, apoptosis markers, and DNA damage markers. In particular embodiments, the cytidine analog is 5-azacytidine. In particular embodiments, the cytidine analog is decitabine. In particular embodiments, the greater benefit is an overall survival benefit.

In certain embodiments, appropriate biomarkers may be used to determine or predict the effect of the pharmaceutical compositions comprising cytidine analogs on the disease state and to provide guidance to the dosing schedule. For example, particular embodiments herein provide a method of determining whether a patient diagnosed with a solid tumor, leukemia, lymphoma, multiple myeloma, MDS, or AML, has an increased probability of obtaining a greater benefit from treatment with a pharmaceutical composition comprising a cytidine analog by assessing the patient's nucleic acid methylation status. In particular embodiments, the cytidine analog is azacitidine. In particular embodiments, the cytidine analog is decitabine. In particular embodiments, the nucleic acid is DNA or RNA. In particular embodiments, the greater benefit is an overall survival benefit. In particular embodiments, the methylation status is examined in one or more genes, e.g., genes associated with the solid tumor, leukemia, lymphoma, multiple myeloma, MDS, or AML. Specific embodiments involve methods for determining whether baseline DNA methylation levels influence overall survival in patients treated with azacitidine. Specific embodiments involve methods for determining whether baseline DNA methylation levels influence overall survival in patients treated with decitabine. Specific embodiments provide methods for determining whether gene promoter methylation levels influence overall survival in patients.

For example, specific embodiments herein provide methods for evaluating the influence of gene methylation on prolonged survival in patients with a solid tumor (e.g., a relapsed or refractory solid tumor). In particular embodiments, such evaluation is used to predict overall survival in patients with a solid tumor, e.g., upon treatment with a pharmaceutical composition comprising a cytidine analog, as provided herein. In particular embodiments, such evaluation is used for therapeutic decision-making. In specific embodiments, such therapeutic decision-making includes planning or adjusting a patient's treatment, e.g., the dosing regimen, amount, and/or duration of administration of the cytidine analogue.

Certain embodiments provide methods of identifying individual patients diagnosed with a solid tumor having an increased probability of obtaining an overall survival benefit from cytidine analog treatment, using analysis of methylation levels, e.g., in particular genes. In some embodiments, lower levels of nucleic acid methylation are associated with an increased probability of obtaining improved overall survival following treatment with a cytidine analog. In some embodiments, higher levels of nucleic acid methylation are associated with an increased probability of obtaining improved overall survival following treatment with a cytidine analog. In some embodiments, a particular pattern or signature of nucleic acid methylation of multiple genes are associated with an increased probability of obtaining improved overall survival following treatment with a cytidine analog. In some embodiments, the increased probability of obtaining improved overall survival following treatment is at least a 5% greater probability, at least a 10% greater probability, at least a 20% greater probability, at least a 30% greater probability, at least a 40% greater probability, at least a 50% greater probability, at least a 60% greater probability, at least a 70% greater probability, at least an 80% greater probability, at least a 90% greater probability, at least a 100% greater probability, at least a 125% greater probability, at least a 150% greater probability, at least a 175% greater probability, at least a 200% greater probability, at least a 250% greater probability, at least a 300% greater probability, at least a 400% greater probability, or at least a 500% greater probability of obtaining improved overall survival following treatment, e.g., using a pharmaceutical composition comprising a cytidine analog as provided herein. In particular embodiments, the greater probability of obtaining improved overall survival following treatment is a greater probability as compared to the average probability of a particular comparison population of patients.

In particular embodiments, nucleic acid (e.g., DNA or RNA) hypermethylation status may be determined by any method known in the art. In certain embodiments, DNA hypermethylation status may be determined using the bone marrow aspirates of patients diagnosed with cancer, e.g., by using quantitative real-time methylation specific PCR ("qMSP"). In certain embodiments, the methylation analysis may involve bisulfite conversion of genomic DNA. For example, in certain embodiments, bisulfite treatment of DNA is used to convert non-methylated CpG sites to UpG, leaving methylated CpG sites intact. See, e.g., Frommer, M., et al., *Proc. Nat'l Acad. Sci. USA* 1992, 89:1827-31. Commercially available kits may be used for such bisulfite treatment. In certain embodiments, to facilitate methylation PCR, primers are designed as known in the art, e.g., outer primers which amplify DNA regardless of methylation status, and nested primers which bind to methylated or non-methylated sequences within the region amplified by the first PCR. See, e.g., Li et al., *Bioinformatics* 2002, 18:1427-31. In certain embodiments, probes are designed, e.g., probes which bind to the bisulfite-treated DNA regardless of methylation status. In certain embodiments, CpG methylation is detected, e.g., following PCR amplification of bisulfite-treated DNA using outer primers. In certain embodiments, amplified product from the initial PCR reaction serves as a template for the nested PCR reaction using methylation-specific primers or non-methylation-specific primers. In certain embodiments, a standard curve is established to determine the percentage of methylated molecules in a particular sample. Methods for detecting nucleic acid methylation (e.g., RNA or DNA methylation) are known in art. See, e.g., Laird, P. W., *Nature Rev. Cancer* 2003, 3:253-66; Belinsky, S. A., *Nature Rev. Cancer* 2004, 4:1-11.

In certain embodiments, statistical analyses are performed to assess the influence of particular methylation levels with the potential benefit of treatment with a particular pharmaceutical composition comprising a cytidine analog. In certain embodiments, the influence of methylation on overall survival is assessed, e.g., using Cox proportional hazards models and Kaplan-Meier (KM) methodology.

In certain embodiments, any gene associated with a particular solid tumor, leukemia, lymphoma, multiple myeloma, MDS, or AML may be examined for its methylation status in a patient. Particular genes associated with a solid tumor, leukemia, lymphoma, multiple myeloma, MDS, or AML, which would be suitable for use in the methods disclosed here, may be known in the art.

In specific embodiments, provided herein is a method of identifying a subject who is likely to be responsive to a treatment described herein, comprising: (a) determining the level of a biomarker in a biological sample from the subject, wherein the biomarker is described herein; and (b) comparing the level of the biomarker in the biological sample to a reference level of the biomarker; wherein the subject is likely to be responsive to the treatment if the level of the biomarker in the biological sample from the subject is altered (e.g., high or low) as compared to the reference level of the biomarker.

In specific embodiments, provided herein is a method of identifying a subject who is likely to be responsive to a treatment described herein, comprising: (a) determining the level of a biomarker in a biological sample from the subject, wherein the biomarker is described herein; (b) determining the level of the biomarker in a control sample; and (c) comparing the level of the biomarker in the biological sample from the subject to the level of the biomarker in the control sample; wherein the subject is likely to be responsive to the treatment if the level of the biomarker in the biological sample from the subject is altered (e.g., high or low) as compared to the level of the biomarker in the control sample.

In specific embodiments, provided herein is a method of identifying a subject who is likely to be responsive to a treatment described herein, comprising: (a) obtaining a biological sample from the subject; (b) determining the level of a biomarker in the biological sample, wherein the biomarker is described herein; and (c) comparing the level of the biomarker in the biological sample to a reference level of the biomarker; wherein the subject is likely to be responsive to the treatment if the level of the biomarker in the biological sample from the subject is altered (e.g., high or low) as compared to the reference level of the biomarker.

In specific embodiments, provided herein is a method of identifying a subject who is likely to be responsive to a treatment described herein, comprising: (a) obtaining a biological sample from the subject; (b) determining the level of a biomarker in the biological sample, wherein the biomarker is described herein; (c) determining the level of the biomarker in a control sample; and (d) comparing the level of the biomarker in the biological sample from the subject to the level of the biomarker in the control sample; wherein the subject is likely to be responsive to the treatment if the level of the biomarker in the biological sample from the subject is altered (e.g., high or low) as compared to the level of the biomarker in the control sample.

In specific embodiments, provided herein is a method of predicting the responsiveness of a subject to a treatment described herein, comprising: (a) determining the level of a biomarker in a biological sample from the subject, wherein the biomarker is described herein; and (b) comparing the level of the biomarker in the biological sample to a reference level of the biomarker; wherein the difference between the level of the biomarker in the biological sample from the subject and the reference level of the biomarker (e.g., higher or lower) correlates with the responsiveness of the subject to the treatment.

In specific embodiments, provided herein is a method of predicting the responsiveness of a subject to a treatment described herein, comprising: (a) determining the level of a biomarker in a biological sample from the subject, wherein the biomarker is described herein; (b) determining the level of the biomarker in a control sample; and (c) comparing the level of the biomarker in the biological sample from the subject to the level of the biomarker in the control sample; wherein the difference between the level of the biomarker in the biological sample from the subject and the level of the biomarker in the control sample (e.g., higher or lower) correlates with the responsiveness of the subject to the treatment.

In specific embodiments, provided herein is a method of predicting the responsiveness of a subject to a treatment described herein, comprising: (a) obtaining a biological sample from the subject; (b) determining the level of a biomarker in the biological sample, wherein the biomarker is described herein; and (c) comparing the level of the biomarker in the biological sample to a reference level of the biomarker; wherein the difference between the level of the biomarker in the biological sample from the subject and the reference level of the biomarker (e.g., higher or lower) correlates with the responsiveness of the subject to the treatment.

In specific embodiments, provided herein is a method of predicting the responsiveness of a subject to a treatment described herein, comprising: (a) obtaining a biological sample from the subject; (b) determining the level of a biomarker in the biological sample, wherein the biomarker is described herein; (c) determining the level of the biomarker in a control sample; and (d) comparing the level of the biomarker in the biological sample from the subject to the level of the biomarker in the control sample; wherein the difference between the level of the biomarker in the biological sample from the subject and the level of the biomarker in the control sample (e.g., higher or lower) correlates with the responsiveness of the subject to the treatment.

In specific embodiments, provided herein is a method of monitoring the efficacy of a treatment described herein, comprising: (a) obtaining a first biological sample from the subject; (b) determining the level of a biomarker in the first biological sample, wherein the biomarker is described herein; (c) administering the treatment compound to the subject; (d) thereafter obtaining a second biological sample from the subject; (e) determining the level of the biomarker in the second biological sample; and (f) comparing the levels of the biomarker in the first and second biological samples; wherein the subject is responsive to the treatment if the level of the biomarker in the second biological sample of the subject is altered (e.g., high or low) as compared to the level of the biomarker in the first biological sample of the subject.

In specific embodiments, provided herein is a method of monitoring the compliance of a subject with a treatment described herein, comprising: (a) obtaining a biological sample from the subject; (b) determining the level of a biomarker in the biological sample, wherein the biomarker is described herein; and (c) comparing the level of the biomarker with the level of the biomarker in a control sample from the subject; wherein the change in the level of the biomarker in the biological sample in comparison with the level of the biomarker in the control sample (e.g., high or low) indicates the compliance of the subject with the treatment.

3. Co-Administered Therapeutic Agents

In one embodiments, methods provided herein for treating cancer comprise co-administering a cytidine analog, such as, for example, 5-azacytidine, with one or more therapeutic agents, such as, for example, cancer therapeutic agents, to yield a synergistic therapeutic effect. In one embodiment, the co-administered therapeutic agent is provided herein above (e.g., one or more of the additional therapeutic agent described herein). In exemplary embodiments, the co-administered therapeutic agents include, but are not limited to, e.g., cytotoxic agents, anti-metabolites, antifolates, DNA intercalating agents, DNA cross-linking agents, DNA alkylating agents, DNA cleaving agents, topoisomerase inhibitors, HDAC inhibitors such as MGCD0103 (a.k.a. N-(2-aminophenyl)-4-(4-(pyridin-3-yl)pyrimidin-2-ylamino)methyl) benzamide), CDK inhibitors, JAK inhibitors, anti-angiogenic agents, Bcr-Abl inhibitors, HER2 inhibitors, EGFR inhibitors, VEGFR inhibitors, PDGFR inhibitors, HGFR inhibitors, IGFR inhibitors, c-Kit inhibitors, Ras pathway inhibitors, PI3K inhibitors, multi-targeted kinase inhibitors, mTOR inhibitors, anti-estrogens, anti-androgens, aromatase inhibitors, somatostatin analogs, ER modulators, anti-tubulin agents, vinca alkaloids, taxanes, HSP inhibitors, Smoothened antagonists, telomerase inhibitors, COX-2 inhibitors, anti-metastatic agents, immunosuppressants, biologics such as antibodies, and hormonal therapies. In particular embodiment, the co-administered therapeutic agent is thalidomide, lenalidomide, or pomalidomide. In particular embodiment, the co-administered therapeutic agent is carboplatin. In particular embodiment, the co-administered therapeutic agent is paclitaxel (e.g., Abraxane®). See, e.g., U.S. Pat. Nos. 7,758,891, 7,771,751, 7,820,788, 7,923,536, 8,034,375; U.S. Patent Publication No. 2010/0048499; all of which are incorporated herein by reference in their entireties. The co-administered agent may be dosed, e.g., orally or by injection.

In one embodiment, the route of the administration of the cytidine analog (e.g., 5-azacytidine or another cytidine analog provided herein) is independent of the route of the administration of a second therapy. In one embodiment, the cytidine analog is administered orally. In another embodiment, the cytidine analog is administered intravenously or subcutaneously. In certain embodiments, the cytidine analog is administered orally, and the second therapy is administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the cytidine analog and a second therapy are administered by the same mode of administration, e.g., orally, intravenously, or subcutaneously. In another embodiment, the cytidine analog is administered by one mode of administration, e.g., orally, whereas the second agent (e.g., an anticancer agent) is administered by another mode of administration, e.g., intravenously or subcutaneously. In yet another embodiment, the cytidine analog is administered by one mode of administration, e.g., intravenously or subcutaneously, whereas the second agent (e.g., an anticancer agent) is administered by another mode of administration, e.g., orally.

In one embodiment, each method provided herein may independently, further comprise the step of administering a second therapeutic agent. In one embodiment, the second therapeutic agent is an anticancer agent. In one embodiment, the anticancer agent is an antimetabolite, including, but not limited to, 5-fluoro uracil, methotrexate, cytarabine, high dose cytarabine, and fludarabine. In one embodiment, the anticancer agent is an antimicrotubule agent, including, but not limited to, vinca alkaloids (e.g., vincristine and vinblastine) and taxanes (e.g., paclitaxel, e.g., Abraxane®, and docetaxel). In one embodiment, the anticancer agent is an alkylating agent, including, but not limited to, cyclophosphamide, melphalan, carmustine, and nitrosoureas (e.g., hydroxyurea and bischloroethylnitrosurea). In one embodiment, the anticancer agent is a platinum agent, including, but not limited to, cisplatin, carboplatin, oxaliplatin, satraplatin (JM-216), and CI-973. In one embodiment, the anticancer agent is an anthracycline, including, but not limited to, doxrubicin and daunorubicin. In one embodiment, the anticancer agent is an anti-tumor antibiotic, including, but not limited to, mitomycin, idarubicin, adriamycin, and daunomycin (also known as daunorubicin). In one embodiment, the anticancer agent is a topoisomerase inhibitor, e.g., etoposide and camptothecins. In one embodiment, the anticancer agent is selected from the group consisting of adriamycin, busulfan, cytarabine, cyclophosphamide, dexamethasone, fludarabine, fluorouracil, hydroxyurea, interferons, oblimersen, platinum derivatives, taxol, topotecan, and vincristine.

In one embodiment, other therapies or anticancer agents that may be used in combination with the cytidine analog include surgery, radiotherapy (e.g., gamma-radiation, neutron beam radiotherapy, electron beam radiotherapy, proton therapy, brachytherapy, and systemic radioactive isotopes), endocrine therapy, biologic response modifiers (e.g., interferons, interleukins, and tumor necrosis factor (TNF)), hyperthermia and cryotherapy, agents to attenuate any adverse effects (e.g., antiemetics), and other approved chemotherapeutic drugs, including, but not limited to, alkylating drugs (mechlorethamine, chlorambucil, cyclophosphamide, melphalan, and ifosfamide), antimetabolites (cytarabine, high dose cytarabine, and methotrexate), purine antagonists and pyrimidine antagonists (6-mercaptopurine, 5-fluorouracil, cytarabine, and gemcitabine), spindle poisons (vinblastine, vincristine, vinorelbine, docetaxel, and paclitaxel, e.g., Abraxane®), podophyllotoxins (etoposide, irinotecan, and topotecan), antibiotics (daunorubicin, doxorubicin, bleomycin, and mitomycin), nitrosoureas (carmustine and lomustine), inorganic ions (cisplatin and carboplatin), enzymes (asparaginase), and hormones (tamoxifen, leuprolide, flutamide, and megestrol), imatinib, adriamycin, dexamethasone, and cyclophosphamide. For additional available cancer therapies, see, e.g., http://www.nci.nih.gov/; for a list of FDA approved oncology drugs, see, e.g., http://www.fda.gov/, The Merck Manual, 18th Ed. 2006, and PDR: Physician Desk Reference 2010, 64th Ed. 2009; the contents of each of which are hereby incorporated by reference in their entireties.

In one embodiment, without being limited by a particular theory, methylation-based silencing of specific genes limits the anti-tumor effects of cytotoxic agents. In one embodiment, without being limited by a particular theory, a cytidine analog, such as, for example, 5-azacytidine or decitabine, can sensitize tumors to the effects of chemotherapy (e.g., the effect of an anti-cancer agent). In one embodiment, without being limited by a particular theory, the epigenetic effect of a cytidine analog, such as, for example, 5-azacytidine or decitabine, restores chemo-sensitivity of cancer cells, after the cancer cells are contacted with the cytidine analog for a period of time. In certain embodiments, without being limited by a particular theory, a cytidine analog is administered to a subject in need thereof for a sustained period of time (e.g., multiple doses or multiple treatment cycles) before the subject is treated with an additional therapeutic agent (e.g., an anti-cancer agent) to yield a greater synergistic therapeutic effect and/or a reduced toxicity effect. In some embodiments, without being limited by a particular theory, co-administration of a cytidine analog and certain anti-cancer agent (e.g., a cytotoxic agent) from the first day of therapy may produce increased toxicity without added anti-tumor effects. In some embodiments, without being limited by a particular theory, sustained exposure of a subject to a cytidine analog (e.g., 5-azacytidine or decitabine or another cytidine analog provided herein) prior to the administration of an additional therapeutic agent (e.g., a cytotoxic agent) yield a synergistic therapeutic effect (e.g., sensitization of cancer cells to the cytotoxic agent).

In particular embodiments, 5-azacytidine is administered orally to a subject in need thereof at a dose of about 100 mg/day for 7 days or more before a second therapeutic agent is administered to the subject. In particular embodiments, 5-azacytidine is administered orally to a subject in need thereof at a dose of about 100 mg/day for 14 days or more before a second therapeutic agent is administered to the subject. In particular embodiments, 5-azacytidine is administered orally to a subject in need thereof at a dose of about 100 mg/day for 21 days or more before a second therapeutic agent is administered to the subject. In particular embodiments, 5-azacytidine is administered orally to a subject in need thereof at a dose of about 100 mg/day for 28 days or more before a second therapeutic agent is administered to the subject. In particular embodiments, 5-azacytidine is administered orally to a subject in need thereof at a dose of about 150 mg/day for 7 days or more before a second therapeutic agent is administered to the subject. In particular embodiments, 5-azacytidine is administered orally to a subject in need thereof at a dose of about 150 mg/day for 14 days or more before a second therapeutic agent is administered to the subject. In particular embodiments, 5-azacytidine is administered orally to a subject in need thereof at a dose of about 150 mg/day for 21 days or more before a second therapeutic agent is administered to the subject. In particular embodiments, 5-azacytidine is administered orally to a subject in need thereof at a dose of about 150 mg/day for 28 days or more before a second therapeutic agent is administered to the subject. In particular embodiments, 5-azacytidine is administered orally to a subject in need thereof at a dose of about 200 mg/day for 7 days or more before a second therapeutic agent is administered to the subject. In particular embodiments, 5-azacytidine is administered orally to a subject in need thereof at a dose of about 200 mg/day for 14 days or more before a second therapeutic agent is administered to the subject. In particular embodiments, 5-azacytidine is administered orally to a subject in need thereof at a dose of about 200 mg/day for 21 days or more before a second therapeutic agent is administered to the subject. In particular embodiments, 5-azacytidine is administered orally to a subject in need thereof at a dose of about 200 mg/day for 28 days or more before a second therapeutic agent is administered to the subject. In particular embodiments, 5-azacytidine is administered orally to a subject in need thereof at a dose of about 250 mg/day for 7 days or more before a second therapeutic agent is administered to the subject. In particular embodiments, 5-azacytidine is administered orally to a subject in need thereof at a dose of about 250 mg/day for 14 days or more before a second therapeutic agent is administered to the subject. In particular embodiments, 5-azacytidine is administered orally to a subject in need thereof at a dose of about 250 mg/day for 21 days or more before a second therapeutic agent is administered to the subject. In particular embodiments, 5-azacytidine is administered orally to a subject in need thereof at a dose of about 250 mg/day for 28 days or more before a second therapeutic agent is administered to the subject. In particular embodiments, 5-azacytidine is administered orally to a subject in need thereof at a dose of about 300 mg/day for 7 days or more before a second therapeutic agent is administered to the subject. In particular embodiments, 5-azacytidine is administered orally to a subject in need thereof at a dose of about 300 mg/day for 14 days or more before a second therapeutic agent is administered to the subject. In particular embodiments, 5-azacytidine is administered orally to a subject in need thereof at a dose of about 300 mg/day for 21 days or more before a second therapeutic agent is administered to the subject. In particular embodiments, 5-azacytidine is administered orally to a subject in need thereof at a dose of about 300 mg/day for 28 days or more before a second therapeutic agent is administered to the subject. In particular embodiments, 5-azacytidine is administered orally to a subject in need thereof at a dose of about 350 mg/day for 7 days or more before a second therapeutic agent is administered to the subject. In particular embodiments, 5-azacytidine is administered orally to a subject in need thereof at a dose of about 350 mg/day for 14 days or more before a second therapeutic agent is administered to the subject. In particular embodiments, 5-azacytidine is administered orally to a subject in need thereof at a dose of about 350 mg/day for 21 days or more before a second therapeutic agent is administered to the subject. In particular embodiments, 5-azacytidine is administered orally to a subject in need thereof at a dose of about 350 mg/day for 28 days or more before a second therapeutic agent is administered to the subject. In particular embodiments, 5-azacytidine is administered orally to a subject in need thereof at a dose of about 400 mg/day for 7 days or more before a second therapeutic agent is administered to the subject. In particular embodiments, 5-azacytidine is administered orally to a subject in need thereof at a dose of about 400 mg/day for 14 days or more before a second therapeutic agent is administered to the subject. In particular embodiments, 5-azacytidine is administered orally to a subject in need thereof at a dose of about 400 mg/day for 21 days or more before a second therapeutic agent is administered to the subject. In particular embodiments, 5-azacytidine is administered orally to a subject in need thereof at a dose of about 400 mg/day for 28 days or more before a second therapeutic agent is administered to the subject. In particular embodiments, 5-azacytidine is administered orally to a subject in need thereof at a dose of about 450 mg/day for 7 days or more before a second therapeutic agent is administered to the subject. In particular embodiments, 5-azacytidine is administered orally to a subject in need thereof at a dose of about 480 mg/day for 7 days or more before a second therapeutic agent is administered to the subject. In particular embodiments, 5-azacytidine is administered orally to a subject in need thereof at a dose of about 500 mg/day for 7 days or more before a second therapeutic agent is administered to the subject. In particular embodiments, 5-azacytidine is administered orally to a subject in need thereof at a dose of about 600 mg/day for 7 days or more before a second therapeutic agent is administered to the subject.

In one embodiment, after the second therapeutic agent is administered, the administration of the cytidine analog is continued for 1, 2, 3, 4, 5, 6, 7, 8, 9, 10, 11, 12, 14, 16, 18, 20, 22, 24, 26, 28, or more than 28 days; optionally followed with a resting period from the administration of the cytidine analog of about 1, 2, 3, 4, 5, 6, 7, 8, 9, 10, 12, 14, 21, 28, or more than 28 days.

In one embodiment, the second therapeutic agent is administered cyclically, after the first dose. In one embodiment, the methods provided herein comprise: i) administering to the subject a first daily dose of the second therapeutic agent; ii) optionally resting for a period of at least one day where the second therapeutic agent is not administered to the subject; iii) administering a second dose of the second therapeutic agent to the subject; and iv) repeating steps ii) to iii) a plurality of times. In certain embodiments, the first daily dose is between about 50 mg/m$^2$/day and about 2,000 mg/m$^2$/day. In certain embodiments, the second daily dose is between about 50 mg/m$^2$/day and about 2,000 mg/m$^2$/day. In certain embodiments, the first daily dose is between about 50 mg/m$^2$/day and about 200 mg/m$^2$/day. In certain embodiments, the second daily dose is between about 50 mg/m$^2$/day and about 200 mg/m$^2$/day. In certain embodiments, the first daily dose is between about 100 mg/day and about 1,000 mg/day. In certain embodiments, the second daily dose is between about 100 mg/day and about 1,000 mg/day. In certain embodiments, the first daily dose is higher than the second daily dose. In certain embodiments, the second daily dose is higher than the first daily dose. In certain embodiments, the second daily dose and the first daily dose are the same. In one embodiment, the rest period is 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 28 days. In one embodiment, the rest period is at least 2 days and steps ii) through iii) are repeated at least three times. In one embodiment, the rest period is at least 2 days and steps ii) through iii) are repeated at least five times. In one embodiment, the rest period is at least 3 days and steps ii) through iii) are repeated at least three times. In one embodiment, the rest period is at least 3 days and steps ii) through iii) are repeated at least five times. In one embodiment, the rest period is at least 7 days and steps ii) through iii) are repeated at least three times. In one embodiment, the rest period is at least 7 days and steps ii) through iii) are repeated at least five times. In one embodiment, the rest period is at least 14 days and steps ii) through iii) are repeated at least three times. In one embodiment, the rest period is at least 14 days and steps ii) through iii) are repeated at least five times. In one embodiment, the rest period is at least 21 days and steps ii) through iii) are repeated at least three times. In one embodiment, the rest period is at least 21 days and steps ii) through iii) are repeated at least five times. In one embodiment, the rest period is at least 28 days and steps ii) through iii) are repeated at least three times. In one embodiment, the rest period is at least 28 days and steps ii) through iii) are repeated at least five times.

In one embodiment, 5-azacytidine is administered orally for 7 days out of a 28-day cycle. In one embodiment, 5-azacytidine is administered orally for 14 days out of a 28-day cycle. In one embodiment, 5-azacytidine is administered orally for 21 days out of a 28-day cycle. In one embodiment, 5-azacytidine is administered orally for 7 days out of a 21-day cycle. In one embodiment, 5-azacytidine is administered orally for 14 days out of a 21-day cycle. In one embodiment, 5-azacytidine is administered orally for 21 days out of a 21-day cycle. In one embodiment, 5-azacytidine is administered orally once daily. In one embodiment, 5-azacytidine is administered orally twice daily. In one embodiment, 5-azacytidine is administered orally once daily in an amount of about 50 mg/day. In one embodiment, 5-azacytidine is administered orally twice daily in an amount of about 50 mg/day. In one embodiment, 5-azacytidine is administered orally once daily in an amount of about 50 mg/day for 7, 14, or 21 days. In one embodiment, 5-azacytidine is administered orally twice daily in an amount of about 50 mg/day for 7, 14, or 21 days. In one embodiment, 5-azacytidine is administered orally once daily in an amount of about 50 mg/day for more than 21 days. In one embodiment, 5-azacytidine is administered orally once daily in an amount of about 100 mg/day. In one embodiment, 5-azacytidine is administered orally twice daily in an amount of about 100 mg/day. In one embodiment, 5-azacytidine is administered orally once daily in an amount of about 100 mg/day for 7, 14, or 21 days. In one embodiment, 5-azacytidine is administered orally twice daily in an amount of about 100 mg/day for 7, 14, or 21 days. In one embodiment, 5-azacytidine is administered orally once daily in an amount of about 100 mg/day for more than 21 days. In one embodiment, 5-azacytidine is administered orally once daily in an amount of about 150 mg/day. In one embodiment, 5-azacytidine is administered orally twice daily in an amount of about 150 mg/day. In one embodiment, 5-azacytidine is administered orally once daily in an amount of about 150 mg/day for 7, 14, or 21 days. In one embodiment, 5-azacytidine is administered orally twice daily in an amount of about 150 mg/day for 7, 14, or 21 days. In one embodiment, 5-azacytidine is administered orally once daily in an amount of about 150 mg/day for more than 21 days. In one embodiment, 5-azacytidine is administered orally once daily in an amount of about 200 mg/day. In one embodiment, 5-azacytidine is administered orally twice daily in an amount of about 200 mg/day. In one embodiment, 5-azacytidine is administered orally once daily in an amount of about 200 mg/day for 7, 14, or 21 days. In one embodiment, 5-azacytidine is administered orally twice daily in an amount of about 200 mg/day for 7, 14, or 21 days. In one embodiment, 5-azacytidine is administered orally once daily in an amount of about 200 mg/day for more than 21 days. In one embodiment, 5-azacytidine is administered orally once daily in an amount of about 250 mg/day. In one embodiment, 5-azacytidine is administered orally twice daily in an amount of about 250 mg/day. In one embodiment, 5-azacytidine is administered orally once daily in an amount of about 250 mg/day for 7, 14, or 21 days. In one embodiment, 5-azacytidine is administered orally twice daily in an amount of about 250 mg/day for 7, 14, or 21 days. In one embodiment, 5-azacytidine is administered orally once daily in an amount of about 250 mg/day for more than 21 days. In one embodiment, 5-azacytidine is administered orally once daily in an amount of about 300 mg/day. In one embodiment, 5-azacytidine is administered orally twice daily in an amount of about 300 mg/day. In one embodiment, 5-azacytidine is administered orally once daily in an amount of about 300 mg/day for 7, 14, or 21 days. In one embodiment, 5-azacytidine is administered orally twice daily in an amount of about 300 mg/day for 7, 14, or 21 days. In one embodiment, 5-azacytidine is administered orally once daily in an amount of about 300 mg/day for more than 21 days. In particular embodiments, 5-azacytidine is administered continuously for 14 days, followed with a 7-day resting period.

4. Methods Comprising Co-Administering One or More Additional Therapeutic Agents with Oral Formulations Disclosed Herein Particular embodiments herein provide methods of treating diseases or disorders disclosed herein (e.g., diseases or disorders involving abnormal cell proliferation), wherein the methods comprise co-administering an oral formulation disclosed herein, such as, for example, an oral formulation comprising 5-azacytidine or another cytidine analog provided herein, with one or more additional therapeutic agents (such as, for example, a cancer therapeutic agent) to yield a synergistic therapeutic effect. Particular co-administered therapeutic agents useful in the methods disclosed herein are disclosed throughout the specification. In particular embodiments, the co-administered therapeutic agent is carboplatin. In particular embodiments, the co-administered therapeutic agent is paclitaxel (e.g., Abraxane®). In particular embodiments, the additional therapeutic agent is co-administered in an amount that is a therapeutically effective amount. In particular embodiments, the additional therapeutic agent is co-administered in a separate dosage form from the cytidine analog dosage form with which it is co-administered. In particular embodiments, the additional therapeutic agent is co-administered in a dosage form (e.g., a single unit dosage form) together with the cytidine analog with which it is co-administered. In such cases, the cytidine analog and the additional therapeutic agent may be co-formulated together in the same dosage form using methods of co-formulating active pharmaceutical ingredients, including methods disclosed herein and methods known in the art.

In particular embodiments, a cytidine analog is administered to a subject in need thereof, for a sustained period of time (e.g., for 1, 2, 3, 4, 5, 6, 7, or more than 7 days) before one or more additional therapeutic agent(s) is/are administered to the subject. In particular embodiments, provided herein are methods of treating diseases or disorders disclosed herein (e.g., diseases or disorders involving abnormal cell proliferation, such as a relapsed or refractory solid tumor), wherein the methods comprise: (i) first administering a cytidine analog orally to a subject in need thereof, for 1, 2, 3, 4, 5, 6, 7, or more than 7 days; and (ii) administering an additional therapeutic agent (e.g., an anti-cancer agent provided herein, such as, carboplatin or paclitaxel, e.g., Abraxane®) for one or more days. In certain embodiment, the second step comprises continued administration of the cytidine analog orally for one or more additional days (e.g., for 1, 2, 3, 4, 5, 6, 7, 8, 9, 10, 11, 12, 13, 14, or more than 14 days).

Incorporation By Reference: All disclosures (e.g., patents, publications, and web pages) referenced throughout this specification are incorporated by reference in their entireties.

VI. EXAMPLES

A. Example 1

Clinical studies were conducted to evaluate oral azacitidine as a single agent and in combination with Carboplatin or Abraxane® in subjects with relapsed or refractory solid tumors.

One objective of the study was to evaluate the safety and to define the Maximal Tolerated Dose (MTD) or the Maximal Administered Dose (MAD) of oral azacitidine as a single agent and in combination with carboplatin (CBDCA) or paclitaxel protein-bound particles (Abraxane® [ABX]) in subjects with relapsed or refractory solid tumors.

Other objectives of the study included: (1) to examine the impact, if any, of CBDCA or ABX on the pharmacokinetics (PK) of oral azacitidine; (2) to examine the impact, if any, of oral azacitidine on the PK of CBDCA or ABX; (3) to evaluate the pharmacodynamic (PD) effects of oral azacitidine as a single agent and in combination with CBDCA and ABX in blood, plasma and tumor tissue; and (4) to make a preliminary assessment of the anti-tumor activity of oral azacitidine as a single agent and in combination with CBDCA and ABX in specific tumor types.

Additional objectives of the study included: to determine whether there is any relationship among baseline tumor molecular characteristics (genetic or epigenetic), PD effects, and anti-tumor activity.

The study was an open-label, 3-arm, multi-center, dose-escalation study of oral azacitidine in combination with either CBDCA (Arm A), ABX (Arm B), or as a single agent (Arm C) in subjects with relapsed or refractory solid tumors (Part 1). Subjects were assigned to each study Arm at the discretion of the investigator. A minimum of 6 subjects were assigned to each study Arm when a dose level (DL) became open for enrollment. If one (1) or zero (0) out of six (6) subjects in a DL experienced dose limiting toxicity (DLT), the dose of oral azacitidine was escalated in the successive DL. A limited number of oral azacitidine DLs were explored to arrive at a recommended Part 2 dose (RP2D) of oral azacitidine for each study Arm. The RP2D may be the MTD, MAD, or a lower dose depending on the tolerability, PK, and PD observed. Part 1 was followed by expansion cohorts at the RP2D in specific tumor types (Part 2). Approximately 60 subjects were enrolled in Part 1, and approximately 100 subjects were enrolled in Part 2. Safety, efficacy, pharmacokinetics, and pharmacodynamics data were evaluated.

In Part 1, Arms A and B, Cycle 1 was 28 days in duration. Subsequent treatment Cycles were 21 days in duration. In Arm C, all Cycles were 21 days in duration.

Part 1 Design: Subjects may continue to receive their assigned combination treatment if they have no unacceptable toxicity and if there is no clinical or radiographic evidence of disease progression or the investigator deems that the subject is deriving potential benefit. If combination treatment is suspended for unacceptable toxicity that is believed to be related to CBDCA in Arm A or ABX in Arm B, subjects may continue to take single agent oral azacitidine at their assigned DL once the toxicity resolves to at least grade 1. Subjects in Arm C receive single agent oral azacitidine in all Cycles up to approximately 1 year from the start of therapy or until they experience unacceptable toxicity or progressive disease, as assessed by the investigator, whichever occurs first. Escalation of the oral azacitidine dose continues independently in each Arm until the RP2D of oral azacitidine as a single agent and in combination with CBDCA and ABX is defined. The RP2D may be different for each study Arm.

Part 2 Design: Expansion cohorts of up to 20 subjects for each of several specific tumor types are enrolled at the RP2D for each Arm. In addition to further exploring the safety and PD activity of oral azacitidine alone and in combination with CBDCA or ABX in specific tumor types, this part of the study is designed to make an initial assessment of anti-tumor activity and its potential association with candidate predictive biomarkers. Tumor biopsies are performed in Part 2.

Study Population: Men and women, 18 years or older, with histological or cytological confirmation of advanced unresectable solid tumors, including those who have progressed on (or not been able to tolerate) standard anti-cancer therapy, or for whom no other known effective therapy exists, or for those who have declined standard therapy.

Length of Study: The duration of Part 1 of the study from first subject screened to last subject last visit is approximately 1 year. Part 2 of the study lasts approximately 18 months making the entire duration of the study approximately 2.5 years.

Study Treatments:

Part 1: Subjects receive oral azacitidine as a single agent for the first 7 days of study. Beginning on Cycle 1, Day 8, subjects in Arms A and B begin combination treatment with CBDCA or ABX, respectively. Subjects may continue to receive their assigned combination until they experience disease progression or unacceptable toxicity, whichever occurs first. Subjects in Arm C receive single agent oral azacitidine in all Cycles until they experience unacceptable toxicity or progressive disease, whichever occurs first.

The dose of oral azacitidine in each Arm is escalated (or reduced) based on tolerability with a fixed dose of CBDCA or ABX in the first 28-day Cycle, or as a single agent in the first 21-day Cycle, until the RP2D is defined.

All study Arms begin at Dose Level 1 (DL1). If DL1 is declared tolerable, Dose Level 2 (DL2) opens for enrollment. If DL2 is declared tolerable, this dose and schedule are explored in Part 2 of the study. If DL2 exceeds the maximum tolerated dose (MTD), DL1 is explored in Part 2. If DL1 exceeds MTD, Dose Level-1 (DL-1) opens for enrollment.

For Arms A and B, if DL-1 is declared tolerable, Dose Level-2 (DL-2) opens for enrollment. If DL-2 is declared tolerable, this dose and schedule are explored in Part 2. If DL-2 exceeds MTD, DL-1 is explored in Part 2. If DL-1 exceeds MTD, enrollment to that Arm stops (FIG. 4).

For Arm C, if DL-1 is declared tolerable, that dose and schedule are explored in Part 2. If DL-1 exceeds MTD, DL-2 opens for enrollment. If DL-2 is declared tolerable, that dose and schedule are explored in Part 2. If DL-2 exceeds MTD, enrollment into Arm C stops (FIG. 5).

In certain embodiments, subjects receive a dose of a prophylactic anti-emetic, for example, a 5-HT3 antagonist, prior to each dose of oral azacitidine.

Part 2: Subjects in Part 2 of the study receive oral azacitidine alone (Arm C) or in combination with CBDCA (Arm A) or ABX (Arm B) according to the RP2D established for each Arm in Part 1. All treatment Cycles in Part 2 are 21 days in duration. Each specific tumor type in Part 2 receives treatment according to one of the three Arms. About 14 to 20 patients are enrolled per tumor type.

Assignment of Subject to Study Arms: At the time of enrollment in Part 1, subjects who meet all of the inclusion criteria and none of the exclusion criteria are assigned to either Arm A (oral azacitidine with CBDCA), Arm B (oral azacitidine with Abraxane®), or Arm C (single agent oral azacitidine). Assignment of subjects to each of these study Arms is at the discretion of the investigator, based on the suitability of the regimen(s) for the subject and availability of open enrollment slots. The DLs for Arms A, B, and C are shown in Table 1, Table 2, and Table 3, respectively.

Scheme 1: Overall Study Designs

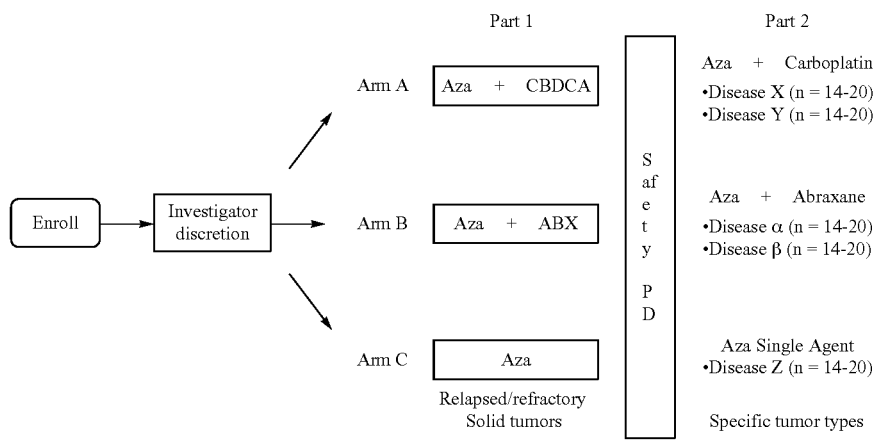

TABLE 1

Oral Azacitidine and Carboplatin (CBDCA) Dose Levels for Arm A

| | | Cycle 1 (28 days) | | Cycle 2 (21 days) | | Cycles 3+ (21 days) | |
|---|---|---|---|---|---|---|---|
| | | Oral Azacitidine | CBDCA | Oral Azacitidine | CBCDA | Oral Azacitidine | CBCDA |
| DL-2 | | 100 mg Days 1-7, 9-28 | AUC4 Day 8 | 100 mg Days 1-21 | AUC 4 Day 1 | 100 mg Days 1-21 | AUC 4 Day 1 |
| DL-1 | | 100 mg Days 1-7, 9-14, 22-28 | AUC4 Day 8 | 100 mg Days 1-7, 15-21 | AUC 4 Day 1 | 100 mg Days 1-7, 15-21 | AUC 4 Day 1 |
| DL1 | | 200 mg Days 1-7, 9-14, 22-28 | AUC4 Day 8 | 200 mg Days 1-7, 15-21 | AUC 4 Day 1 | 200 mg Days 1-7, 15-21 | AUC 4 Day 1 |
| DL2 | | 300 mg Days 1-7, 9-14, 22-28 | AUC4 Day 8 | 300 mg Days 1-7, 15-21 | AUC 4 Day 1 | 300 mg Days 1-7, 15-21 | AUC 4 Day 1 |

TABLE 2

Oral Azacitidine and Abraxane ® (ABX) Dose Levels for Arm B

| | | Cycle 1 (28 days) | | Cycle 2 (21 days) | | Cycles 3+ (21 days) | |
|---|---|---|---|---|---|---|---|
| | | Oral Azacitidine | ABX | Oral Azacitidine | ABX | Oral Azacitidine | ABX |
| DL-2 | | 100 mg Days 1-14, 19-28 | 100 mg/m² Days 8, 15 | 100 mg Days 1-21 | 100 mg/m² Days 1, 8 | 100 mg Days 1-21 | 100 mg/m² Days 1, 8 |
| DL-1 | | 100 mg Days 1-14, 22-28 | 100 mg/m² Days 8, 15 | 100 mg Days 1-7, 15-21 | 100 mg/m² Days 1, 8 | 100 mg Days 1-7, 15-21 | 100 mg/m² Days 1, 8 |
| DL1 | | 200 mg Days 1-14, 22-28 | 100 mg/m² Days 8, 15 | 200 mg Days 1-7, 15-21 | 100 mg/m² Days 1, 8 | 200 mg Days 1-7, 15-21 | 100 mg/m² Days 1, 8 |
| DL2 | | 300 mg Days 1-14, 22-28 | 100 mg/m² Days 8, 15 | 300 mg Days 1-7, 15-21 | 100 mg/m² Days 1, 8 | 300 mg Days 1-7, 15-21 | 100 mg/m² Days 1, 8 |

TABLE 3

Oral Azacitidine Dose Levels for Arm C

|      | Cycle 1 (21 days) | Cycle 2 (21 days) Oral Azacitidine | Cycles 3+ (21 days) |
|------|-------------------|-------------------------------------|---------------------|
| DL-2 | 200 mg, Days 1-14 | 200 mg, Days 1-14                   | 200 mg, Days 1-14   |
| DL-1 | 300 mg, Days 1-14 | 300 mg, Days 1-14                   | 300 mg, Days 1-14   |
| DL1  | 200 mg, Days 1-21 | 200 mg, Days 1-21                   | 200 mg. Days 1-21   |
| DL2  | 300 mg, Days 1-21 | 300 mg, Days 1-21                   | 300 mg. Days 1-21   |

Efficacy Assessments: Subjects are evaluated for tumor response after Cycle 2 and every other Cycle thereafter. The primary efficacy variables are tumor response at the end of treatment, and the proportion of subjects alive and progression-free (progression-free survival; PFS) at the end of Cycle 6. Tumor response is based on Response Evaluation Criteria in Solid Tumors (RECIST) 1.1 for disease states which require at least one measurable target lesion at baseline for study eligibility. Progression-free survival rates are computed using the Kaplan-Meier estimates. Duration of response is reported in subjects who have a complete or partial response. Ninety percent confidence intervals (90% CIs) of the response rate at the end of treatment, and of the PFS rate at time of each scheduled response assessment (i.e., Cycles 2, 4, 6, etc.) are provided by tumor type. Other endpoints that are explored include time-to-tumor-progression and overall survival.

The influence of major disease characteristics and prognostic indications are considered in relationship to efficacy, with special attention given to subjects in Arm A who were previously treated with a platin and to subjects in Arm B who were previously treated with a taxane. Full details on the efficacy analysis are given in the Statistical Analysis Plan (SAP).

Safety Assessments: Safety assessments include adverse events (AEs), physical examinations (PEs), (including height and body weight); vital signs (including systolic/diastolic blood pressure [BP], pulse rate, respiratory rate, and oral temperature); Eastern Cooperative Oncology Group (ECOG) performance status; 12-lead electrocardiogram (ECG [including rhythm, heart rate, PR, QRS, and QT intervals]); complete blood count (CBC) (including hemoglobin, hematocrit, red blood cell count with indices mean corpuscular volume {MCV}, mean corpuscular hemoglobin {MCH}, and mean corpuscular hemoglobin concentration {MCHC}, white blood cell [WBC] count with absolute differential [neutrophils, lymphocytes, monocytes, eosinophils, and basophils], and platelet count); coagulation (international normalized ratio [INR], prothrombin time [PT], and partial thromboplastin time [PTT]); serum chemistry (non-fasting) (including albumin, alkaline phosphatase, bicarbonate, blood urea nitrogen [BUN], calcium, chloride, creatinine, glucose, lactic dehydrogenase [LDH], phosphorus, potassium, aspartate aminotransferase [AST], alanine aminotransferase [ALT], sodium, total bilirubin, total protein, and uric acid); screening serum pregnancy test required for all females of child-bearing potential (FCBP) prior to Cycle 1 Day 1 dosing (test result must be obtained and read prior to dosing on Day 1.); tumor biopsy (optional); and tumor assessment.

Study Endpoints: The nature, incidence and severity of AEs are evaluated using the National Cancer Institute Common Terminology Criteria for Adverse Events (NCI CTCAE) criteria, Version 4.0. For oral azacitidine, CBDCA, and ABX (administered alone and in combination), the following plasma PK parameters are assessed: (1) maximum observed concentration in plasma ($C_{max}$); (2) area under the concentration-time curve (AUC); (3) time to maximum concentration ($t_{max}$); (4) terminal half-life ($t_{1/2}$); (5) apparent total body clearance (CL/F); and (6) apparent volume of distribution (Vz/F). To evaluate the PD effects of oral azacitidine in blood, plasma, and tumor tissue, the following endpoints are collected: (1) change from baseline (Cycle 1 Day 1 pre-dose) in DNA methylation (global and gene-specific assays) in whole blood and tumor tissue (as available in Part 1); (2) reduction from baseline (Cycle 1 Day 1 predose) in DNMT1 protein levels in tumor tissue (as available in Part 1). Anti-tumor activity endpoints using tumor-specific response criteria for each tumor type include: (1) response rate and duration of response; and (2) progression-free survival (PFS). Molecular characteristics of the blood and tumor, including, but not limited to, DNA/RNA methylation, gene sequence and mRNA/miRNA expression, may be evaluated at baseline and post-therapy for examination in relation to tumor responses.

Part 1/Arm A: Subjects in Arm A receive their first dose of oral azacitidine at their assigned DL in the clinic on Cycle 1 Day 1 along with PK (predose through 8 hours post-dose oral azacitidine) and predose PD blood (mandatory) and tumor (optional) sampling. On Days 2 through 7, subjects self-administer oral azacitidine daily according to their assigned DL. Subjects return to the clinic for CBDCA dosing on Day 8 along with predose PD sampling (blood). CBDCA is administered at AUC=4 using the Glomerular Filtration Rate (GFR) calculation from the Modification of Diet in Renal Disease (MDRD) formula below as an i.v. infusion over 1 hour.

Modification of Diet in Renal Disease (MDRD) Equation for GFR: This IDMS-traceable MDRD study equation calculator is for use with Scr reported in mg/dL:

$$GFR(mL/min/1.73\ m^2) = 175 \times (S_{cr})^{-1.154} \times (Age)^{-0.203} \times (0.742\ if\ female) \times (1.212\ if\ African\ American)$$
(conventional units)

The equation does not require weight because the results are reported normalized to 1.73 m² body surface area (BSA), which is an accepted average adult surface area.

$$CBDCA\ dose(mg) = 4\ (GFR+25)$$

An on-line calculator can be found at the following link: http://www.nkdep.nih.gov/professionals/gfr_calculators/idms_con.htm In some embodiments, oral azacitidine is not administered on Day 8 so that the PK profile of CBDCA alone can be established. On Day 9, subjects return to the clinic for CBDCA PK sampling approximately 24 hours after the end of the initial infusion and before administration of oral azacitidine. On Day 9, subjects receive their dose of oral azacitidine at their assigned DL in the clinic. On Days 10 through 14, subjects self-administer oral azacitidine. Subjects return to the clinic on Cycle 1 Day 15 for blood PD sampling (mandatory) and tumor biopsy (optional). On Days 15 through 21 no study medication is administered (except for subjects in DL-2, who self-administer oral azacitidine daily). On Day 22, subjects return to clinic for administration of oral azacitidine with predose blood collection (mandatory) for PD analysis. On Days 23 through 28 of Cycle 1, subjects self-administer oral azacitidine daily according to their assigned DL (FIG. 1).

Subjects who complete Cycle 1 meet the following hematologic criteria at the beginning of each subsequent Cycle: (1) ANC>1.5×10⁹ L; and (2) Platelets>75×10⁹/L.

If the hematologic criteria are not met, the start of Cycle 2 may be delayed for up to 7 days to allow the counts to recover. If recovery has not occurred after 7 days, this is considered a DLT.

In Cycle 2, Arm A subjects receive oral azacitidine in the clinic on Day 1 followed by CBDCA AUC=4 as an i.v. infusion over 1 hour, along with PK (predose through 8 hours following the end of the CBDCA infusion). On Day 2, subjects return to the clinic for PK sampling approximately 24 hours following the end of the CBDCA infusion. On Days 2 through 7, subjects self-administer oral azacitidine daily according to their assigned DL. On Days 8 through 14 of Cycle 2, no study medication is administered (except for subjects in DL-2 who self-administer oral azacitidine at their assigned DL). On Days 15 through 21, subjects self-administer oral azacitidine at their assigned DL.

In Cycles 3 and beyond, Arm A subjects receive oral azacitidine at their assigned DL in the clinic on Day 1 followed by CBDCA AUC=4 as an i.v. infusion over 1 hour. On Days 2 through 7, subjects self-administer oral azacitidine daily according to their assigned DL. On Days 8 through 14, no study medication is administered (except for subjects in DL-2 who self-administer oral azacitidine at their assigned DL). On Days 15 through 21, subjects self-administer oral azacitidine at their assigned DL. Subjects may continue to receive their assigned combination treatment if they have no unacceptable toxicity and if there is no clinical or radiographic evidence of disease progression or they are deriving potential benefit as assessed by the investigator. If combination treatment is suspended for unacceptable toxicity that is believed to be related to CBDCA, subjects may continue to take single agent oral azacitidine at their assigned DL once the toxicity resolves.

Part 1/Arm B: Subjects in Arm B receive their first dose of oral azacitidine at their assigned DL in the clinic on Cycle 1 Day 1 along with PK (predose through 8 hours post-dose oral azacitidine) and PD blood sampling. Tumor biopsy (optional) is obtained prior to the first dose of oral azacitidine on Day 1. On Days 2 through 7, subjects self-administer oral azacitidine daily according to their assigned DL. Subjects return to the clinic on Day 8 for oral azacitidine followed by ABX 100 mg/m$^2$ i.v., along with PK (predose through approximately 8 hours post end of ABX infusion) and predose PD blood sampling. Subjects return to the clinic on Days 9, 10 and 11 for ABX PK sampling approximately 24, 48 and 72 hours from the end of the ABX infusion. On Days 9 through 14, subjects self-administer oral azacitidine at their assigned DL. On Cycle 1 Day 15, subjects report to the clinic for blood PD sampling (mandatory) and tumor biopsy (optional). Abraxane® 100 mg/m$^2$ i.v is administered on Cycle 1 Day 15 followed by PK sampling (predose through approximately 8 hours after the end of the ABX infusion). Subjects return to the clinic on Days 16, 17, and 18 for ABX PK sampling approximately 24, 48 and 72 hours from the end of the ABX infusion. On Days 15 through 21, no oral azacitidine is administered (except for subjects assigned to DL-2 who self-administer oral azacitidine daily according to their assigned DL on Days 19 through 21). In some embodiments, oral azacitidine is not administered on Days 15 through 18 of Cycle 1 for subjects in DL-2 so that the PK profile of ABX alone can be established. On Day 22, subjects return to the clinic for oral azacitidine followed by ABX 100 mg/m$^2$ i.v. in the clinic after obtaining predose blood (mandatory) PD sampling. On Days 23 through 28, subjects self-administer oral azacitidine daily according to their assigned DL (FIG. 2).

Subjects who complete Cycle 1 meet the following hematologic criteria at the beginning of each subsequent Cycle: (1) Absolute Neutrophil Count (ANC)>1.5×10$^9$/L; and (2) Platelets>75×10$^9$/L.

If the hematologic criteria are not met, the start of Cycle 2 may be delayed for up to 7 days to allow the hematologic counts to recover. If recovery has not occurred after 7 days, this is considered a DLT.

In Cycle 2, Arm B subjects receive oral azacitidine followed by ABX 100 mg/m$^2$ i.v on Day 1. On Days 2 through 7, subjects self-administer oral azacitidine at their assigned DL. Subjects return to the clinic on Day 8 for ABX 100 mg/m$^2$ i.v. In some embodiments, oral azacitidine is not administered on Days 8 through 14 (except for subjects in DL-2 who self-administer oral azacitidine at their assigned DL). Oral azacitidine followed by ABX 100 mg/m$^2$ i.v. is administered on Day 15. On Days 16 through 21, subjects self-administer oral azacitidine at their assigned DL. Subjects who complete Cycle 2 without unacceptable toxicity and without objective evidence of disease progression as per a tumor assessment may proceed to Cycle 3.

In Cycle 3 and beyond, Arm B subjects receive oral azacitidine at their assigned DL in the clinic on Day 1, followed by ABX 100 mg/m$^2$ i.v. On Days 2 through 7, subjects self-administer oral azacitidine at their assigned DL. Subjects return to the clinic on Day 8 for ABX 100 mg/m$^2$ i.v. In some embodiments, oral azacitidine is not administered on Days 8 through 14 (except for subjects in DL-2 who self-administer oral azacitidine at their assigned DL). Oral azacitidine followed by ABX 100 mg/m$^2$ i.v. is administered on Day 15 in the clinic. On Days 16 through 21, subjects self-administer oral azacitidine at their assigned DL. Subjects may continue to receive their assigned combination treatment if they have no unacceptable toxicity and if there is no clinical or radiographic evidence of disease progression. If combination treatment is suspended for unacceptable toxicity that is believed to be related to ABX, subjects may continue to take single agent oral azacitidine at their assigned DL once the toxicity resolves.

Part 1/Arm C: Subjects in Arm C receive their first dose of oral azacitidine at their assigned DL in the clinic on Cycle 1 Day 1. Predose tumor collection (optional) accompanies oral azacitidine on Cycle 1 Days 1 and 15. Pre-dose PD blood collection (mandatory) accompanies oral azacitidine dosing on Cycle 1 Days 1, 8, and 15 and Cycle 2 Day 1. On Days 2 through 7, 9 through 14 and 16 through 21 of each Cycle, subjects self-administer oral azacitidine at their assigned DL; subjects in DL-1 and DL-2 only self-administer oral azacitidine Days 2 through 7 and 9 through 14 (FIG. 3).

In Cycle 2 and beyond, Arm C subjects self-administer oral azacitidine on Days 2 through 21; subjects in DL-1 and DL-2 only self-administer oral azacitidine on Days 2 through 14. Subjects who complete Cycle 2 without unacceptable toxicity and without objective evidence of disease progression on a tumor assessment may proceed to Cycle 3. Subjects may continue to receive oral azacitidine at their assigned DL as long as they have no unacceptable toxicity and no clinical or radiographic evidence of disease progression.

DLT Definitions: Any non-hematologic toxicity of NCI CTCAE v 4.0 Grade=3 that is believed to be related to oral azacitidine or to the combination of oral azacitidine with CBDCA or ABX with the following exceptions: (1) Grade 3 emesis that responds to optimal antiemetic therapy within 72 hours; (2) Grade 3 diarrhea that responds to optimal medical management within 72 hours; (3) Alopecia of any grade; (4) Grade 3 fatigue in a subject who had Grade 2 fatigue at study entry and that recovers to baseline grade or less within 72 hours; and (5) Grade 3 or 4 laboratory abnormalities that are not accompanied by clinical signs or symptoms and are not believed by the investigator to be medically significant.

The following hematologic toxicities are considered DLT: (1) Grade 4 neutropenia lasting>7 days or accompanied by fever; (2) Grade 3 thrombocytopenia with clinically significant bleeding; and (3) Failure to meet hematologic criteria for starting Cycle 2 within 7 days of Cycle 1 Day 28.

Definition of DLT-Evaluable Subjects: To be evaluable for DLT for the purpose of dose escalation decisions, a subject must meet one of the following conditions: (1) Experienced a DLT during Cycle 1; or (2) Did not receive Cycle 2 Day 1 treatment due solely to not meeting hematologic criteria within 7 days of Cycle 1 Day 28 (for Arm C subjects, Cycle 1 Day 21); or (3) Completed dosing for Cycle 1 Day 28 (for Arm C subjects, Cycle 1 Day 21) without DLT and (i) missed no more than 4 total planned doses of oral azacitidine within Cycle 1; (ii) Arm A subjects: received scheduled dose of CBDCA during Cycle 1; and (iii) Arm B subjects: received all scheduled doses of ABX during Cycle 1.

Subjects who do not meet any of the criteria for being DLT evaluable (e.g., who withdraw from study prior to the end of Cycle 1 for reasons other than DLT) are replaced so that dose escalation decisions can be based on a minimum of 6 DLT-evaluable subjects.

Part 2: Once the RP2D and schedule have been determined for oral azacitidine as a single agent and in combination with CBDCA and/or ABX in Part 1, enrollment of Part 2 of the study begins. One objective of Part 2 is to further define the safety, PK, and PD of oral azacitidine combinations with CBDCA and/or ABX and as a single agent in subjects with particular tumor types and to explore candidate predictive biomarkers of anti-tumor activity. Up to 2 tumor types are examined for each Arm of the study. The definitive selection of tumor types evaluated in Part 2 are determined by any antitumor signal observed in Part 1. For each tumor type, enrollment proceeds in a 2-stage fashion. For each Arm, if at least 2 objective responses are seen by Cycle 6 in the first 14 subjects, an additional 6 subjects are enrolled for a total of 20 subjects. If none of the first 14 subjects has an objective response, no further subject is enrolled.

PD and Predictive Biomarkers: One objective of this study is to identify a dose and schedule of oral azacitidine that is not only safe but that exhibits pharmacologic activity. Methylation changes in nucleated blood cells can provide confirmation that a dose is pharmacologically active and can help distinguish which dose and schedule shows the most compelling pharmacologic activity.

Predictive biomarkers can allow prospective identification of patients who are likely to benefit clinically from the combination of oral azacitidine as a single agent or combined with CBDCA or ABX. The PD and predictive biomarkers analyzed in this study (e.g., Part 1 or Part 2 of the study) are shown in Table 4.

TABLE 4

| PD and Predictive Biomarker Studies | | | | |
|---|---|---|---|---|
| Tissue | Analyte | Assay | PD[a] | Pred[b] |
| Whole Blood (PBMC) | Genomic DNA | Global Methylation Analysis | X | |
| | RNA | Global Methylation Analysis | X | |
| Plasma | Free DNA | Candidate Gene Methylation Analysis | X | X |
| Tumor (Fresh Frozen) | Genomic DNA | Global Methylation Analysis | X | X |
| | | Candidate Gene Methylation Analysis | X | X |
| | RNA | Global Methylation Analysis Candidate Gene Methylation Analysis | X | X |
| Tumor (FFPE) | Protein (IHC) | DNMT1 | X | X |
| | | Candidate Short Half-Life Proteins, DNA Damage, Apoptosis Markers | X | X |

[a]Change from pre-treatment to Cycle 1 Day 7
[b]Baseline profile and change from pre-treatment to Cycle 1 Day 7

Dosage Forms and Study Treatments: Oral azacitidine is provided as 100 mg tablets for oral administration, for example, supplied by Celgene Corporation. See, e.g., U.S. Patent Publication No. 2009/0286752 (application Ser. No. 12/466,213), which is incorporated herein in its entirety.

Abraxane® is provided in single-use vials, for example, supplied by Celgene Corporation. Each single-use 50 mL vial contains 100 mg paclitaxel and human albumin (HA) as a stabilizer. Unreconstituted ABX is stored at controlled room temperature (25° C. or 77° F.; excursions permitted to 15-30° C.). Reconstituted ABX is refrigerated at 2° C. to 8° C. (36° F. to 46° F.) and used within 8 hours. Both forms are stored in an area free of environmental extremes.

CBCDA may be obtained as a commercially available product through a hospital pharmacy or licensed distributor.

Each dose of oral azacitidine is taken with 8 ounces (240 mL) of room temperature water. Oral azacitidine may be taken on an empty stomach or with food. If the dose is taken in the morning, subjects may consume their usual breakfast before or after administration.

No adjustment of the oral azacitidine dose is allowed during Cycle 1. Oral azacitidine may be held for up to 7 days between the end of Cycle 1 and the start of Cycle 2 (to allow hematologic criteria) for Cycle 2 to begin. For subjects who experience unacceptable toxicity after the start of Cycle 2, oral azacitidine may be held for up to 7 days or until the toxicity recovers to grade 1 or less. If recovery has not occurred after 7 days, dosing is permanently discontinued. Subjects who recover within the 7 day period may resume dosing at a reduced dose on the planned Cycle day (i.e., missed doses are not made up). For the first episode of unacceptable toxicity in Cycle 2 or a later Cycle, if the subject recovers within 7 days of cessation of dosing with oral azacitidine and had previously been receiving 300 mg of oral azacitidine, the subject may resume dosing at a dose of 200 mg. If the subject had previously been receiving 200 mg of oral azacitidine, the subject may resume at a dose of 100 mg. Subjects who experience unacceptable toxicity after Cycle 2 at a dose of 100 mg may resume dosing at the same dose if they recover within 7 days of dosing cessation.

For the second episode of unacceptable toxicity after Cycle 2, if the subject recovers within 7 days of cessation of dosing and had previously been receiving 200 mg of oral azacitidine, the subject may resume dosing at a dose of 100 mg. For subjects on reduced doses of oral azacitidine, the dose may be re-escalated (one dose level at a time) to their originally assigned DL provided they have not experienced unacceptable toxicity in 2 consecutive Cycles.

If, prior to the second episode of unacceptable toxicity, the subject had been receiving 100 mg of oral azacitidine, dosing is permanently discontinued. Any subject who experiences a third episode of unacceptable toxicity on a reduced dose of oral azacitidine discontinues dosing permanently. No intra-subject dose escalation beyond the dose originally prescribed is allowed.

For the purposes of dose adjustment, unacceptable toxicity is defined as any AE that is deemed by the investigator to be related to oral azacitidine and/or to the combination of oral azacitidine with CBDCA or ABX and that poses a medical risk or substantial discomfort to the subject including but not limited to Grade 3 or 4 hematologic or non-hematologic toxicity. If the unacceptable toxicity is believed by the investigator to be more likely to be associated with the backbone agent (e.g., neuropathy with ABX), the subject may continue on single agent oral azacitidine.

Administration of Oral Azacitidine: Subjects are advised not to consume any grapefruit/grapefruit juice during the study, beginning 3 days prior to Cycle 1 Day 1. Subjects drink 8 ounces (240 mL) of room temperature water with each dose. Oral azacitidine may be taken on an empty stomach or with food. If the dose is taken in the morning, subjects may consume their usual breakfast before or after administration. The breakfast meal is not to exceed 600 calories; however, the actual calorie count need not be measured or recorded. If a meal other than breakfast is consumed, a light meal (not more than 25% of a subject's usual daily calories) may be eaten before or after dose administration.

On days when subjects are not in the clinic, subjects take oral azacitidine at home. Subjects are given sufficient quantity of oral azacitidine for the dosing days at home. Subjects are instructed to inspect each oral azacitidine tablet and only take tablets that are totally intact. Subjects are instructed to return any tablet found to not be intact. Subjects are instructed to record the date and time of oral azacitidine administration in a Diary Card. On days when oral azacitidine is taken at home or on days when PK samples are not collected during the clinic visit, subjects are encouraged to ingest oral azacitidine on an empty stomach or with food, with 8 ounces (240 mL) of room temperature water.

Study Results: In one embodiment, in Part 1, Arm A of the study, 5-azacytidine was dosed from Day 1 to Day 14 and CBDCA was dosed on Day 8 at AUC 4, in a 21-day cycle. Safety and PD were analyzed. In one embodiment, certain patients were dosed with 5-azacytidine at a dose of 200 mg from Day 1 to Day 14 and CBDCA at a dose of AUC 4 on Day 8, in a 21-day cycle, to treat cancers, such as, NSCLC (non-small cell lung cancer), sarcoma, CRC (colorectal cancer), melanoma, ovarian cancer, or cervical cancer. In one embodiment, certain patients were dosed with 5-azacytidine at a dose of 300 mg from Day 1 to Day 14 and CBDCA at a dose of AUC 4 on Day 8, in a 21-day cycle, to treat cancers, such as, mesothelioma, endometrial cancer, merkel cell cancer, melanoma, chodrosarcoma, NSCLC, or HNSCC (head and neck squamous cell carcinoma).

In one embodiment, in Part 1, Arm B of the study, 5-azacytidine was dosed from Day 1 to Day 14 and ABX was dosed on Days 8 and 15 at 100 mg/m$^2$, in a 21-day cycle. Safety and PD were analyzed. In one embodiment, certain patients were dosed with 5-azacytidine at a dose of 200 mg from Day 1 to Day 14 and ABX at a dose of 100 mg/m$^2$ on Days 8 and weekly thereafter, in a 21-day cycle, to treat cancers, such as, endometrial cancer, pancreatic cancer, ovarian cancer, or breast cancer. Partial responses were observed in endometrial cancer and pancreatic cancer (e.g., metastatic pancreatic cancer). For example, in one patient with metastatic pancreatic cancer, after Cycle 2, CA19-9 level was decreased from 1867 to 15, and partial response was observed for seven months or more. One patient with endometrial cancer progressed 8 months on the study after 5 cycles of Carbo/Taxol, with no evidence of disease at primary site. In one embodiment, certain patients were dosed with 5-azacytidine at a dose of 200 mg from Day 1 to Day 14 and ABX at a dose of 100 mg/m$^2$ on Days 8 and 15, in a 21-day cycle, to treat cancers, such as, pancreatic cancer, cholangio cancer, HNSCC, CRC, or ovarian cancer. In one embodiment, certain patients were dosed with 5-azacytidine at a dose of 300 mg from Day 1 to Day 14 and ABX at a dose of 100 mg/m$^2$ on Days 8 and 15, in a 21-day cycle, to treat cancers, such as, cholangio cancer, pancreatic cancer, or cervical cancer. Partial responses were observed in cervical cancer.

In one embodiment, in Part 1, Arm C of the study, 5-azacytidine was dosed from Day 1 to Day 21, in a 21-day cycle (continuous). Safety and PD were analyzed. In one embodiment, certain patients were dosed with 5-azacytidine at a dose of 200 mg from Day 1 to Day 21, in a 21-day cycle, to treat cancers, such as, CRC, head and neck cancer, or GIST (gastrointestinal stromal tumor). In one embodiment, certain patients were dosed with 5-azacytidine at a dose of 300 mg from Day 1 to Day 21, in a 21-day cycle, to treat cancers, such as, CRC, NSCLC, or NP (nasopharyngeal) cancer. Partial responses were observed in nasopharyngeal cancer.

Additional clinical efficacy observed in Part 1 of the study are summarized below:

| ARM | AZA Dose | Tumor | Response | Time on Study | Prior Regimens (best response, months on Rx) |
|---|---|---|---|---|---|
| Arm A (AZA + CBDCA) | 200 mg | NSCLC | SD | >7 mo | Erlotinib + bevacizumab (SD 16 mo) |
| | 200 mg | Sarcoma | SD | >7 mo | Dox/Ifos (SD 3 mo) Gem/Taxotere (PD 2 mo) |
| | 300 mg | Endometrial | CA-125 ↓ >100% | >4 mo | Carbo/Taxol (SD 5 mo) |
| Arm B (AZA + ABX) | 200 mg | Pancreatic | Mixed response | >3 mo | Gem/Reolysin (SD 8 mo) |
| | 200 mg | Endometrial | PR | ~8 mo | Carbo/Taxol (SD 3 mo) CC-122 (PD 1 mo) |
| | 200 mg | Pancreatic | PR | >7 mo | Gem (SD 7 mo) |
| | 200 mg | Pancreatic | CA 19-9 ↓ >50% | ~4 mo | Gem (PD 3 mo) Tivantinib/erlotinib (PD 1 mo) |
| | 200 mg | Colorectal | 28% ↓ target | >3 mo | 5FU/Leuc/bev (2 mo) refractory to prior treatment |
| | 200 mg | Ovarian | CA 125 ↓ >50% | >2 mo | — |
| Arm C (AZA) | 300 mg | Nasopharyngeal | PR | >3 mo | 5FU/cisplat (PR 5 mo) Erbitux (PD 3 mo) |

In one embodiment, in Part 2, Arm A of the study, 5-azacytidine was dosed orally, e.g., at 300 mg (on Days 1 to 14 of a 21-day cycle), and CBDCA was dosed, e.g., at AUC 4, to treat patients with solid tumor, such as relapsed and refractory bladder cancer (e.g., bladder carcinoma, or urothelial malignancies) or relapsed and refractory ovarian cancer (e.g., epithelial ovarian carcinoma). Tissue samples are analyzed to evaluate activity and efficacy.

In one embodiment, in Part 2, Arm B of the study, 5-azacytidine was dosed orally, e.g., at 200 mg (on Days 1 to 14 of a 21-day cycle), in combination with ABX (e.g., at a dose of 100 mg/m$^2$), to treat patients with solid tumor, such as relapsed and refractory NSCLC (non-small cell lung cancer) or relapsed and refractory pancreatic cancer. Tissue samples are analyzed to evaluate activity and efficacy.

In one embodiment, in Part 2, Arm C of the study, 5-azacytidine was dosed alone (e.g., orally at a dose of 200 mg or 300 mg on Days 1 to 14 of a 21-day cycle) to treat patients with solid tumor, such as relapsed and refractory colorectal cancer. Tissue samples are analyzed to evaluate activity and efficacy.

B. Example 2

DNA methylation is employed as a biomarker to monitor responses in patients treated with azacitidine in the clinical studies described herein. Analysis is performed with an Infinium Assay (commercially available from Illumina, Inc., San Diego, Calif.). The Infinium Assay combined with Bead-Chips allows large-scale interrogation of variations in the human genome. For example, the Infinium HumanMethylation27 BeadChip enables interrogation of 27,578 CpG loci, covering over 14,000 genes. The DNA Methylation Assay protocol includes the following steps: (1) bisulfite conversion; (2) DNA amplification; (3) DNA fragmentation; (4) DNA precipitation; (5) DNA hybridization to BeadChip; (6) extension and staining on BeadChip; and (7) imaging of BeadChip. In other embodiments, DNA methylation assay with 450K array (instead of 27K array) is used.

The assay for methylation is used to detect methylation status at individual CpG loci by typing bisulfite-converted DNA. Methylation protected C from conversion, whereas unmethylated C is converted to T. A pair of bead-bound probes is used to detect the presence of T or C by hybridization followed by single-base extension with a labeled nucleotide. Up to twelve samples are profiled in parallel. Blood samples were collected and DNA methylation was analyzed in parallel. In other embodiments, bone marrow samples are collected and DNA methylation analyzed in parallel.

Methylation of plasma DNA and PBMC DNA of patients from Part I of the clinical study exemplified in Example 1 was analyzed.

C. Example 3

Clinical studies are conducted to assess the ability of an oral formulation comprising a cytidine analog, such as 5-azacytidine, to treat patients having lung cancer, e.g., non-small-cell lung cancer (NSCLC). Such studies may include, e.g., an assessment of the ability to stop or reverse the growth of particular NSCLC cell types in patients having NSCLC). In certain clinical studies, patients are tested for particular NSCLC cell types, prior to administration of the oral formulation. In certain clinical studies, patients with cell types known or believed to benefit preferentially from cytidine analog (e.g., 5-azacytidine) administration may be enrolled. In certain clinical studies, patients having NSCLC are enrolled without analysis of particular NSCLC cell type. In certain clinical studies, patients having any type of NSCLC cells are candidates for treatment with an oral formulation provided herein.

In certain clinical studies, patients from any of the three main NSCLC groups may be enrolled, i.e., (1) patients with tumors that are surgically resectable; (2) patients with either locally or regionally advanced lung cancer; or (3) patients with distant metastases at the time of diagnosis. In certain clinical studies, patients may be currently undergoing additional treatment for NSCLC, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein. The additional therapeutic agent(s) may be administered in the same oral formulation as the cytidine analog, or may be co-administered (e.g., via PO, SC or IV administration) in combination with an oral formulation comprising the cytidine analog. The appropriate amount and dosing schedule for an additional therapeutic agent may be determined for a particular patient using methods known in the art.

In particular embodiments, the co-administered agent is carboplatin. In particular embodiments, the co-administered agent is paclitaxel (e.g., Abraxane®).

An association between gene methylation and recurrence of NSCLC tumors is known in the art. See, e.g., M. V. Brock et al., *N. Engl. J. Med.*, 2008, 358(11):1118-28. Accordingly, in certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In certain clinical studies, patients with high levels of DNA methylation (e.g., CpG island methylation) of certain genes may be administered a cytidine analog (e.g., 5-azacytidine). In certain clinical studies, patients with low levels of DNA methylation (e.g., CpG island methylation) of certain genes may be administered a cytidine analog (e.g., 5-azacytidine). In certain clinical studies, patients with a particular DNA methylation signature (e.g., CpG island methylation) of certain genes may be administered a cytidine analog (e.g., 5-azacytidine). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349: 2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the stage and progression of the patient's NSCLC, the patient's age and weight, the patient's prior treatment regimens, and other variables, as known in the art. In certain clinical studies, potential starting doses may be, e.g., about 50 mg, about 60 mg, about 70 mg, about 75 mg, about 80 mg, about 90 mg, about 100 mg, about 120 mg, about 140 mg, about 150 mg, about 160 mg, about 180 mg, about 200 mg, about 220 mg, about 240 mg, about 250 mg, about 300 mg, about 350 mg, about 360 mg, about 400 mg, about 420 mg, about 450 mg, about 480 mg, about 500 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. Cycles may be repeated as desired, e.g., over a period of one or more months, as disclosed herein. After a certain number of cycles, the dosage may be increased to increase the beneficial effect, provided such an increase does not cause undesirable toxicity effects. Patients may be treated for a minimum number of cycles, as disclosed herein. Complete or partial response may require additional treatment cycles. Treatment may be continued as long as the patient continues to benefit.

D. Example 4

Clinical studies are conducted to assess the ability of an oral formulation comprising a cytidine analog, such as 5-azacytidine, to treat patients having an ovarian cancer (including, e.g., the ability to stop or reverse the growth of cancer cells in patients having an ovarian cancer). Particular ovarian cancers include, but are not limited to, ovarian epithelial cancer, ovarian germ cell tumors, and ovarian low malignant potential tumors. In certain clinical studies, patients are screened for the presence of a particular type of ovarian cancer prior to administration of the oral formulation. In certain clinical studies, patients with a type of ovarian cancer known or believed to benefit preferentially from cytidine analog (e.g., 5-azacytidine) administration may be enrolled. In certain clinical studies, patients having ovarian cancer are enrolled without screening for particular ovarian cancer types. In certain clinical studies, patients having any type of ovarian cancer are candidates for treatment with an oral formulation provided herein. In certain clinical studies, patients may be currently undergoing additional treatment for ovarian cancer, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein (e.g., carboplatin). The additional therapeutic agent(s) may be administered in the same oral formulation as the cytidine analog, or may be co-administered (e.g., via PO, SC or IV administration) in combination with an oral formulation comprising a cytidine analog. The appropriate amount and dosing schedule for an additional therapeutic agent may be determined for a particular patient using methods known in the art.

In particular embodiments, the co-administered agent is carboplatin. In particular embodiments, the co-administered agent is paclitaxel (e.g., Abraxane®).

An association between gene methylation and ovarian cancer is known in the art. See, e.g., G. Gifford et al., *Clin. Cancer Res.*, 2004, 10:4420-26. Accordingly, in certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In certain clinical studies, patients with high levels of DNA methylation (e.g., CpG island methylation) of certain genes may be administered a cytidine analog (e.g., 5-azacytidine). In certain clinical studies, patients with low levels of DNA methylation (e.g., CpG island methylation) of certain genes may be administered a cytidine analog (e.g., 5-azacytidine). In certain clinical studies, patients with a particular DNA methylation signature (e.g., CpG island methylation) of certain genes may be administered a cytidine analog (e.g., 5-azacytidine). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349: 2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the type, stage, and progression of the patient's ovarian cancer, the patient's age and weight, the patient's prior treatment regimens, and other variables, as known in the art. n certain clinical studies, potential starting doses may be, e.g., about 50 mg, about 60 mg, about 70 mg, about 75 mg, about 80 mg, about 90 mg, about 100 mg, about 120 mg, about 140 mg, about 150 mg, about 160 mg, about 180 mg, about 200 mg, about 220 mg, about 240 mg, about 250 mg, about 300 mg, about 350 mg, about 360 mg, about 400 mg, about 420 mg, about 450 mg, about 480 mg, about 500 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. Cycles may be repeated as desired, e.g., over a period of one or more months, as disclosed herein. After a certain number of cycles, the dosage may be increased to increase the beneficial effect, provided such an increase does not cause undesirable toxicity effects. Patients may be treated for a minimum number of cycles, as disclosed herein. Complete or partial response may require additional treatment cycles. Treatment may be continued as long as the patient continues to benefit.

E. Example 5

Clinical studies are conducted to assess the ability of an oral formulation comprising a cytidine analog, such as 5-azacytidine, to treat patients having a pancreatic cancer (including, e.g., the ability to stop or reverse the growth of cancer cells in patients having pancreatic cancer). In certain clinical studies, patients are screened prior to enrollment for a particular type of pancreatic cancer prior to administration of the oral formulation. Cellular classifications of pancreatic cancers are known in the art and include, e.g., duct cell carcinoma; acinar cell carcinoma; papillary mucinous carcinoma; signet ring carcinoma; adenosquamous carcinoma; undifferentiated carcinoma; mucinous carcinoma; giant cell carcinoma; mixed type (ductal-endocrine or acinar-endocrine); small cell carcinoma; cystadenocarcinoma (serous and mucinous types); unclassified; pancreatoblastoma; papillary-cystic neoplasm (Frantz tumor); invasive adenocarcinoma associated with cystic mucinous neoplasm or intraductal papillary mucinous neoplasm; mucinous cystic tumor with dysplasia; intraductal papillary mucinous tumor with dysplasia; and pseudopapillary solid tumor. In certain clinical studies, patients are screened prior to enrollment for a particular stage of pancreatic cancer (e.g., the size of the tumor in the pancreas, whether the cancer has spread, and if so, to what parts of the body) prior to administration of the oral formulation. In certain clinical studies, pancreatic cancer patients believed to benefit preferentially from cytidine analog (e.g., 5-azacytidine) administration may be enrolled. In certain clinical studies, patients having pancreatic cancer are enrolled without screening for particular pancreatic cancer types. In certain clinical studies, patients having any type of pancreatic cancer are candidates for treatment with an oral formulation provided herein. In certain clinical studies, patients may be currently undergoing additional treatment for pancreatic cancer, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein (e.g., gemcitabine). The additional therapeutic agent(s) may be administered in the same oral formulation as the cytidine analog, or may be co-administered (e.g., via PO, SC or IV administration) in combination with an oral formulation comprising a cytidine analog. The appropriate amount and dosing schedule for an additional therapeutic agent may be determined for a particular patient using methods known in the art.

In particular embodiments, the co-administered agent is carboplatin. In particular embodiments, the co-administered agent is paclitaxel (e.g., Abraxane®).

In certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In certain clinical studies, patients with high levels of DNA methylation (e.g., CpG island methylation) of certain genes may be administered a cytidine analog (e.g., 5-azacytidine). In certain clinical studies, patients with low levels of DNA methylation (e.g., CpG island methylation) of certain genes may be administered a cytidine analog (e.g., 5-azacytidine). In certain clinical studies, patients with a particular DNA methylation signature (e.g., CpG island methylation) of certain genes may be administered a cytidine analog (e.g., 5-azacytidine). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349: 2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the type, stage, and progression of the patient's pancreatic cancer, the patient's age and weight, the patient's prior treatment regimens, and other variables, as known in the art. In certain clinical studies, potential starting doses may be, e.g., about 50 mg, about 60 mg, about 70 mg, about 75 mg, about 80 mg, about 90 mg, about 100 mg, about 120 mg, about 140 mg, about 150 mg, about 160 mg, about 180 mg, about 200 mg, about 220 mg, about 240 mg, about 250 mg, about 300 mg, about 350 mg, about 360 mg, about 400 mg, about 420 mg, about 450 mg, about 480 mg, about 500 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. Cycles may be repeated as desired, e.g., over a period of one or more months, as disclosed herein. After a certain number of cycles, the dosage may be increased to increase the beneficial effect, provided such an increase does not cause undesirable toxicity effects. Patients may be treated for a minimum number of cycles, as disclosed herein. Complete or partial response may require additional treatment cycles. Treatment may be continued as long as the patient continues to benefit.

F. Example 6

Clinical studies are conducted to assess the ability of an oral formulation comprising a cytidine analog, such as 5-azacytidine, to treat patients having a colorectal cancer (including, e.g., the ability to stop or reverse the growth of cancer cells in patients having a colorectal cancer). In certain clinical studies, patients are screened prior to enrollment for a particular type of colorectal cancer prior to administration of the oral formulation. Histologic types of colon cancers are known in the art and include, e.g., adenocarcinoma; mucinous (colloid) adenocarcinoma; signet ring adenocarcinoma; scirrhous tumors; and neuroendocrine tumors. The World Health Organization classification of tumors of the colon and rectum include (1) Epithelial Tumors, which include: Adenoma (e.g., tubular, villous, tubulovillous, and serrated); Intraepithelial neoplasia (dysplasia) associated with chronic inflammatory diseases (e.g., low-grade glandular intraepithelial neoplasia and high-grade glandular intraepithelial neoplasia); Carcinoma (e.g., adenocarcinoma, mucinous adenocarcinoma, signet-ring cell carcinoma, small cell carcinoma, adenosquamous carcinoma, medullary carcinoma, and undifferentiated carcinoma); Carcinoid (well-differentiated neuroendocrine neoplasm) (e.g., enterochromaffin (EC)-cell, serotonin-producing neoplasm, L-cell, glucagon-like peptide and pancreatic polypeptide/peptide YY (PYY)-producing tumor, and others); and Mixed carcinoma-adenocarcinoma; and (2) Non-epithelial Tumors, which include: Lipoma; Leiomyoma; Gastrointestinal stromal tumor; Leiomyosarcoma; Angiosarcoma; Kaposi sarcoma; Melanoma; and others; as well as Malignant lymphomas (e.g., marginal zone B-cell lymphoma of mucosa-associated lymphoid tissue type, mantle cell lymphoma, diffuse large B-cell lymphoma, Burkitt lymphoma, and Burkitt-like/atypical Burkitt lymphoma. In certain clinical studies, patients are screened prior to enrollment for a particular stage of colorectal cancer (e.g., the size of the tumor in the colon or rectum, whether the cancer has spread, and if so, to what parts of the body) prior to administration of the oral formulation. In certain clinical studies, colorectal cancer patients believed to benefit preferentially from cytidine analog (e.g., 5-azacytidine) administration may be enrolled. In certain clinical studies, patients having a colorectal cancer are enrolled without screening for particular colorectal cancer types. In certain clinical studies, patients having any type of colorectal cancer are candidates for treatment with an oral formulation provided herein. In certain clinical studies, patients may be currently undergoing additional treatment for colorectal cancer, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein. The additional therapeutic agent(s) may be administered in the same oral formulation as the cytidine analog, or may be co-administered (e.g., via PO, SC or IV administration) in combination with an oral formulation comprising a cytidine analog. The appropriate amount and dosing schedule for an additional therapeutic agent may be determined for a particular patient using methods known in the art.

In particular embodiments, the co-administered agent is carboplatin. In particular embodiments, the co-administered agent is paclitaxel (e.g., Abraxane®).

An association between gene methylation and colorectal cancer is known in the art. See, e.g., A. M. Jubb et al., *J. Pathol.*, 2001, 195:111-134. Accordingly, in certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In certain clinical studies, patients with high levels of DNA methylation (e.g., CpG island methylation) of certain genes may be administered a cytidine analog (e.g., 5-azacytidine). In certain clinical studies, patients with low levels of DNA methylation (e.g., CpG island methylation) of certain genes may be administered a cytidine analog (e.g., 5-azacytidine). In certain clinical studies, patients with a particular DNA methylation signature (e.g., CpG island methylation) of certain genes may be administered a cytidine analog (e.g., 5-azacytidine). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349: 2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the type, stage, and progression of the patient's colorectal cancer, the patient's age and weight, the patient's prior treatment regimens, and other variables, as known in the art. In certain clinical studies, potential starting doses may be, e.g., about 50 mg, about 60 mg, about 70 mg, about 75 mg, about 80 mg, about 90 mg, about 100 mg, about 120 mg, about 140 mg, about 150 mg, about 160 mg, about 180 mg, about 200 mg, about 220 mg, about 240 mg, about 250 mg, about 300 mg, about 350 mg, about 360 mg, about 400 mg, about 420 mg, about 450 mg, about 480 mg, about 500 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. After a certain number of cycles, the dosage may be increased to increase the beneficial effect, provided such an increase does not cause undesirable toxicity effects. Patients may be treated for a minimum number of cycles, as disclosed herein. Complete or partial response may require additional treatment cycles. Treatment may be continued as long as the patient continues to benefit.

G. Example 7

Clinical studies are conducted to assess the ability of an oral formulation comprising a cytidine analog, such as 5-azacytidine, to treat patients having a bladder cancer (including, e.g., the ability to stop or reverse the growth of cancer cells in patients having a bladder cancer). In certain clinical studies, patients are screened prior to enrollment for a particular type of bladder cancer prior to administration of the oral formulation. In certain clinical studies, patients are screened prior to enrollment for a particular stage of bladder cancer (e.g., the size of the tumor, whether the cancer has spread, and if so, to what parts of the body) prior to administration of the oral formulation. In certain clinical studies, patients are screened prior to enrollment for a particular type of bladder cancer prior to administration of the oral formulation. In certain clinical studies, bladder cancer patients believed to benefit preferentially from cytidine analog (e.g., 5-azacytidine) administration may be enrolled. In certain clinical studies, patients having a bladder cancer are enrolled without screening for particular bladder cancer types. In certain clinical studies, patients having any type of bladder cancer are candidates for treatment with an oral formulation provided herein. In certain clinical studies, patients may be currently undergoing additional treatment for bladder cancer, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein. The additional therapeutic agent(s) may be administered in the same oral formulation as the cytidine analog, or may be co-administered (e.g., via PO, SC or IV administration) in combination with an oral formulation comprising a cytidine analog. The appropriate amount and dosing schedule for an additional therapeutic agent may be determined for a particular patient using methods known in the art.

In particular embodiments, the co-administered agent is carboplatin. In particular embodiments, the co-administered agent is paclitaxel (e.g., Abraxane®).

In certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In certain clinical studies, patients with high levels of DNA methylation (e.g., CpG island methylation) of certain genes may be administered a cytidine analog (e.g., 5-azacytidine). In certain clinical studies, patients with low levels of DNA methylation (e.g., CpG island methylation) of certain genes may be administered a cytidine analog (e.g., 5-azacytidine). In certain clinical studies, patients with a particular DNA methylation signature (e.g., CpG island methylation) of certain genes may be administered a cytidine analog (e.g., 5-azacytidine). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349: 2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the type, stage, and progression of the patient's bladder cancer, the patient's age and weight, the patient's prior treatment regimens, and other variables, as known in the art. In certain clinical studies, potential starting doses may be, e.g., about 50 mg, about 60 mg, about 70 mg, about 75 mg, about 80 mg, about 90 mg, about 100 mg, about 120 mg, about 140 mg, about 150 mg, about 160 mg, about 180 mg, about 200 mg, about 220 mg, about 240 mg, about 250 mg, about 300 mg, about 350 mg, about 360 mg, about 400 mg, about 420 mg, about 450 mg, about 480 mg, about 500 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. After a certain number of cycles, the dosage may be increased to increase the beneficial effect, provided such an increase does not cause undesirable toxicity effects. Patients may be treated for a minimum number of cycles, as disclosed herein. Complete or partial response may require additional treatment cycles. Treatment may be continued as long as the patient continues to benefit.

H. Example 8

Clinical studies are conducted to assess the ability of an oral formulation comprising a cytidine analog, such as 5-azacytidine, to treat patients having a breast cancer (including, e.g., the ability to stop or reverse the growth of cancer cells in patients having a breast cancer). In certain clinical studies, patients are screened prior to enrollment for a particular type of breast cancer prior to administration of the oral formulation. In certain clinical studies, patients are screened prior to enrollment for a particular stage of breast cancer (e.g., the size of the tumor in the breast, whether the cancer has spread, and if so, to what parts of the body) prior to administration of the oral formulation. In certain clinical studies, patients are screened prior to enrollment for a particular type of breast cancer prior to administration of the oral formulation. In certain clinical studies, breast cancer patients believed to benefit preferentially from cytidine analog (e.g., 5-azacytidine) administration may be enrolled. In certain clinical studies, patients having a breast cancer are enrolled without screening for particular breast cancer types. In certain clinical studies, patients having any type of breast cancer are candidates for treatment with an oral formulation provided herein. In certain clinical studies, patients may be currently undergoing additional treatment for breast cancer, including, e.g., surgery, chemotherapy, or radiation therapy.

In certain clinical studies, patients who are administered an oral formulation comprising a cytidine analog (e.g., 5-azacytidine) may also be administered one or more additional therapeutic agents, examples of which are disclosed herein. The additional therapeutic agent(s) may be administered in the same oral formulation as the cytidine analog, or may be co-administered (e.g., via PO, SC or IV administration) in combination with an oral formulation comprising a cytidine analog. The appropriate amount and dosing schedule for an additional therapeutic agent may be determined for a particular patient using methods known in the art. In some embodiments, the co-administered agent is carboplatin. In particular embodiments, the co-administered agent is paclitaxel (e.g., Abraxane®).

In certain clinical studies provided herein, patients are screened prior to enrollment and/or monitored during the trial for DNA or RNA methylation levels, which indicate a potential response to treatment with an oral formulation comprising a cytidine analog (e.g., 5-azacytidine). In certain clinical studies, patients with high levels of DNA methylation (e.g., CpG island methylation) and/or an increased potential for transcriptional silencing of tumor-suppressor genes may be administered a cytidine analog (e.g., 5-azacytidine) known or believed to prevent or reverse hypermethylation (e.g., by reducing the activity of one or more DNA methyltransferase enzymes). In certain clinical studies, patients with high levels of DNA methylation (e.g., CpG island methylation) of certain genes may be administered a cytidine analog (e.g., 5-azacytidine). In certain clinical studies, patients with low levels of DNA methylation (e.g., CpG island methylation) of certain genes may be administered a cytidine analog (e.g., 5-azacytidine). In certain clinical studies, patients with a particular DNA methylation signature (e.g., CpG island methylation) of certain genes may be administered a cytidine analog (e.g., 5-azacytidine). In such studies, patients may also be co-administered one or more additional therapeutic agents known or believed to reduce epigenetic silencing, such as, e.g., compounds that inhibit histone deacetylase enzymes (HDACs), which regulate the acetylation and deacetylation of histone residues that increase or decrease gene expression. See, e.g., J. G. Herman & S. B. Baylin, *N. Engl. J. Med.*, 2003, 349: 2042-54; P. A. Jones & S. B. Baylin, *Nature Rev. Gen.*, 2002, 3:415-28. Suitable HDAC inhibitors for co-administration in the clinical studies disclosed herein are known in the art and/or described herein (e.g., entinostat or vorinostat).

The amount of cytidine analog (e.g., 5-azacytidine) in the oral formulations administered during the clinical studies depends, e.g., on the individual characteristics of the patient, including, inter alia, the type, stage, and progression of the patient's breast cancer, the patient's age and weight, the patient's prior treatment regimens, and other variables, as known in the art. In certain clinical studies, potential starting doses may be, e.g., about 50 mg, about 60 mg, about 70 mg, about 75 mg, about 80 mg, about 90 mg, about 100 mg, about 120 mg, about 140 mg, about 150 mg, about 160 mg, about 180 mg, about 200 mg, about 220 mg, about 240 mg, about 250 mg, about 300 mg, about 350 mg, about 360 mg, about 400 mg, about 420 mg, about 450 mg, about 480 mg, about 500 mg, about 540 mg, about 600 mg, about 660 mg, about 720 mg, about 780 mg, about 840 mg, about 900 mg, about 960 mg, about 1020 mg, or greater than about 1020 mg of the cytidine analog (e.g., 5-azacytidine) daily for a specified time period, e.g., about 1 week, about 1.5 weeks, about 2 weeks, about 2.5 weeks, about 3 weeks, about 3.5 weeks, about 1 month, about 1.5 months, about 2 months, or a longer time period. Other potential starting doses and time periods are disclosed herein. After a certain number of cycles, the dosage may be increased to increase the beneficial effect, provided such an increase does not cause undesirable toxicity effects. Patients may be treated for a minimum number of cycles, as disclosed herein. Complete or partial response may require additional treatment cycles. Treatment may be continued as long as the patient continues to benefit.

I. Example 9

The effects of AZA dose and schedule (short-term vs. extended) on pharmacodynamic markers such as DNMT1 depletion, DNA methylation, and DNA damage were evaluated in MDA-MB-231 breast cancer cells in vitro and in vivo. For in vitro experiments, MDA-MB-231 cells were treated daily with 0.1 or 0.3 µM AZA for up to 12 days, and harvested at various times during treatment, as well as up to 12 days following treatment. For in vivo studies, MDA-MB-231 tumor-bearing mice were dosed (ip) with 1 or 3 mg/kg AZA daily for 3, 7, 14, 21, or 28 days and tumors were harvested during and at several time points after the dosing period. DNA and cell lysates were prepared (from cell pellets or xenograft tumors) for DNA methylation analysis (LINE-1 or EpiTech Methyl qPCR assay) and DNMT1/γH2AX western blotting, respectively.

In both in vitro and in vivo studies, AZA caused a rapid (by 8 hours post in vivo dose), dose-dependent depletion of DNMT1 protein; when AZA treatment was halted, DNMT1 protein levels returned to basal levels within 3-4 days. Consistent with these results, AZA in vitro and in vivo caused a dose-dependent decrease in DNA methylation (LINE-1 and gene-specific) and further reduction in DNA methylation with additional days of AZA dosing. In vitro, DNA methylation returned to basal levels upon AZA removal (within 8 days); the kinetics of DNA re-methylation was slower in more hypomethylated DNA. Lastly, DNA damage was not observed in tumors from mice until 14 or 21 days of dosing with 3 mg/kg or 1 mg/kg AZA, respectively.

Thus, extended AZA dosing maintained low DNMT1 levels and DNA methylation, and induced DNA damage. These results provide a strong rationale for extended AZA dosing for the treatment of cancer patients.

J. Example 10

In patients treated with 5-azacytidine alone or in combination with an additional therapeutic agent such as CDBCA or ABX, the pharmacodynamic effects are determined using one or more methods provided in the table below. In addition, the methods below can be used as predictive biomarkers to predict clinical response to treatments.

| Tissue | Analyte | Assay | PD[1] | Pred.[2] |
|---|---|---|---|---|
| Whole Blood (PBMCs) | Genomic DNA | Infinium ® Methylation27 Array | ✓ | |
| Plasma | Free DNA | Infinium ® Methylation450 Array | ✓ | ✓ |
| Tumor (Fresh Frozen) | Genomic DNA | Infinium ® Methylation450 Array | ✓ | ✓ |
| | RNA | Candidate gene expression analysis | ✓ | ✓ |
| Tumor (FFPE) | Protein (IHC) | DNMT1, DNMT3A, pH2AX, cPARP | ✓ | ✓ |
| | | Candidate short half-life proteins | ✓ | ✓ |

[1]PD: Change at Day 15 from baseline.
[2]Predictive Biomarker: Baseline in relation to clinical response.

In one embodiment, PBMC DNA was used for assessing changes in DNA methylation, using assays such as LINE-1 methylation, %5mdC mass spec, Infinium® Methylation27 Array, and Infinium® Methylation450 Array. In one study, DNA methylation (LINE-1) in PBMC DNAs from patients in clinical studies described in Example 1, dosed with 200 mg oral AZA alone or in combination with CDBCA or ABX, was measured on Days 1, 8, and 15 of 21-day cycle. Decreases in LINE-1 methylation were observed for two patients in Arm C. In one study, %5mdC in PBMC DNAs from patients in clinical studies described in Example 1, dosed with 200 mg oral AZA alone or in combination with CDBCA or ABX, was measured on Days 1, 8, and 15 of 21-day cycle. In one study, methylation levels were measured on Days 1, 8, and 15 of 21-day cycle using Infinium® Methylation27 Array (patients dosed with 200 mg oral AZA alone or in combination with CDBCA or ABX) and density profiles of average methylation levels were analyzed. Upon treatment, decreases in hypermethylated loci (beta>0.7) were observed in PBMCs of Arm C patients; no change in DNA methylation was observed in PBMCs of Arm A patients, and minor decrease in DNA methylation was observed in PBMCs of Arm B patients. In another study, methylation levels were measured using Infinium® Methylation450 Array (patients dosed with 300 mg oral AZA alone or in combination with CDBCA or ABX) and density profiles of average methylation levels were analyzed, as well as % change of hypermethylated loci (beta>0.7) upon treatment. The data suggested that the decreases in DNA methylation correlated with the PK exposure of AZA in the patients.

In summary, DNA hypomethylation in PBMCs was observed in patients dosed with 200 mg oral AZA alone or in combination with an additional therapeutic agent (5/6 Arm C patients; 2/6 Arm B patients; and 0/6 Arm A patients). DNA hypomethylation in PBMCs was observed in patients dosed with 300 mg oral AZA alone or in combination with an additional therapeutic agent (3/3 Arm C patients; and 2/4 Arm A patients). Decreases in DNA methylation appeared to correlate with PK exposure of AZA in the patients, for example, were observed in patients with $AUC_{inf}$>350 ng*hr/mL.

K. Example 11

FIG. 6 shows in vitro modeling of the dosing schema of the clinical study described in Example 1. DNA hypomethylation (e.g., LINE-1, p16) was measured 72 hours after AZA treatment alone or in combination with CBDCA or ABX. p16 (mRNA) re-expression was determined 72 hours after AZA treatment alone or in combination with CBDCA or ABX. Ninety-two cancer cell lines were tested in order to identify specific tumor types that become sensitized to CBDCA or ABX after treatment with AZA (bladder cancer n=8; head and neck cancer n=8, breast cancer n=21; lung cancer n=35; pancreatic cancer n=7; ovarian cancer n=7; and melanoma n=6). The result from this study can also be used to identify predictive biomarkers for enhanced sensitivity to the combination treatment of CBDCA or ABX with AZA.

Interaction of AZA treatment with ABX treatment was evaluated, in the following cancer cell lines: (1) bladder cancer cell lines, including 5637, J82, HT-1376, SCaBER, TCCSUP, and UM-UC-3, which showed additive effects; (2) head and neck cancer cell lines, including A253, BHY, CAL-27, CAL-33, and FIN, which showed additive effects; (3) breast cancer cell lines, including ZR-75-1, CAL-51, MDA-MB-231, BT-549, Hs578t, HCC1500, HCC-1187, and ZR-75-30, which showed additive effects; (4) pancreatic cancer cell lines, including MiaPaca-2, which showed synergistic effects; (5) NSCLC cell lines, including H1792, which showed synergistic effects; and H460, H1299, H23, H1975, H2122, H838, H28, H1838, CALU-3, H2030, H1437, H596, H647, and H1650, which showed additive effects; (6) ovarian cancer cell lines, including OVCAR-3, OVCAR-5, OVCAR-8, SKOV3, and IGR-OV1, which showed additive effects; and (7) melanoma cell lines, including Malme 3M and SKMEL5, which showed additive effects. However, antagonism was observed for combination of AZA with ABX in ¼ of the cell lines tested, including breast (⅓), NSCLC (¼), and melanoma (⅔) cell lines. In other experiments, antagonism was also observed in some cell lines with DAC (decitabine) priming.

Interaction of AZA treatment with CBDCA treatment was evaluated, in the following cancer cell lines: (1) bladder cancer cell lines, including UM-UC-3, which showed synergistic effects; and 5637, J82, HT-1376, SCaBER, and TCCSUP, which showed additive effects; (2) head and neck cancer cell lines, including Detroit562 and FADU, which showed synergistic effects; and A253, BHY, CAL-27, CAL-33, FIN, and RPMI-2650, which showed additive effects; (3) breast cancer cell lines, including BT-549, Hs578t, MDA-MB-157, SUM-149, and HCC-38, which showed synergistic effects; and T47D, ZR-75-1, CAL-51, CAL-120, MCF7, HCC1500, AU565, HCC-1187, MDA-MB-436, and ZR-75-30, which showed additive effects; (4) pancreatic cancer cell lines, including BxPC3, MiaPaca-2, and Hs766t, which showed synergistic effects; (5) NSCLC cell lines, including H460, H1299, A549, H838, HOP62, H1792, H1838, H1755, H2030, H1437, HOP92, and H2110, which showed synergistic effects; and H23, H1975, H226, H2122, H28, H2228, H727, SK-LU-1, H520, H596, H647, H1568, H1944, and H1650, which showed additive effects; (6) ovarian cancer cell lines, including OVCAR-3, OVCAR-4, OVCAR-5, OVCAR-8, SKOV3, and IGR-OV1, which showed additive effects; and (7) melanoma cell lines, including SKMEL5, which showed synergistic effects; and M14, Malme 3M, MeWO, SKMEL2, and SKMEL28, which showed additive effects. Additivity or synergy was observed for combination of AZA with CBDCA in the majority of cell lines tested (e.g., about ⅓ NSCLC cell lines showed synergy). In other experiments, additivity or synergy was also observed in some cell lines with DAC (decitabine) priming.

Moreover, for the combination of AZA with CBDCA, selected panels of cell lines which showed synergistic or additive effects were further studied in order to identify predictive biomarkers to predict synergy of the combination. The selected cell lines included (1) UM-UC-3 (bladder), FADU (head and neck), MiaPaca-2 (pancreatic), H838 (NSCLC), H2110 (NSCLC), and HOP62 (NSCLC), which showed synergistic effects, and (2) CAL-120 (breast), AU565 (breast), Detroit562 (head and neck), H520 (NSCLC), H1838 (NSCLC), H1568 (NSCLC), and CALU-6 (NSCLC). Basal gene expression and DNA methylation were compared. In addition, AZA-induced changes in gene expression and DNA methylation were compared. The extent of synergy was calculated using AAUC values. Strong synergy was observed in 18 hours to 72 hours or more of AZA priming, for example, in HOP62, UM-UC-3, and FADU.

Similar results were observed in the kinetics of AZA-induced DNMT1 depletion when comparing synergistic cell lines with additive cell lines (e.g., HOP62 vs. H1568; H838 vs. H520, FADU vs. Detroit562), and similar extent of DNMT1 depletion at 48 hours were observed when comparing synergistic cell lines with additive cell lines. Similar effects of DNA hypomethylation (LINE-1) was observed in when comparing synergistic cell lines with additive cell lines upon AZA treatment alone or in combination with CBDCA (e.g., in FADU, Detroit562, HOP62, and H520). Dramatic increase in PARP cleavage in the synergistic cell line H838 was observed upon treatment with combination of AZA and CBDCA, suggesting synergistic effect of the combination on PARP cleavage in H838 cells.

Furthermore, to identify predictive biomarkers for enhanced sensitivity, basal gene expression, promoter methylation, and mutation status are analyzed in selected cancer cell lines. Moreover, gene expression and promoter methylation changes upon AZA treatment are analyzed in selected cancer cell lines.

The present disclosure has been described in connection with certain embodiments and examples; however, unless otherwise indicated, the claimed invention should not be unduly limited to such specific embodiments and examples.

What is claimed is:

1. A method for treating a subject having non-small cell lung cancer, wherein the method comprises orally administering to the subject a pharmaceutical composition comprising 5-azacytidine, or a pharmaceutically acceptable solvate or hydrate thereof and at least one pharmaceutically acceptable excipient, wherein the pharmaceutical composition comprising 5-azacytidine is a tablet comprising about 100 mg, about 200 mg, about 300 mg, about 400 mg, about 500 mg, or about 600 mg of 5-azacytidine; and the method further comprises administering at least one additional therapeutic agent comprising a platinum agent.

2. The method of claim 1, wherein the non-small cell lung cancer is a relapsed or refractory non-small cell lung cancer.

3. The method of claim 1, wherein the platinum agent is carboplatin.

4. The method of claim 1, wherein the method comprises the steps of:
   (i) administering 5-azacytidine to the subject for 1, 2, 3, 4, 5, 6, 7, 8, 9, 10, 11, 12, 13, 14, 15, 16, 17, 18, 19, 20, or 21 days; and
   (ii) administering the additional therapeutic agent to the subject for one or more days.

5. The method of claim 4, wherein the additional therapeutic agent is administered parenterally.

6. The method of claim 4, wherein the additional therapeutic agent is administered orally.

7. The method of claim 4, wherein step (ii) further comprises administering the 5-azacytidine orally for 1, 2, 3, 4, 5, 6, 7, 8, 9, 10, 11, 12, 13, or 14 days.

8. The method of claim 4, wherein the method comprises the sequential steps of:

(i) administering 5-azacytidine to the subject for 7 days;
(ii) administering the additional therapeutic agent to the subject for 1 day;
(iii) administering 5-azacytidine to the subject for 6 days; and
(iv) repeating steps (i) to (iii) after 7 days of resting period.

9. The method of claim 4, wherein the method comprises the sequential steps of:
(i) administering 5-azacytidine to the subject for 7 days;
(ii) administering 5-azacytidine and the additional therapeutic agent to the subject for 1 day;
(iii) administering 5-azacytidine to the subject for 6 days; and
(iv) repeating steps (i) to (iii) after 7 days of resting period.

10. The method of claim 4, wherein the method comprises the sequential steps of:
(i) administering 5-azacytidine to the subject for 7 days;
(ii) administering 5-azacytidine and the additional therapeutic agent to the subject for 1 day;
(iii) administering 5-azacytidine to the subject for 6 days;
(iv) administering the additional therapeutic agent to the subject for 1 day; and
(v) repeating steps (i) to (iv) after 6 days of resting period.

11. The method of claim 4, wherein the method comprises the sequential steps of:
(i) administering 5-azacytidine to the subject for 7 days;
(ii) administering 5-azacytidine and the additional therapeutic agent to the subject for 1 day;
(iii) administering 5-azacytidine to the subject for 6 days;
(iv) administering the additional therapeutic agent to the subject for 1 day;
(v) after 6 days of resting period, administering 5-azacytidine and the additional therapeutic agent to the subject for 1 day;
(vi) administering 5-azacytidine to the subject for 6 days; and
(vii) repeating steps (i) to (vi).

12. The method of claim 1, wherein the method comprises administering 5-azacytidine to the subject for at least 1, at least 2, at least 3, at least 4, at least 5, at least 6, or at least 7 days, before administering the additional therapeutic agent to the subject.

13. The method of claim 12, wherein the additional therapeutic agent is administered parenterally for one or more days.

14. The method of claim 12, wherein the additional therapeutic agent is administered orally for one or more days.

15. The method of claim 1, wherein the pharmaceutical composition comprises about 100 mg of 5-azacytidine.

16. The method of claim 1, wherein the pharmaceutical composition comprises about 200 mg of 5-azacytidine.

17. The method of claim 1, wherein the pharmaceutical composition comprises about 300 mg of 5-azacytidine.

18. The method of claim 1, wherein the subject is a human.

19. The method of claim 4, wherein the method comprises the sequential steps of:
(i) administering 5-azacytidine and the additional therapeutic agent to the subject for 1 day;
(ii) administering 5-azacytidine to the subject for 13 days; and
(iii) repeating steps (i) and (ii) after 7 days of resting period.

20. The method of claim 4, wherein the method comprises the sequential steps of:
(i) administering 5-azacytidine and the additional therapeutic agent to the subject for 1 day;
(ii) administering 5-azacytidine to the subject for 20 days; and
(iii) repeating steps (i) and (ii).

21. The method of claim 4, wherein the method comprises the sequential steps of:
(i) administering 5-azacytidine and the additional therapeutic agent to the subject for 1 day;
(ii) administering 5-azacytidine to the subject for 6 days;
(iii) administering 5-azacytidine and the additional therapeutic agent to the subject for 1 day;
(iv) administering 5-azacytidine to the subject for 6 days;
(v) repeating steps (i) to (iv) after 7 days of resting period.

22. The method of claim 4, wherein the method comprises the sequential steps of:
(i) administering 5-azacytidine and the additional therapeutic agent to the subject for 1 day;
(ii) administering 5-azacytidine to the subject for 6 days;
(iii) administering 5-azacytidine and the additional therapeutic agent to the subject for 1 day;
(iv) administering 5-azacytidine to the subject for 13 days;
(v) repeating steps (i) to (iv).

* * * * *